US010669555B2

(12) United States Patent
Abad et al.

(10) Patent No.: US 10,669,555 B2
(45) Date of Patent: Jun. 2, 2020

(54) ***BACILLUS THURINGIENSIS* GENE WITH LEPIDOPTERAN ACTIVITY**

(71) Applicant: PIONEER HI-BRED INTERNATIONAL, INC., Johnston, IA (US)

(72) Inventors: Andre Roger Abad, Leander, TX (US); David Charles Cerf, Palo Alto, CA (US); Scott Henry Diehn, West Des Moines, IA (US); Hua Dong, Johnston, IA (US); Xiaomei Shi, Johnston, IA (US); Thomas Chad Wolfe, Des Moines, IA (US); Lan Zhou, Ankeny, IA (US)

(73) Assignee: PIONEER HI-BRED INTERNATIONAL, INC. IA (US)

(*) Notice: Subject to any disclaimer, the term of this patent is extended or adjusted under 35 U.S.C. 154(b) by 0 days.

(21) Appl. No.: 16/072,698

(22) PCT Filed: Jan. 25, 2017

(86) PCT No.: PCT/US2017/014817

§ 371 (c)(1),
(2) Date: Jul. 25, 2018

(87) PCT Pub. No.: WO2017/132188

PCT Pub. Date: Aug. 3, 2017

(65) Prior Publication Data

US 2019/0085037 A1 Mar. 21, 2019

Related U.S. Application Data

(60) Provisional application No. 62/287,281, filed on Jan. 26, 2016.

(51) Int. Cl.
*C12N 15/82* (2006.01)
*A01N 37/46* (2006.01)
*C07K 14/325* (2006.01)

(52) U.S. Cl.
CPC ......... *C12N 15/8286* (2013.01); *A01N 37/46* (2013.01); *C07K 14/325* (2013.01); *C07K 2319/02* (2013.01); *C07K 2319/036* (2013.01); *Y02A 40/162* (2018.01)

(58) Field of Classification Search
CPC .......................... C12N 15/8286; C07K 14/325
See application file for complete search history.

(56) References Cited

U.S. PATENT DOCUMENTS

| | | | | |
|---|---|---|---|---|
| 2004/0197916 A1* | 10/2004 | Carozzi | C07K 14/325 | 435/468 |
| 2013/0254933 A1* | 9/2013 | Kramer | C07K 14/325 | 800/279 |

OTHER PUBLICATIONS

International Search Report and Written Opinion, International Application No. PCT/US2017/014817 dated Jul. 12, 2017.

* cited by examiner

*Primary Examiner* — Lee A Visone

(57) ABSTRACT

The disclosure provides nucleic acids, and variants and fragments thereof, obtained from strains of *Bacillus thuringiensis* encoding polypeptides having pesticidal activity against insect pests, including *Lepidoptera*. Particular embodiments of the disclosure provide isolated nucleic acids encoding pesticidal proteins, pesticidal compositions, DNA constructs, and transformed microorganisms and plants comprising a nucleic acid of the embodiments. These compositions find use in methods for controlling pests, especially plant pests.

27 Claims, No Drawings

Specification includes a Sequence Listing.

BACILLUS THURINGIENSIS GENE WITH LEPIDOPTERAN ACTIVITY

CROSS-REFERENCE TO RELATED APPLICATIONS

This application is a 371 (National Stage) of PCT/US17/14817 filed Jan. 25, 2017, which claims priority to U.S. Provisional Application No. 61/287,281, filed Jan. 26, 2016, which is hereby incorporated herein in its entirety by reference.

REFERENCE TO SEQUENCE LISTING SUBMITTED ELECTRONICALLY

A sequence listing having the file name "6060WOPCT_sequence_listing.txt" created on Jan. 12, 2016, and having a size of 256 kilobytes is filed in computer readable form concurrently with the specification. The sequence listing is part of the specification and is herein incorporated by reference in its entirety.

FIELD

The present disclosure relates to naturally-occurring and recombinant nucleic acids obtained from novel *Bacillus thuringiensis* genes that encode pesticidal polypeptides characterized by pesticidal activity against insect pests. Compositions and methods of the disclosure utilize the disclosed nucleic acids, and their encoded pesticidal polypeptides, to control plant pests.

BACKGROUND

Insect pests are a major factor in the loss of the world's agricultural crops. For example, armyworm feeding, black cutworm damage, or European corn borer damage can be economically devastating to agricultural producers. Insect pest-related crop loss from European corn borer attacks on field and sweet corn alone has reached about one billion dollars a year in damage and control expenses.

Traditionally, the primary method for impacting insect pest populations is the application of broad-spectrum chemical insecticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including *Lepidoptera, Diptera, Coleoptera, Hemiptera*, and others. *Bacillus thuringiensis* (Bt) and *Bacillus papilliae* are among the most successful biocontrol agents discovered to date. Insect pathogenicity has also been attributed to strains of *Bacillus larvae, Bacillus lentimorbus, Bacillus sphaericus* (Harwook, ed., ((1989) *Bacillus* (Plenum Press), 306) and *Bacillus cereus* (WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial insecticides, particularly those obtained from *Bacillus* strains, have played an important role in agriculture as alternatives to chemical pest control. Recently, agricultural scientists have developed crop plants with enhanced insect resistance by genetically engineering crop plants to produce pesticidal proteins from *Bacillus*. For example, corn and cotton plants have been genetically engineered to produce pesticidal proteins isolated from strains of Bt (see, e.g., Aronson (2002) *Cell Mol. Life Sci.* 59(3):417-425; Schnepf et al. (1998) *Microbiol Mol Biol Rev.* 62(3):775-806). These genetically engineered crops are now widely used in American agriculture and have provided the farmer with an environmentally friendly alternative to traditional insect-control methods. In addition, potatoes genetically engineered to contain pesticidal Cry toxins have been sold to the American farmer. While they have proven to be very successful commercially, these genetically engineered, insect-resistant crop plants provide resistance to only a narrow range of the economically important insect pests.

Accordingly, there remains a need for new Bt toxins with a broader range of insecticidal activity against insect pests, e.g., toxins which are active against a greater variety of insects from the order *Lepidoptera*. In addition, there remains a need for biopesticides having activity against a variety of insect pests and for biopesticides which have improved insecticidal activity.

SUMMARY

Compositions and methods are provided for impacting insect pests. More specifically, the present disclosure relate to methods of impacting insects utilizing nucleotide sequences encoding insecticidal peptides to produce transformed microorganisms and plants that express an insecticidal polypeptide of the embodiments. In some aspects, the nucleotide sequences encode polypeptides that are pesticidal for at least one insect belonging to the order *Lepidoptera*.

The present disclosure provides nucleic acids of SEQ ID NO: 1 and SEQ ID NO: 3 and fragments and variants thereof, which encode polypeptides of SEQ ID NO: 2 and SEQ ID NO: 4, respectively, that possess pesticidal activity against insect pests. The disclosure provides fragments and variants of the disclosed nucleotide sequence that encode biologically active (e.g., insecticidal) polypeptides.

The embodiments further provide isolated pesticidal (e.g., insecticidal) polypeptides encoded by either a naturally occurring, or a modified (e.g., mutagenized or manipulated) nucleic acid of the embodiments. In particular examples, pesticidal proteins of the embodiments include fragments of full-length proteins and polypeptides that are produced from mutagenized nucleic acids designed to introduce particular amino acid sequences into the polypeptides of the embodiments. In particular embodiments, the polypeptides have enhanced pesticidal activity relative to the activity of the naturally occurring polypeptide from which they are derived.

The nucleic acids of the embodiments can also be used to produce transgenic (e.g., transformed) monocot or dicot plants that are characterized by genomes that comprise at least one stably incorporated nucleotide construct comprising a coding sequence of the embodiments operably linked to a promoter that drives expression of the encoded pesticidal polypeptide. Accordingly, transformed plant cells, plant tissues, plants, and seeds thereof are also provided.

In a particular embodiment, a transformed plant can be produced using a nucleic acid that has been optimized for increased expression in a host plant. For example, one of the pesticidal polypeptides of the embodiments can be back-translated to produce a nucleic acid comprising codons optimized for expression in a particular host, for example a crop plant such as a corn (*Zea mays*) plant. Expression of a coding sequence by such a transformed plant (e.g., dicot or monocot) will result in the production of a pesticidal polypeptide and confer increased insect resistance to the plant. Some embodiments provide transgenic plants expressing pesticidal polypeptides that find use in methods for impacting various insect pests.

The embodiments further include pesticidal or insecticidal compositions containing the insecticidal polypeptides of the embodiments, and can optionally comprise further insecticidal peptides. The embodiments encompass the application of such compositions to the environment of insect pests in order to impact the insect pests.

DETAILED DESCRIPTION

The embodiments of the disclosure are drawn to compositions and methods for impacting insect pests, particularly plant pests. More specifically, the isolated nucleic acid of the embodiments, and fragments and variants thereof, comprise nucleotide sequences that encode pesticidal polypeptides (e.g., proteins). The disclosed pesticidal proteins are biologically active (e.g., pesticidal) against insect pests such as, but not limited to, insect pests of the order *Lepidoptera*.

The compositions of the embodiments comprise isolated nucleic acids, and fragments and variants thereof, which encode pesticidal polypeptides, expression cassettes comprising nucleotide sequences of the embodiments, isolated pesticidal proteins, and pesticidal compositions. Some embodiments provide modified pesticidal polypeptides characterized by improved insecticidal activity against Lepidopterans relative to the pesticidal activity of the corresponding wild-type protein. The embodiments further provide plants and microorganisms transformed with these novel nucleic acids, and methods involving the use of such nucleic acids, pesticidal compositions, transformed organisms, and products thereof in impacting insect pests.

The nucleic acids and nucleotide sequences of the embodiments may be used to transform any organism to produce the encoded pesticidal proteins. Methods are provided that involve the use of such transformed organisms to impact or control plant pests. The nucleic acids and nucleotide sequences of the embodiments may also be used to transform organelles such as chloroplasts (McBride et al. (1995) *Biotechnology* 13: 362-365; and Kota et al. (1999) *Proc. Natl. Acad. Sci. USA* 96: 1840-1845).

The embodiments further relate to the identification of fragments and variants of the naturally-occurring coding sequence that encode biologically active pesticidal proteins. The nucleotide sequences of the embodiments find direct use in methods for impacting pests, particularly insect pests such as pests of the order *Lepidoptera*. Accordingly, the embodiments provide new approaches for impacting insect pests that do not depend on the use of traditional, synthetic chemical insecticides. The embodiments involve the discovery of naturally-occurring, biodegradable pesticides and the genes that encode them.

The embodiments further provide fragments and variants of the naturally occurring coding sequence that also encode biologically active (e.g., pesticidal) polypeptides. The nucleic acids of the embodiments encompass nucleic acid or nucleotide sequences that have been optimized for expression by the cells of a particular organism, for example nucleic acid sequences that have been back-translated (i.e., reverse translated) using plant-preferred codons based on the amino acid sequence of a polypeptide having enhanced pesticidal activity. The embodiments further provide mutations which confer improved or altered properties on the polypeptides of the embodiments. See, e.g. U.S. Pat. No. 7,462,760.

In the description that follows, a number of terms are used extensively. The following definitions are provided to facilitate understanding of the embodiments.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to that of naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

As used herein, "full-length sequence" in reference to a specified polynucleotide or its encoded protein means having the entire nucleic acid sequence or the entire amino acid sequence of a native (non-synthetic), endogenous sequence. A full-length polynucleotide encodes the full-length, catalytically active form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited. Thus, where the term "antisense" is used in the context of a particular nucleotide sequence, the term refers to the complementary strand of the reference transcription product.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the embodiments can be produced either from a nucleic acid disclosed herein, or by the use of standard molecular biology techniques. For example, a protein of the embodiments can be produced by expression of a recombinant nucleic acid of the embodiments in an appropriate host cell, or alternatively by a combination of ex vivo procedures.

As used herein, the terms "isolated" and "purified" are used interchangeably to refer to nucleic acids or polypeptides or biologically active portions thereof that are substantially or essentially free from components that normally accompany or interact with the nucleic acid or polypeptide as found in its naturally occurring environment. Thus, an isolated or purified nucleic acid or polypeptide is substantially free of other cellular material or culture medium when produced by recombinant techniques, or substantially free of chemical precursors or other chemicals when chemically synthesized.

An "isolated" nucleic acid is generally free of sequences (such as, for example, protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acids can contain less than about 5 kb, 4 kb, 3 kb, 2 kb, 1 kb, 0.5 kb, or 0.1 kb of nucleotide sequences that naturally flank the nucleic acids in genomic DNA of the cell from which the nucleic acid is derived.

As used herein, the term "isolated" or "purified" as it is used to refer to a polypeptide of the embodiments means that the isolated protein is substantially free of cellular material and includes preparations of protein having less than about 30%, 20%, 10%, or 5% (by dry weight) of contaminating protein. When the protein of the embodiments or biologically active portion thereof is recombinantly produced, culture medium represents less than about 30%, 20%, 10%, or 5% (by dry weight) of chemical precursors or non-protein-of-interest chemicals.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

As used herein, the term "impacting insect pests" refers to effecting changes in insect feeding, growth, and/or behavior at any stage of development, including but not limited to: killing the insect; retarding growth; preventing reproductive capability; antifeedant activity; and the like.

As used herein, the terms "pesticidal activity" and "insecticidal activity" are used synonymously to refer to activity of an organism or a substance (such as, for example, a protein) that can be measured by, but is not limited to, pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. For example, "pesticidal proteins" are proteins that display pesticidal activity by themselves or in combination with other proteins.

As used herein, the term "pesticidally effective amount" means a quantity of a substance or organism that has pesticidal activity when present in the environment of a pest. For each substance or organism, the pesticidally effective amount is determined empirically for each pest affected in a specific environment. Similarly, an "insecticidally effective amount" may be used to refer to a "pesticidally effective amount" when the pest is an insect pest.

As used herein, the term "recombinantly engineered" or "engineered" means the utilization of recombinant DNA technology to introduce (e.g., engineer) a change in the protein structure based on an understanding of the protein's mechanism of action and a consideration of the amino acids being introduced, deleted, or substituted.

As used herein, the term "mutant nucleotide sequence" or "mutation" or "mutagenized nucleotide sequence" means a nucleotide sequence that has been mutagenized or altered to contain one or more nucleotide residues (e.g., base pair) that is not present in the corresponding wild-type sequence. Such mutagenesis or alteration consists of one or more additions, deletions, or substitutions or replacements of nucleic acid residues. When mutations are made by adding, removing, or replacing an amino acid of a proteolytic site, such addition, removal, or replacement may be within or adjacent to the proteolytic site motif, so long as the object of the mutation is accomplished (i.e., so long as proteolysis at the site is changed).

A mutant nucleotide sequence can encode a mutant insecticidal toxin showing improved or decreased insecticidal activity, or an amino acid sequence which confers improved or decreased insecticidal activity on a polypeptide containing it. As used herein, the term "mutant" or "mutation" in the context of a protein a polypeptide or amino acid sequence refers to a sequence which has been mutagenized or altered to contain one or more amino acid residues that are not present in the corresponding wild-type sequence. Such mutagenesis or alteration consists of one or more additions, deletions, or substitutions or replacements of amino acid residues. A mutant polypeptide shows improved or decreased insecticidal activity, or represents an amino acid sequence which confers improved insecticidal activity on a polypeptide containing it. Thus, the term "mutant" or "mutation" refers to either or both of the mutant nucleotide sequence and the encoded amino acids. Mutants may be used alone or in any compatible combination with other mutants of the embodiments or with other mutants. A "mutant polypeptide" may conversely show a decrease in insecticidal activity. Where more than one mutation is added to a particular nucleic acid or protein, the mutations may be added at the same time or sequentially; if sequentially, mutations may be added in any suitable order.

As used herein, the term "improved insecticidal activity" or "improved pesticidal activity" refers to an insecticidal polypeptide of the embodiments that has enhanced insecticidal activity relative to the activity of its corresponding wild-type protein, and/or an insecticidal polypeptide that is effective against a broader range of insects, and/or an insecticidal polypeptide having specificity for an insect that is not susceptible to the toxicity of the wild-type protein. A finding of improved or enhanced pesticidal activity requires a demonstration of an increase of pesticidal activity of at least 10%, against the insect target, or at least 20%, 25%, 30%, 35%, 40%, 45%, 50%, 60%, 70%, 100%, 150%, 200%, or 300% or greater increase of pesticidal activity relative to the pesticidal activity of the wild-type insecticidal polypeptide determined against the same insect.

For example, an improved pesticidal or insecticidal activity is provided where a wider or narrower range of insects is impacted by the polypeptide relative to the range of insects that is affected by a wild-type Bt toxin. A wider range of impact may be desirable where versatility is desired, while a narrower range of impact may be desirable where, for example, beneficial insects might otherwise be impacted by use or presence of the toxin. While the embodiments are not bound by any particular mechanism of action, an improved pesticidal activity may also be provided by changes in one or more characteristics of a polypeptide; for example, the stability or longevity of a polypeptide in an insect gut may be increased relative to the stability or longevity of a corresponding wild-type protein.

The term "toxin" as used herein refers to a polypeptide showing pesticidal activity or insecticidal activity or improved pesticidal activity or improved insecticidal activity. "Bt" or "*Bacillus thuringiensis*" toxin is intended to include the broader class of Cry toxins found in various strains of Bt, which includes such toxins as, for example, Cry1s, Cry2s, or Cry3s.

The terms "proteolytic site" or "cleavage site" refer to an amino acid sequence which confers sensitivity to a class of proteases or a particular protease such that a polypeptide containing the amino acid sequence is digested by the class of proteases or particular protease. A proteolytic site is said to be "sensitive" to the protease(s) that recognize that site. It is appreciated in the art that the efficiency of digestion will vary, and that a decrease in efficiency of digestion can lead to an increase in stability or longevity of the polypeptide in an insect gut. Thus, a proteolytic site may confer sensitivity to more than one protease or class of proteases, but the efficiency of digestion at that site by various proteases may vary. Proteolytic sites include, for example, trypsin sites, chymotrypsin sites, and elastase sites.

Research has shown that the insect gut proteases of Lepidopterans include trypsins, chymotrypsins, and elastases. See, e.g., Lenz et al. (1991) *Arch. Insect Biochem. Physiol.* 16: 201-212; and Hedegus et al. (2003) *Arch. Insect Biochem. Physiol.* 53: 30-47. For example, about 18 different trypsins have been found in the midgut of *Helicoverpa armigera* larvae (see Gatehouse et al. (1997) *Insect Biochem. Mol. Biol.* 27: 929-944). The preferred proteolytic substrate sites of these proteases have been investigated. See, e.g., Peterson et al. (1995) *Insect Biochem. Mol. Biol.* 25: 765-774.

Efforts have been made to understand the mechanism of action of Bt toxins and to engineer toxins with improved properties. It has been shown that insect gut proteases can affect the impact of Bt Cry proteins on the insect. Some proteases activate the Cry proteins by processing them from a "protoxin" form into a toxic form, or "toxin." See, Oppert (1999) *Arch. Insect Biochem. Phys.* 42: 1-12; and Carroll et al. (1997) *J. Invertebrate Pathology* 70: 41-49. This activation of the toxin can include the removal of the N- and C-terminal peptides from the protein and can also include internal cleavage of the protein. Other proteases can degrade the Cry proteins. See Oppert, ibid.

A comparison of the amino acid sequences of Cry toxins of different specificities reveals five highly-conserved sequence blocks. Structurally, the toxins comprise three distinct domains which are, from the N- to C-terminus: a cluster of seven alpha-helices implicated in pore formation (referred to as "domain 1"), three anti-parallel beta sheets implicated in cell binding (referred to as "domain 2"), and a beta sandwich (referred to as "domain 3"). The location and properties of these domains are known to those of skill in the art. See, for example, Li et al. (1991) *Nature*, 305:815-821 and Morse et al. (2001) *Structure*, 9:409-417. When reference is made to a particular domain, such as domain 1, it is understood that the exact endpoints of the domain with regard to a particular sequence are not critical so long as the sequence or portion thereof includes sequence that provides at least some function attributed to the particular domain. Thus, for example, when referring to "domain 1," it is intended that a particular sequence includes a cluster of seven alpha-helices, but the exact endpoints of the sequence used or referred to with regard to that cluster are not critical. One of skill in the art is familiar with the determination of such endpoints and the evaluation of such functions.

In an effort to better characterize and improve Bt toxins, strains of the bacterium Bt were studied. Crystal preparations prepared from cultures of the Bt strains were discovered to have pesticidal activity against numerous Lepidopteran pests (see, e.g., Experimental Example 1). An effort was undertaken to identify the nucleotide sequences encoding the crystal proteins from the selected strains, and the wild-type (i.e., naturally occurring) nucleic acids of the embodiments were isolated from these bacterial strains, cloned into an expression vector, and transformed into *E. coli*. Depending upon the characteristics of a given preparation, it was recognized that the demonstration of pesticidal activity sometimes required trypsin pretreatment to activate the pesticidal proteins. Thus, it is understood that some pesticidal proteins require protease digestion (e.g., by trypsin, chymotrypsin, and the like) for activation, while other proteins are biologically active (e.g., pesticidal) in the absence of activation.

Such molecules may be altered by means described, for example, U.S. Pat. No. 7,462,760. In addition, nucleic acid sequences may be engineered to encode polypeptides that contain additional mutations that confer improved or altered pesticidal activity relative to the pesticidal activity of the naturally occurring polypeptide. The nucleotide sequences of such engineered nucleic acids comprise mutations not found in the wild type sequences.

The mutant polypeptides of the embodiments are generally prepared by a process that involves the steps of: obtaining a nucleic acid sequence encoding a Cry family polypeptide; analyzing the structure of the polypeptide to identify particular "target" sites for mutagenesis of the underlying gene sequence based on a consideration of the proposed function of the target domain in the mode of action of the toxin; introducing one or more mutations into the nucleic acid sequence to produce a desired change in one or more amino acid residues of the encoded polypeptide sequence; and assaying the polypeptide produced for pesticidal activity.

Many of the Bt insecticidal toxins are related to various degrees by similarities in their amino acid sequences and tertiary structure and means for obtaining the crystal structures of Bt toxins are well known. Exemplary high-resolution crystal structure solution of Cry3A, Cry3B, and Cry1A polypeptides are available in the literature. The solved structure of Cry3A (Li et al. (1991) *Nature* 353:815-821) and Cry1A (Grochulski et al. (1995) *J. Mol. Biol.* 254:447-464) provide insight into the relationship between structure and function of Cry toxins. A combined consideration of the published structural analyses of Bt toxins and the reported function associated with particular structures, motifs, and the like indicates that specific regions of the toxin are correlated with particular functions and discrete steps of the mode of action of the protein. For example, many toxins isolated from Bt are generally described as comprising three domains: a seven-helix bundle that is involved in pore formation, a three-sheet domain that has been implicated in receptor binding, and a beta-sandwich motif (Li et al. (1991) *Nature* 305: 815-821). Cry toxins share a strikingly similar three-domain structure, despite considerable variation among them in amino acid sequence and specificity.

As reported in U.S. Pat. Nos. 7,105,332, and 7,462,760, the toxicity of Cry proteins can be improved by targeting the region located between alpha helices 3 and 4 of domain 1 of the toxin. This theory was premised on a body of knowledge concerning insecticidal toxins, including: 1) that alpha helices 4 and 5 of domain 1 of Cry3A toxins had been reported to insert into the lipid bilayer of cells lining the midgut of susceptible insects (Gazit et al. (1998) *Proc. Natl. Acad. Sci. USA* 95: 12289-12294); 2) the inventors' knowledge of the location of trypsin and chymotrypsin cleavage sites within the amino acid sequence of the wild-type protein; 3) the observation that the wild-type protein was more active against certain insects following in vitro activation by trypsin or chymotrypsin treatment; and 4) reports that digestion of toxins from the 3' end resulted in decreased toxicity to insects.

A series of mutations may be created and placed in a variety of background sequences to create novel polypeptides having enhanced or altered pesticidal activity. See, e.g., U.S. Pat. No. 7,462,760. These mutants include, but are not limited to: the addition of at least one more protease-sensitive site (e.g., trypsin cleavage site) in the region located between helices 3 and 4 of domain 1; the replacement of an original protease-sensitive site in the wild-type sequence with a different protease-sensitive site; the addition of multiple protease-sensitive sites in a particular location; the addition of amino acid residues near protease-sensitive site(s) to alter folding of the polypeptide and thus enhance digestion of the polypeptide at the protease-sensitive site(s); and adding mutations to protect the polypeptide from degradative digestion that reduces toxicity (e.g., making a series of mutations wherein the wild-type amino acid is replaced by valine to protect the polypeptide from digestion). Mutations may be used singly or in any combination to provide polypeptides of the embodiments.

In this manner, the embodiments provide sequences comprising a variety of mutations, such as, for example, a mutation that comprises an additional, or an alternative, protease-sensitive site located between alpha-helices 3 and 4 of domain 1 of the encoded polypeptide.

A mutation which is an additional or alternative protease-sensitive site may be sensitive to several classes of proteases such as serine proteases, which include trypsin and chymotrypsin, or enzymes such as elastase. Thus, a mutation which is an additional or alternative protease-sensitive site may be designed so that the site is readily recognized and/or cleaved by a category of proteases, such as mammalian proteases or insect proteases. A protease-sensitive site may also be designed to be cleaved by a particular class of enzymes or a particular enzyme known to be produced in an organism, such as, for example, a chymotrypsin produced by the corn earworm *Heliothis zea* (Lenz et al. (1991) *Arch. Insect Biochem.* Physiol. 16: 201-212). Mutations may also confer resistance to proteolytic digestion, for example, to digestion by chymotrypsin at the C-terminus of the peptide.

The presence of an additional and/or alternative protease-sensitive site in the amino acid sequence of the encoded polypeptide can improve the pesticidal activity and/or specificity of the polypeptide encoded by the nucleic acids of the embodiments. Accordingly, the nucleotide sequences of the embodiments can be recombinantly engineered or manipulated to produce polypeptides having improved or altered insecticidal activity and/or specificity compared to that of an unmodified wild-type toxin. In addition, the mutations disclosed herein may be placed in or used in conjunction with other nucleotide sequences to provide improved properties. For example, a protease-sensitive site that is readily cleaved by insect chymotrypsin, e.g. a chymotrypsin found in the bertha armyworm or the corn earworm (Hegedus et al. (2003) *Arch. Insect Biochem. Physiol.* 53: 30-47; and Lenz et al. (1991) *Arch. Insect Biochem. Physiol.* 16: 201-212), may be placed in a Cry background sequence to provide improved toxicity to that sequence. In this manner, the embodiments provide toxic polypeptides with improved properties.

For example, a mutagenized Cry nucleotide sequence can comprise additional mutants that comprise additional codons that introduce a second trypsin-sensitive amino acid sequence (in addition to the naturally occurring trypsin site) into the encoded polypeptide. An alternative addition mutant of the embodiments comprises additional codons designed to introduce at least one additional different protease-sensitive site into the polypeptide; for example, a chymotrypsin-sensitive site located immediately 5' or 3' of the naturally occurring trypsin site. Alternatively, substitution mutants may be created in which at least one codon of the nucleic acid that encodes the naturally occurring protease-sensitive site is destroyed and alternative codons are introduced into the nucleic acid sequence in order to provide a different (e.g., substitute) protease-sensitive site. A replacement mutant may also be added to a Cry sequence in which the naturally-occurring trypsin cleavage site present in the encoded polypeptide is destroyed and a chymotrypsin or elastase cleavage site is introduced in its place.

It is recognized that any nucleotide sequence encoding the amino acid sequences that are proteolytic sites or putative proteolytic sites (for example, sequences such as RR, or LKM) can be used and that the exact identity of the codons used to introduce any of these cleavage sites into a variant polypeptide may vary depending on the use, i.e., expression in a particular plant species. It is also recognized that any of the disclosed mutations can be introduced into any polynucleotide sequence of the embodiments that comprises the codons for amino acid residues that provide the native trypsin cleavage site that is targeted for modification. Accordingly, variants of either full-length toxins or fragments thereof can be modified to contain additional or alternative cleavage sites, and these embodiments are intended to be encompassed by the scope of the embodiments disclosed herein.

It will be appreciated by those of skill in the art that any useful mutation may be added to the sequences of the embodiments so long as the encoded polypeptides retain pesticidal activity. Thus, sequences may also be mutated so that the encoded polypeptides are resistant to proteolytic digestion by chymotrypsin. More than one recognition site can be added in a particular location in any combination, and multiple recognition sites can be added to or removed from the toxin. Thus, additional mutations can comprise three, four, or more recognition sites. It is to be recognized that multiple mutations can be engineered in any suitable polynucleotide sequence; accordingly, either full-length sequences or fragments thereof can be modified to contain additional or alternative cleavage sites as well as to be resistant to proteolytic digestion. In this manner, the embodiments provide Cry toxins containing mutations that improve pesticidal activity as well as improved compositions and methods for impacting pests using other Bt toxins.

Mutations may protect the polypeptide from protease degradation, for example by removing putative proteolytic sites such as putative serine protease sites and elastase recognition sites from different areas. Some or all of such putative sites may be removed or altered so that proteolysis at the location of the original site is decreased. Changes in proteolysis may be assessed by comparing a mutant polypeptide with wild-type toxins or by comparing mutant toxins which differ in their amino acid sequence. Putative proteolytic sites and proteolytic sites include, but are not limited to, the following sequences: RR, a trypsin cleavage site; LKM, a chymotrypsin site; and a trypsin site. These sites may be altered by the addition or deletion of any number and kind of amino acid residues, so long as the pesticidal activity of the polypeptide is increased. Thus, polypeptides encoded by nucleotide sequences comprising mutations will comprise at least one amino acid change or addition relative to the native or background sequence, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 38, 40, 45, 47, 50, 60, 70, 80, 90, 100, 110, 120, 130, 140, 150, 160, 170, 180, 190, 200, 210, 220, 230, 240, 250, 260, 270, or 280 or more amino acid changes or additions. Pesticidal activity of a polypeptide may also be improved by truncation of the native or full-length sequence, as is known in the art.

Compositions of the embodiments include nucleic acids, and fragments and variants thereof that encode pesticidal polypeptides. In particular, the embodiments provide for isolated nucleic acid molecules comprising nucleotide sequences encoding the amino acid sequence shown in SEQ ID NO: 2, or the nucleotide sequences encoding said amino acid sequence, for example the nucleotide sequence set forth in SEQ ID NO: 4, and fragments and variants thereof.

Also of interest are optimized nucleotide sequences encoding the pesticidal proteins of the embodiments. As used herein, the phrase "optimized nucleotide sequences" refers to nucleic acids that are optimized for expression in a particular organism, for example a plant. Optimized nucleotide sequences may be prepared for any organism of interest using methods known in the art. See, for example, U.S. Pat. No. 7,462,760, which describes an optimized nucleotide sequence encoding a disclosed pesticidal protein. In this example, the nucleotide sequence was prepared by reverse-translating the amino acid sequence of the protein and changing the nucleotide sequence so as to comprise maize-preferred codons while still encoding the same amino acid sequence. This procedure is described in more detail by Murray et al. (1989) *Nucleic Acids Res.* 17:477-498. Optimized nucleotide sequences find use in increasing expression of a pesticidal protein in a plant, for example monocot plants of the Gramineae (Poaceae) family such as, for example, a maize or corn plant.

The disclosure provides polynucleotides encoding polypeptides comprising an amino acid sequence having least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to SEQ ID NO: 2. The disclosure provides polynucleotides encoding polypeptides comprising an amino acid sequence having least 95% identity to SEQ ID NO: 2.

The disclosure provides polynucleotides encoding polypeptides comprising an amino acid sequence having least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to SEQ ID NO: 4.

In some embodiments the polypeptide comprises an amino acid sequence having least 95% identity to SEQ ID NO: 4.

In some embodiments the polypeptide comprises an amino acid sequence having least 95% identity to the full length of SEQ ID NO: 4.

The embodiments further provide isolated pesticidal (e.g., insecticidal) polypeptides encoded by either a naturally-occurring or modified nucleic acid of the embodiments. More specifically, the embodiments provide polypeptides comprising an amino acid sequence set forth in SEQ ID NO: 2 and SEQ ID NO: 4, and the polypeptides encoded by nucleic acids described herein, for example those set forth in SEQ ID NO: 1 and SEQ ID NO: 3, and fragments and variants thereof.

In particular embodiments, pesticidal proteins of the embodiments provide full-length insecticidal polypeptides, fragments of full-length insecticidal polypeptides, and variant polypeptides that are produced from mutagenized nucleic acids designed to introduce particular amino acid sequences into polypeptides of the embodiments. In particular embodiments, the amino acid sequences that are introduced into the polypeptides comprise a sequence that provides a cleavage site for an enzyme such as a protease.

It is known in the art that the pesticidal activity of Bt toxins is typically activated by cleavage of the peptide in the insect gut by various proteases. Because peptides may not always be cleaved with complete efficiency in the insect gut, fragments of a full-length toxin may have enhanced pesticidal activity in comparison to the full-length toxin itself. Thus, some of the polypeptides of the embodiments include fragments of a full-length insecticidal polypeptide, and some of the polypeptide fragments, variants, and mutations will have enhanced pesticidal activity relative to the activity of the naturally occurring insecticidal polypeptide from which they are derived, particularly if the naturally occurring insecticidal polypeptide is not activated in vitro with a protease prior to screening for activity. Thus, the present application encompasses truncated versions or fragments of the sequences.

Mutations may be placed into any background sequence, including such truncated polypeptides, so long as the polypeptide retains pesticidal activity. One of skill in the art can readily compare two or more proteins with regard to pesticidal activity using assays known in the art or described elsewhere herein. It is to be understood that the polypeptides of the embodiments can be produced either by expression of a nucleic acid disclosed herein, or by the use of standard molecular biology techniques.

It is recognized that the pesticidal proteins may be oligomeric and will vary in molecular weight, number of residues, component peptides, activity against particular pests, and other characteristics. However, by the methods set forth herein, proteins active against a variety of pests may be isolated and characterized. The pesticidal proteins of the embodiments can be used in combination with other Bt toxins or other insecticidal proteins to increase insect target range. Furthermore, the use of the pesticidal proteins of the embodiments in combination with other Bt toxins or other insecticidal principles of a distinct nature has particular utility for the prevention and/or management of insect resistance. Other insecticidal agents include protease inhibitors (both serine and cysteine types), α-amylase, and peroxidase.

Fragments and variants of the nucleotide and amino acid sequences and the polypeptides encoded thereby are also encompassed by the embodiments. As used herein the term "fragment" refers to a portion of a nucleotide sequence of a polynucleotide or a portion of an amino acid sequence of a polypeptide of the embodiments. Fragments of a nucleotide sequence may encode protein fragments that retain the biological activity of the native or corresponding full-length protein and hence possess pesticidal activity. Thus, it is acknowledged that some of the polynucleotide and amino acid sequences of the embodiments can correctly be referred to as both fragments and mutants.

It is to be understood that the term "fragment," as it is used to refer to nucleic acid sequences of the embodiments, also encompasses sequences that are useful as hybridization probes. This class of nucleotide sequences generally does not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the embodiments.

A fragment of a nucleotide sequence of the embodiments that encodes a biologically active portion of a pesticidal protein of the embodiments will encode at least 15, 25, 30, 50, 100, 200, 250, 300, 350, 400, 450, 500, 550, 600, 650 contiguous amino acids, or up to the total number of amino acids present in a pesticidal polypeptide of the embodiments (for example, 693 amino acids for SEQ ID NO: 4). Fragments of a nucleotide sequence of the embodiments that are useful as hybridization probes or PCR primers generally need not encode a biologically active portion of a pesticidal protein. Thus, a fragment of a nucleic acid of the embodiments may encode a biologically active portion of a pesticidal protein, or it may be a fragment that can be used as a hybridization probe or PCR primer using methods disclosed herein. A biologically active portion of a pesticidal protein can be prepared by isolating a portion of one of the nucleotide sequences of the embodiments, expressing the encoded portion of the pesticidal protein (e.g., by recombinant expression in vitro), and assessing the activity of the encoded portion of the pesticidal protein.

Particular embodiments envision fragments derived from (e.g., produced from) a first nucleic acid of the embodiments, wherein the fragment encodes a truncated toxin characterized by pesticidal activity. Truncated polypeptides encoded by the polynucleotide fragments of the embodiments are characterized by pesticidal activity that is either equivalent to, or improved, relative to the activity of the corresponding full-length polypeptide encoded by the first nucleic acid from which the fragment is derived. It is envisioned that such nucleic acid fragments of the embodiments may be truncated at the 3' end of the native or corresponding full-length coding sequence. Nucleic acid fragments may also be truncated at both the 5' and 3' end of the native or corresponding full-length coding sequence.

The term "variants" is used herein to refer to substantially similar sequences. For nucleotide sequences, conservative variants include those sequences that, because of the degeneracy of the genetic code, encode the amino acid sequence of one of the pesticidal polypeptides of the embodiments. Those having ordinary skill in the art will readily appreciate that due to the degeneracy of the genetic code, a multitude of nucleotide sequences encoding of the present disclosure exist.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray, et al., supra. Methods are available in the art for synthesizing plant-preferred genes. See, for example, U.S. Pat. Nos. 5,380,831, and 5,436,391 and Murray, et al., (1989) *Nucleic Acids Res.* 17:477-498, and Liu H et al. *Mol Bio Rep* 37:677-684, 2010, herein incorporated by reference. A *Zea* maize codon usage table can be also found at kazusa.or.jp/codon/cgi-bin/showcodon.cgi?species=4577, which can be accessed using the www prefix. A maize optimal codon analysis (adapted from Liu H et al. *Mol Bio Rep* 37:677-684, 2010).

A *Glycine max* codon usage table is shown in Table 3 and can also be found at kazusa.or.jp/codon/cgi-bin/showcodon.cgi?species=3847&aa=1&style=N, which can be accessed using the www prefix.

The skilled artisan will further appreciate that changes can be introduced by mutation of the nucleic acid sequences thereby leading to changes in the amino acid sequence of the encoded polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Naturally occurring allelic variants such as these can be identified with the use of well-known molecular biology techniques, such as, for example, polymerase chain reaction (PCR) and hybridization techniques as outlined herein.

Variant nucleotide sequences also include synthetically derived nucleotide sequences, such as those generated, for example, by using site-directed mutagenesis but which still encode a pesticidal protein of the embodiments, such as a mutant toxin. Generally, variants of a particular nucleotide sequence of the embodiments will have at least about 70%, 75%, 80%, 85%, 86%, 87%, 88%, 89%, 90%, 91%, 92%, 93%, 94%, 95%, 96%, 97%, 98%, 99%, or more sequence identity to that particular nucleotide sequence as determined by sequence alignment programs described elsewhere herein using default parameters. A variant of a nucleotide sequence of the embodiments may differ from that sequence by as few as 1-15 nucleotides, as few as 1-10, such as 6-10, as few as 5, as few as 4, 3, 2, or even 1 nucleotide.

Variants of a particular nucleotide sequence of the embodiments (i.e., an exemplary nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptide of SEQ ID NO: 2 or SEQ ID NO: 4 are disclosed. Percent sequence identity between any two polypeptides can be calculated using sequence alignment programs described elsewhere herein using default parameters. Where any given pair of polynucleotides of the embodiments is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, at least about 90%, 91%, 92%, 93%, 94%, 95%, 96%, 97%, or at least about 98%, 99% or more sequence identity.

As used herein, the term "variant protein" encompasses polypeptides that are derived from a native protein by: deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Accordingly, the term "variant protein" encompasses biologically active fragments of a native protein that comprise a sufficient number of contiguous amino acid residues to retain the biological activity of the native protein, i.e., to have pesticidal activity. Such pesticidal activity may be different or improved relative to the native protein or it may be unchanged, so long as pesticidal activity is retained.

Variant proteins encompassed by the embodiments are biologically active, that is they continue to possess the desired biological activity of the native protein, that is, pesticidal activity as described herein. Such variants may result from, for example, genetic polymorphism or from human manipulation. Biologically active variants of a native pesticidal protein of the embodiments will have at least about 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence for the native protein as determined by sequence alignment programs described elsewhere herein using default parameters. A biologically active variant of a protein of the embodiments may differ from that protein by 1-35, 1-30, 1-25, 1-20, 1-15, 1-10, as few as 5, as few as 4, 3, 2, or even 1 amino acid residue.

In some embodiments the polypeptide comprises an amino acid sequence having least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to SEQ ID NO: 2.

In some embodiments the polypeptide comprises an amino acid sequence having least 95% identity to SEQ ID NO: 2.

In some embodiments the polypeptide comprises an amino acid sequence having least 95% identity to the full length of SEQ ID NO: 2.

In some embodiments the polypeptide comprises an amino acid sequence having least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to SEQ ID NO: 4.

In some embodiments the polypeptide comprises an amino acid sequence having least 95% identity to SEQ ID NO: 4.

In some embodiments the polypeptide comprises an amino acid sequence having least 95% identity to the full length of SEQ ID NO: 4.

In some embodiments the polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, but are not limited to solubility, folding, stability, and digestibility. In some embodiments the polypeptide has increased digestibility of proteolytic fragments in an insect gut. Models for digestion by simulated simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al J. Agric Food Chem. 50: 7154-7160, 2002).

The embodiments further encompass a microorganism that is transformed with at least one nucleic acid of the embodiments, with an expression cassette comprising the nucleic acid, or with a vector comprising the expression cassette. In some embodiments, the microorganism is one that multiplies on plants. An embodiment of the disclosure relates to an encapsulated pesticidal protein which comprises a transformed microorganism capable of expressing at least one pesticidal protein of the embodiments.

The embodiments provide pesticidal compositions comprising a transformed microorganism of the embodiments. In such embodiments, the transformed microorganism is generally present in the pesticidal composition in a pesticidally effective amount, together with a suitable carrier. The embodiments also encompass pesticidal compositions comprising an isolated protein of the embodiments, alone or in combination with a transformed organism of the embodiments and/or an encapsulated pesticidal protein of the embodiments, in an insecticidally effective amount, together with a suitable carrier.

The embodiments further provide a method of increasing insect target range by using a pesticidal protein of the embodiments in combination with at least one other or "second" pesticidal protein. Any pesticidal protein known in the art can be employed in the methods of the embodiments. Such pesticidal proteins include, but are not limited to, Bt toxins, protease inhibitors, α-amylases, and peroxidases.

The embodiments also encompass transformed or transgenic plants comprising at least one nucleotide sequence of the embodiments. In some embodiments, the plant is stably transformed with a nucleotide construct comprising at least one nucleotide sequence of the embodiments operably linked to a promoter that drives expression in a plant cell. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette.

It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes whole plants, plant organs (e.g., leaves, stems, roots, etc.), seeds, plant cells, and progeny of same. Parts of transgenic plants are within the scope of the embodiments and comprise, for example, plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, originating in transgenic plants or their progeny previously transformed with a DNA molecule of the embodiments and therefore consisting at least in part of transgenic cells. The class of plants that can be used in the methods of the embodiments is generally as broad as the class of higher plants amenable to transformation techniques, including both monocotyledonous and dicotyledonous plants.

While the embodiments do not depend on a particular biological mechanism for increasing the resistance of a plant to a plant pest, expression of the nucleotide sequences of the embodiments in a plant can result in the production of the pesticidal proteins of the embodiments and in an increase in the resistance of the plant to a plant pest. The plants of the embodiments find use in agriculture in methods for impacting insect pests. Certain embodiments provide transformed crop plants, such as, for example, maize plants, which find use in methods for impacting insect pests of the plant, such as, for example, Lepidopteran pests.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

One of skill in the art will readily acknowledge that advances in the field of molecular biology such as site-specific and random mutagenesis, polymerase chain reaction methodologies, and protein engineering techniques provide an extensive collection of tools and protocols suitable for use to alter or engineer both the amino acid sequence and underlying genetic sequences of proteins of agricultural interest.

Thus, the proteins of the embodiments may be altered in various ways including amino acid substitutions, deletions, truncations, and insertions. Methods for such manipulations are generally known in the art. For example, amino acid sequence variants of the pesticidal proteins can be prepared by introducing mutations into a synthetic nucleic acid (e.g., DNA molecule). Methods for mutagenesis and nucleic acid alterations are well known in the art. For example, designed changes can be introduced using an oligonucleotide-mediated site-directed mutagenesis technique. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York), and the references cited therein.

The mutagenized nucleotide sequences of the embodiments may be modified so as to change about 1, 2, 3, 4, 5, 6, 8, 10, 12 or more of the amino acids present in the primary sequence of the encoded polypeptide. Alternatively, even more changes from the native sequence may be introduced such that the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more of the codons altered, or otherwise modified compared to the corresponding wild-type protein. In the same manner, the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more additional codons compared to the corresponding wild-type protein. It should be understood that the mutagenized nucleotide sequences of the embodiments are intended to encompass biologically functional, equivalent peptides which have pesticidal activity, such as an improved pesticidal activity as determined by antifeedant properties against European corn borer larvae. Such sequences may arise as a consequence of codon redundancy and functional equivalency that are known to occur naturally within nucleic acid sequences and the proteins thus encoded.

One of skill in the art would recognize that amino acid additions and/or substitutions are generally based on the relative similarity of the amino acid side-chain substituents, for example, their hydrophobicity, charge, size, and the like. Exemplary amino acid substitution groups that take several of the foregoing characteristics into consideration are well known to those of skill in the art and include: arginine and lysine; glutamate and aspartate; serine and threonine; glutamine and asparagine; and valine, leucine, and isoleucine.

Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the genes and nucleotide sequences of the embodiments include both the naturally occurring sequences and mutant forms. Likewise, the proteins of the embodiments encompass both naturally occurring proteins and variations (e.g., truncated polypeptides) and modified (e.g., mutant) forms thereof. Such variants will continue to possess the desired pesticidal activity. Obviously, the mutations that will be made in the nucleotide sequence encoding the variant must not place the sequence out of reading frame and generally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays, such as insect-feeding assays. See, for example, Marrone et al (1985) *J. Econ. Entomol.* 78: 290-293 and Czapla and Lang (1990) *J. Econ. Entomol.* 83: 2480-2485, herein incorporated by reference.

Variant nucleotide sequences and proteins also encompass sequences and proteins derived from a mutagenic and recombinogenic procedure such as DNA shuffling. With such a procedure, one or more different coding sequences can be manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, full-length coding sequences, sequence motifs encoding a domain of interest, or any fragment of a nucleotide sequence of the embodiments may be shuffled between the nucleotide sequences of the embodiments and corresponding portions of other known Cry nucleotide sequences to obtain a new gene coding for a protein with an improved property of interest.

Properties of interest include, but are not limited to, pesticidal activity per unit of pesticidal protein, protein stability, and toxicity to non-target species particularly humans, livestock, and plants and microbes that express the pesticidal polypeptides of the embodiments. The embodiments are not bound by a particular shuffling strategy, only that at least one nucleotide sequence of the embodiments, or part thereof, is involved in such a shuffling strategy. Shuffling may involve only nucleotide sequences disclosed herein or may additionally involve shuffling of other nucleotide sequences known in the art. Strategies for DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the embodiments can also be used to isolate corresponding sequences from other organisms, particularly other bacteria, and more particularly other *Bacillus* strains. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.), hereinafter "Sambrook". See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$ or any other detectable marker. Thus, for example, probes for hybridization can be made by labeling synthetic oligonucleotides based on the sequences of the embodiments. Methods for preparation of probes for hybridization and for construction of cDNA and genomic libraries are generally known in the art and are disclosed in Sambrook.

For example, an entire sequence disclosed herein, or one or more portions thereof, may be used as a probe capable of specifically hybridizing to corresponding sequences and messenger RNAs. To achieve specific hybridization under a variety of conditions, such probes include sequences that are unique to the sequences of the embodiments and are generally at least about 10 or 20 nucleotides in length. Such probes may be used to amplify corresponding Cry sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook).

Hybridization of such sequences may be carried out under stringent conditions. The term "stringent conditions" or "stringent hybridization conditions" as used herein refers to conditions under which a probe will hybridize to its target sequence to a detectably greater degree than to other sequences (e.g., at least 2-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least about 20 minutes. Optionally, wash buffers may comprise about 0.1% to about 1% SDS. The duration of hybridization is generally less than about 24 hours, usually about 4 to about 12 hours.

An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See also Sambrook. Thus, isolated sequences that encode a Cry protein of the embodiments and hybridize under stringent conditions to the Cry sequences disclosed herein, or to fragments thereof, are encompassed by the embodiments.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the National Center for Biotechnology Information website on the world wide web at ncbi.hlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. The term "equivalent program" as used herein refers to any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%. 80%, 90%, or 95% or more sequence identity when compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes generally means sequence identity of at least 60%, 70%, 80%, 90%, or 95% or more sequence identity.

The term "substantial identity" in the context of a peptide indicates that a peptide comprises a sequence with at least 70%, 80%, 85%, 90%, 95%, or more sequence identity to a reference sequence over a specified comparison window. Optimal alignment for these purposes can be conducted using the global alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures, and the like.

A further embodiment relates to a transformed organism such as an organism selected from the group consisting of plant and insect cells, bacteria, yeast, baculoviruses, protozoa, nematodes, and algae. The transformed organism comprises: a DNA molecule of the embodiments, an expression cassette comprising the said DNA molecule, or a vector comprising the said expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions are contiguous and in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the Cry toxin sequence to be under the transcriptional regulation of the regulatory regions. The DNA construct may additionally contain selectable marker genes.

The DNA construct will include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

The termination region may be native with the transcriptional initiation region, may be native with the operably linked DNA sequence of interest, may be native with the plant host, or may be derived from another source (i.e., foreign or heterologous to the promoter, the sequence of interest, the plant host, or any combination thereof).

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray et al., supra. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli*, or eukaryotic cells such as yeast, insect, amphibian, or mammalian cells, or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus), human immunoglobulin heavy-chain binding protein (BiP) (Macejak et al (1991) *Nature* 353: 90-94); untranslated leader from the coat protein mRNA of alfalfa mosaic virus (AMV RNA 4) (Jobling et al (1987) *Nature* 325: 622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan (1990) *Ann. Rev. Phytopath.* 28: 425-449; Duan et al. (1996) *Nature Biotechnology* 14: 494-498); wun1 and wun2, U.S. Pat. No. 5,428,148; win1 and win2 (Stanford et al. (1989) *Mol. Gen. Genet.* 215: 200-208); systemin (McGurl et al. (1992) *Science* 225: 1570-1573); WIP1 (Rohmeier et al. (1993) *Plant Mol. Biol.* 22: 783-792; Eckelkamp et al. (1993) *FEBS Letters* 323: 73-76); MPI gene (Corderok et al. (1994) *Plant J.* 6(2): 141-150); and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant PathoL* 89: 245-254; Uknes et al. (1992) *Plant Cell* 4: 645-656; and Van Loon (1985) *Plant Mol. ViroL* 4: 111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced pesticidal protein expression within a particular plant tissue. Tissue-preferred promoters include those discussed in Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred or root-specific promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see Plant Science (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene fused to nptll (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see U.S. Pat. No. 6,225,529, herein incorporated by reference). Gamma-zein and Glob-1 are endosperm-specific promoters. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference. A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 99/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; and Meijer et al. (1991) *Plant Mol. Biol.* 16:807-820); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481; and U.S. Pat. Nos. 7,709,702; and 7,462,481); phosphinothricin (DeBlock et al. (1987) *EMBO J.* 6:2513-2518). See generally, Yarranton (1992) *Curr. Opin. Biotech.* 3: 506-511; Christopherson et al. (1992) *Proc. Natl Acad. Sci. USA* 89: 6314-6318; Yao et al. (1992) *Cell* 71: 63-72; Reznikoff (1992) *Mol. Microbiol.* 6: 2419-2422; Barkley et al. (1980) in *The Operon*, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl Acad. Sci. USA* 86: 5400-5404; Fuerst et al. (1989) *Proc. Natl. Acad. Sci. USA* 86: 2549-2553; Deuschle et al. (1990) *Science* 248: 480-483; Gossen (1993) Ph.D. Thesis, University of Heidelberg; Reines et al. (1993) *Proc. Natl. Acad. Sci. USA* 90: 1917-1921; Labow et al. (1990) *Mol. Cell. Biol.* 10: 3343-3356; Zambretti et al. (1992) *Proc. Natl Acad. Sci. USA* 89: 3952-3956; Bairn et al. (1991) *Proc. Natl Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, *University of Heidelberg*; Gossen et al. (1992) *Proc. Natl Acad. Sci. USA* 89: 5547-5551; Oliva et al. (1992) *Antimicrob. Agents Chemother.* 36: 913-919; Hlavka et al. (1985) *Handbook of Experimental Pharmacology*, Vol. 78 (Springer-Verlag, Berlin); and Gill et al. (1988) *Nature* 334: 721-724. Such disclosures are herein incorporated by reference.

The above list of selectable marker genes is not meant to be limiting. Any selectable marker gene can be used in the embodiments.

The methods of the embodiments involve introducing a polypeptide or polynucleotide into a plant. "Introducing" is intended to mean presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4: 320-334), electroporation (Riggs et al. (1986) *Proc. Natl. Acad. Sci. USA* 83: 5602-5606), *Agrobacterium*-mediated transformation (U.S. Pat. Nos. 5,563,055 and 5,981,840), direct gene transfer (Paszkowski et al. (1984) *EMBO J.* 3: 2717-2722), and ballistic particle acceleration (see, for example, U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6: 923-926); and Lecl transformation (WO 00/28058). For potato transformation see Tu et al. (1998) *Plant Molecular Biology* 37: 829-838 and Chong et al. (2000) *Transgenic Research* 9: 71-78. Additional transformation procedures can be found in Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87: 671-674 (soybean); McCabe et al. (1988) *Bio/Technology* 6: 923-926 (soybean); Finer and McMullen (1991) *In Vitro Cell Dev. Biol.* 27P: 175-182 (soybean); Singh et al. (1998) *Theor. Appl. Genet.* 96: 319-324 (soybean); Datta et al. (1990) *Biotechnology* 8: 736-740 (rice); Klein et al. (1988) *Proc. Natl. Acad. Sci. USA* 85: 4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91: 440-444 (maize); Fromm et al. (1990) *Biotechnology* 8: 833-839 (maize); Hooykaas-Van Slogteren et al. (1984) *Nature* (London) 311: 763-764; U.S. Pat. No. 5,736,369 (cereals); Bytebier et al. (1987) *Proc. Natl. Acad. Sci. USA* 84: 5345-5349 (Liliaceae); De Wet et al (1985) in *The Experimental Manipulation of Ovule Tissues*, ed. Chapman et al. (Longman, N.Y.), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation);

D'Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the Cry toxin protein or variants and fragments thereof directly into the plant or the introduction of the Cry toxin transcript into the plant. Such methods include, for example, microinjection or particle bombardment. See, for example, Crossway et al. (1986) *Mol Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the Cry toxin polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma # P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5: 81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired pesticidal protein. It is also recognized that such a viral polyprotein, comprising at least a portion of the amino acid sequence of a pesticidal protein of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367; and 5,316,931; herein incorporated by reference.

The embodiments further relate to plant-propagating material of a transformed plant of the embodiments including, but not limited to, seeds, tubers, corms, bulbs, leaves, and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *Brassica napus, Brassica rapa, Brassica juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*Cucumis sativus*), cantaloupe (*Cucumis cantalupensis*), and musk melon (*Cucumis melo*). Ornamentals include azalea (*Rhododendron* spp.), hydrangea (*Macrophylla hydrangea*), hibiscus (Hibiscus rosasanensis), roses (Rosa spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the embodiments include, for example, pines such as loblolly pine (*Pinus taeda*), slash pine (*Pinus ellioth*), *ponderosa* pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true first such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants, including, but not limited to: corn, alfalfa, sunflower, *Brassica* spp., soybean, cotton, safflower, peanut, sorghum, wheat, millet, tobacco, sugarcane, etc.

Turfgrasses include, but are not limited to: annual bluegrass (*Poa annua*); annual ryegrass (*Lolium multiflorum*); Canada bluegrass (*Poa compressa*); Chewings fescue (*Festuca rubra); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mung bean, lima bean, fava bean, lentils, chickpea, etc.

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments the polynucleotides encoding the insecticidal polypeptide disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

In some embodiments the stacked trait may be a trait or event that has received regulatory approval including but not limited to the events found at the Center for Environmental Risk Assessment (cera-gmc.org/?action=gm_crop_database, which can be accessed using the www prefix) and at the International Service for the Acquisition of Agri-Biotech Applications isaaa.org/gmapprovaldatabase/default.asp, which can be accessed using the www prefix).

In some embodiments the polynucleotides encoding the insecticidal polypeptide disclosed herein may be stacked with genes encoding pesticidal proteins including but are not limited to: insecticidal proteins from *Pseudomonas* sp. such as PSEEN3174 (Monalysin, (2011) PLoS Pathogens, 7:1-13), from Pseudomonas protegens strain CHAO and Pf-5 (previously fluorescens) (Pechy-Tarr, (2008) Environmental Microbiology 10:2368-2386: GenBank Accession No. EU400157); from Pseudomonas Taiwanensis (Liu, et al., (2010) J. Agric. Food Chem. 58:12343-12349) and from Pseudomonas pseudoalcligenes (Zhang, et al., (2009) Annals of Microbiology 59:45-50 and Li, et al., (2007) Plant Cell Tiss. Organ Cult. 89:159-168); insecticidal proteins from Photorhabdus sp. and Xenorhabdus sp. (Hinchliffe, et al., (2010) The Open Toxinology Journal 3:101-118 and Morgan, et al., (2001) Applied and Envir. Micro. 67:2062-2069), U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of US Patent Publication US20140274885 and; a PIP-47 polypeptide of PCT Publication WO 2015/023846, a PIP-72 polypeptide of WO2015/038734; a PtIP-83 polypeptide of WO 2015/120276, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35,Cry36, Cry37, Cry38, Cry39, Cry40, Cry41, Cry42, Cry43, Cry44, Cry45, Cry 46, Cry47, Cry49, Cry50, Cry51, Cry52, Cry53, Cry 54, Cry55, Cry56, Cry57, Cry58, Cry59, Cry60, Cry61, Cry62, Cry63, Cry64, Cry65, Cry66, Cry67, Cry68, Cry69, Cry70, Cry71, Cry72, Cry73, and Cry74 classes of δ-endotoxin genes and the *Bacillus thuringiensis* cytolytic Cyt1 and Cyt2 genes. Members of these classes of *Bacillus thuringiensis* insecticidal proteins well known to one skilled in the art (see, Crickmore, et al., "*Bacillus thuringiensis* toxin nomenclature" (2011), at lifesci.sussex.ac.uk/home/Neil Crickmore/Bt/toxins2.html which can be accessed on the world-wide web using the "www" prefix). Members of these classes of *Bacillus thuringiensis* insecticidal proteins include, but are not limited to Cry1Aa1 (Accession # AAA22353); Cry1Aa2 (Accession # Accession # AAA22552); Cry1Aa3 (Accession # BAA00257); Cry1Aa4 (Accession # CAA31886); Cry1Aa5 (Accession # BAA04468); Cry1Aa6 (Accession # AAA86265); Cry1Aa7 (Accession # AAD46139); Cry1Aa8 (Accession #126149); Cry1Aa9 (Accession # BAA77213); Cry1Aa10 (Accession # AAD55382); Cry1Aa11 (Accession # CAA70856); Cry1Aa12 (Accession # AAP80146); Cry1Aa13 (Accession # AAM44305); Cry1Aa14 (Accession # AAP40639); Cry1Aa15 (Accession # AAY66993); Cry1Aa16 (Accession # H0439776); Cry1Aa17 (Accession # H0439788); Cry1Aa18 (Accession # H0439790); Cry1Aa19 (Accession # H0685121); Cry1Aa20 (Accession # JF340156); Cry1Aa21 (Accession # JN651496); Cry1Aa22 (Accession # KC158223); Cry1Ab1 (Accession # AAA22330); Cry1Ab2 (Accession # AAA22613); Cry1Ab3 (Accession # AAA22561); Cry1Ab4 (Accession # BAA00071); Cry1Ab5 (Accession # CAA28405); Cry1Ab6 (Accession # AAA22420); Cry1Ab7 (Accession # CAA31620); Cry1Ab8 (Accession # AAA22551); Cry1Ab9 (Accession # CAA38701); Cry1Ab10 (Accession # A29125); Cry1Ab11 (Accession #112419); Cry1Ab12 (Accession # AAC64003); Cry1Ab13 (Accession # AAN76494); Cry1Ab14 (Accession # AAG16877); Cry1Ab15 (Accession # AA013302); Cry1Ab16 (Accession # AAK55546); Cry1Ab17 (Accession # AAT46415); Cry1Ab18 (Accession # AAQ88259); Cry1Ab19 (Accession # AAW31761); Cry1Ab20 (Accession # ABB72460); Cry1Ab21 (Accession # ABS18384); Cry1Ab22 (Accession # ABW87320); Cry1Ab23 (Accession # H0439777); Cry1Ab24 (Accession # H0439778); Cry1Ab25 (Accession # H0685122); Cry1Ab26 (Accession # H0847729); Cry1Ab27 (Accession # JN135249); Cry1Ab28 (Accession # JN135250); Cry1Ab29 (Accession # JN135251); Cry1Ab30 (Accession # JN135252); Cry1Ab31 (Accession # JN135253); Cry1Ab32 (Accession # JN135254); Cry1Ab33 (Accession # AAS93798); Cry1Ab34 (Accession # KC156668); Cry1Ab-like (Accession # AAK14336); Cry1Ab-like (Accession # AAK14337); Cry1Ab-like (Accession # AAK14338); Cry1Ab-like (Accession # ABG88858); Cry1Ac1 (Accession # AAA22331); Cry1Ac2 (Accession # AAA22338); Cry1Ac3 (Accession # CAA38098); Cry1Ac4 (Accession # AAA73077); Cry1Ac5 (Accession # AAA22339); Cry1Ac6 (Accession # AAA86266); Cry1Ac7 (Accession # AAB46989); Cry1Ac8 (Accession # AAC44841); Cry1Ac9 (Accession # AAB49768); Cry1Ac10 (Accession # CAA05505); Cry1Ac11 (Accession # CAA10270); Cry1Ac12 (Accession #112418); Cry1Ac13 (Accession # AAD38701); Cry1Ac14 (Accession # AAQ06607); Cry1Ac15 (Accession # AAN07788); Cry1Ac16 (Accession # AAU87037); Cry1Ac17 (Accession # AAX18704); Cry1Ac18 (Accession # AAY88347); Cry1Ac19 (Accession # ABD37053); Cry1Ac20 (Accession # ABB89046); Cry1Ac21 (Accession # AAY66992); Cry1Ac22 (Accession # ABZ01836); Cry1Ac23 (Accession # CA030431); Cry1Ac24 (Accession # ABL01535); Cry1Ac25 (Accession # FJ513324); Cry1Ac26 (Accession # FJ617446); Cry1Ac27 (Accession # FJ617447); Cry1Ac28 (Accession # ACM90319); Cry1Ac29 (Accession # D0438941); Cry1Ac30 (Accession # G0227507); Cry1Ac31 (Accession # GU446674); Cry1Ac32 (Accession # HM061081); Cry1Ac33 (Accession # G0866913); Cry1Ac34 (Accession # H0230364); Cry1Ac35 (Accession # JF340157); Cry1Ac36 (Accession # JN387137); Cry1Ac37 (Accession # JQ317685); Cry1Ad1 (Accession # AAA22340); Cry1Ad2 (Accession # CAA01880); Cry1Ae1 (Accession # AAA22410); Cry1Af1 (Accession # AAB82749); Cry1Ag1 (Accession # AAD46137); Cry1Ah1 (Accession # AAQ14326); Cry1Ah2 (Accession # ABB76664); Cry1Ah3 (Accession # H0439779); Cry1Ai1 (Accession # AA039719); Cry1Ai2 (Accession # H0439780); Cry1A-like (Accession # AAK14339); Cry1Ba1 (Accession # CAA29898); Cry1Ba2 (Accession # CAA65003); Cry1Ba3 (Accession # AAK63251); Cry1Ba4 (Accession # AAK51084); Cry1Ba5 (Accession # AB020894); Cry1Ba6 (Accession # ABL60921); Cry1Ba7 (Accession # H0439781); Cry1Bb1 (Accession # AAA22344); Cry1Bb2 (Accession # H0439782); Cry1 Bc1 (Accession # CAA86568); Cry1 Bd1 (Accession # AAD10292); Cry1Bd2 (Accession # AAM93496); Cry1Be1 (Accession # AAC32850); Cry1Be2 (Accession # AAQ52387); Cry1 Be3 (Accession # ACV96720); Cry1 Be4 (Accession # HM070026); Cry1Bf1 (Accession # CAC50778); Cry1 Bf2 (Accession # AAQ52380); Cry1 Bg1 (Accession # AA039720); Cry1Bh1 (Accession # H0589331); Cry1Bi1 (Accession # KC156700); Cry1Ca1 (Accession # CAA30396); Cry1Ca2 (Accession # CAA31951); Cry1Ca3 (Accession # AAA22343); Cry1Ca4 (Accession # CAA01886); Cry1Ca5 (Accession # CAA65457); Cry1Ca6 [1] (Accession # AAF37224); Cry1Ca7 (Accession # AAG50438); Cry1Ca8 (Accession # AAM00264); Cry1Ca9 (Accession # AAL79362); Cry1Ca10 (Accession # AAN16462); Cry1Ca11 (Accession # AAX53094); Cry1Ca12 (Accession # HM070027); Cry1Ca13 (Accession # H0412621); Cry1Ca14 (Accession # JN651493); Cry1Cb1 (Accession # M97880); Cry1Cb2 (Accession # AAG35409); Cry1Cb3 (Accession # ACD50894); Cry1Cb-like (Accession # AAX63901); Cry1Da1 (Accession # CAA38099); Cry1Da2 (Accession #176415); Cry1Da3 (Accession # H0439784); Cry1Db1 (Accession # CAA80234); Cry1Db2 (Accession # AAK48937); Cry1 Dc1 (Accession # ABK35074); Cry1 Ea1 (Accession # CAA37933); Cry1 Ea2 (Accession # CAA39609); Cry1 Ea3 (Accession # AAA22345); Cry1 Ea4 (Accession # AAD04732); Cry1Ea5 (Accession # A15535); Cry1Ea6 (Accession # AAL50330); Cry1 Ea7 (Accession # AAW72936); Cry1 Ea8 (Accession # ABX11258); Cry1 Ea9 (Accession # H0439785); Cry1Ea10 (Accession # ADR00398); Cry1Ea11 (Accession # JQ652456); Cry1 Eb1 (Accession # AAA22346); Cry1Fa1 (Accession # AAA22348); Cry1Fa2 (Accession # AAA22347); Cry1Fa3 (Accession # HM070028); Cry1Fa4 (Accession # HM439638); Cry1Fb1 (Accession # CAA80235); Cry1Fb2 (Accession # BAA25298); Cry1Fb3 (Accession # AAF21767); Cry1Fb4 (Accession # AAC10641); Cry1Fb5 (Accession # AA013295); Cry1Fb6 (Accession # ACD50892); Cry1Fb7 (Accession # ACD50893); Cry1Ga1 (Accession # CAA80233); Cry1Ga2 (Accession # CAA70506); Cry1Gb1 (Accession # AAD10291); Cry1Gb2 (Accession # AA013756); Cry1Gc1 (Accession # AAQ52381); Cry1Ha1 (Accession # CAA80236); Cry1 Hb1 (Accession # AAA79694); Cry1 Hb2 (Accession # H0439786); Cry1H-like (Accession # AAF01213); Cry1 Ia1 (Accession # CAA44633); Cry1 Ia2 (Accession # AAA22354); Cry1Ia3 (Accession # AAC36999); Cry1Ia4 (Accession # AAB00958); Cry1Ia5 (Accession # CAA70124); Cry1Ia6 (Accession # AAC26910); Cry1Ia7 (Accession # AAM73516); Cry1Ia8 (Accession # AAK66742); Cry1Ia9 (Accession # AAQ08616); Cry1Ia10 (Accession # AAP86782); Cry1Ia11 (Accession #

CAC85964); Cry1Ia12 (Accession # AAV53390); Cry1Ia13 (Accession # ABF83202); Cry1Ia14 (Accession # ACG63871); Cry1Ia15 (Accession # FJ617445); Cry1Ia16 (Accession # FJ617448); Cry1Ia17 (Accession # GU989199); Cry1Ia18 (Accession # ADK23801); Cry1Ia19 (Accession # HO439787); Cry1Ia20 (Accession # JQ228426); Cry1Ia21 (Accession # JQ228424); Cry1Ia22 (Accession # JQ228427); Cry1Ia23 (Accession # JQ228428); Cry1Ia24 (Accession # JQ228429); Cry1Ia25 (Accession # JQ228430); Cry1Ia26 (Accession # JQ228431); Cry1Ia27 (Accession # JQ228432); Cry1Ia28 (Accession # JQ228433); Cry1Ia29 (Accession # JQ228434); Cry1Ia30 (Accession # JQ317686); Cry1Ia31 (Accession # JX944038); Cry1Ia32 (Accession # JX944039); Cry1Ia33 (Accession # JX944040); Cry1Ib1 (Accession # AAA82114); Cry1Ib2 (Accession # ABW88019); Cry1Ib3 (Accession # ACD75515); Cry1Ib4 (Accession # HM051227); Cry1Ib5 (Accession # HM070028); Cry1Ib6 (Accession # ADK38579); Cry1Ib7 (Accession # JN571740); Cry1Ib8 (Accession # JN675714); Cry1Ib9 (Accession # JN675715); Cry1Ib10 (Accession # JN675716); Cry1Ib11 (Accession # JQ228423); Cry1Ic1 (Accession # AAC62933); Cry1Ic2 (Accession # AAE71691); Cry1Id1 (Accession # AAD44366); Cry1Id2 (Accession # JQ228422); Cry1Ie1 (Accession # AAG43526); Cry1Ie2 (Accession # HM439636); Cry1Ie3 (Accession # KC156647); Cry1Ie4 (Accession # KC156681); Cry1 If 1 (Accession # AAQ52382); Cry1Ig1 (Accession # KC156701); Cry1 I-like (Accession # AAC31094); Cry1 I-like (Accession # ABG88859); Cry1Ja1 (Accession # AAA22341); Cry1Ja2 (Accession # HM070030); Cry1Ja3 (Accession # JQ228425); Cry1Jb1 (Accession # AAA98959); Cry1Jc1 (Accession # AAC31092); Cry1Jc2 (Accession # AAQ52372); Cry1Jd1 (Accession # CAC50779); Cry1 Ka1 (Accession # AAB00376); Cry1Ka2 (Accession # HO439783); Cry1La1 (Accession # AAS60191); Cry1La2 (Accession # HM070031); Cry1Ma1 (Accession # FJ884067); Cry1Ma2 (Accession # KC156659); Cry1Na1 (Accession # KC156648); Cry1Nb1 (Accession # KC156678); Cry1-like (Accession # AAC31091); Cry2Aa1 (Accession # AAA22335); Cry2Aa2 (Accession # AAA83516); Cry2Aa3 (Accession # D86064); Cry2Aa4 (Accession # AAC04867); Cry2Aa5 (Accession # CAA10671); Cry2Aa6 (Accession # CAA10672); Cry2Aa7 (Accession # CAA10670); Cry2Aa8 (Accession # AAO13734); Cry2Aa9 (Accession # AAO13750); Cry2Aa10 (Accession # AAQ04263); Cry2Aa11 (Accession # AAQ52384); Cry2Aa12 (Accession # AB183671); Cry2Aa13 (Accession # ABL01536); Cry2Aa14 (Accession # ACF04939); Cry2Aa15 (Accession # JN426947); Cry2Ab1 (Accession # AAA22342); Cry2Ab2 (Accession # CAA39075); Cry2Ab3 (Accession # AAG36762); Cry2Ab4 (Accession # AAO13296); Cry2Ab5 (Accession # AAQ04609); Cry2Ab6 (Accession # AAP59457); Cry2Ab7 (Accession # AAZ66347); Cry2Ab8 (Accession # ABC95996); Cry2Ab9 (Accession # ABC74968); Cry2Ab10 (Accession # EF157306); Cry2Ab11 (Accession # CAM84575); Cry2Ab12 (Accession # ABM21764); Cry2Ab13 (Accession # ACG76120); Cry2Ab14 (Accession # ACG76121); Cry2Ab15 (Accession # HM037126); Cry2Ab16 (Accession # GO866914); Cry2Ab17 (Accession # HO439789); Cry2Ab18 (Accession # JN135255); Cry2Ab19 (Accession # JN135256); Cry2Ab20 (Accession # JN135257); Cry2Ab21 (Accession # JN135258); Cry2Ab22 (Accession # JN135259); Cry2Ab23 (Accession # JN135260); Cry2Ab24 (Accession # JN135261); Cry2Ab25 (Accession # JN415485); Cry2Ab26 (Accession # JN426946); Cry2Ab27 (Accession # JN415764); Cry2Ab28 (Accession # JN651494); Cry2Ac1 (Accession # CAA40536); Cry2Ac2 (Accession # AAG35410); Cry2Ac3 (Accession # AAQ52385); Cry2Ac4 (Accession # ABC95997); Cry2Ac5 (Accession # ABC74969); Cry2Ac6 (Accession # ABC74793); Cry2Ac7 (Accession # CAL18690); Cry2Ac8 (Accession # CAM09325); Cry2Ac9 (Accession # CAM09326); Cry2Ac10 (Accession # ABN15104); Cry2Ac11 (Accession # CAM83895); Cry2Ac12 (Accession # CAM83896); Cry2Ad1 (Accession # AAF09583); Cry2Ad2 (Accession # ABC86927); Cry2Ad3 (Accession # CAK29504); Cry2Ad4 (Accession # CAM32331); Cry2Ad5 (Accession # CAO78739); Cry2Ae1 (Accession # AAQ52362); Cry2Af1 (Accession # AB030519); Cry2Af2 (Accession # GO866915); Cry2Ag1 (Accession # ACH91610); Cry2Ah1 (Accession # EU939453); Cry2Ah2 (Accession # ACL80665); Cry2Ah3 (Accession # GU073380); Cry2Ah4 (Accession # KC156702); Cry2Ai1 (Accession # FJ788388); Cry2Aj (Accession #); Cry2Ak1 (Accession # KC156660); Cry2Ba1 (Accession # KC156658); Cry3Aa1 (Accession # AAA22336); Cry3Aa2 (Accession # AAA22541); Cry3Aa3 (Accession # CAA68482); Cry3Aa4 (Accession # AAA22542); Cry3Aa5 (Accession # AAA50255); Cry3Aa6 (Accession # AAC43266); Cry3Aa7 (Accession # CAB41411); Cry3Aa8 (Accession # AAS79487); Cry3Aa9 (Accession # AAW05659); Cry3Aa10 (Accession # AAU29411); Cry3Aa11 (Accession # AAW82872); Cry3Aa12 (Accession # ABY49136); Cry3Ba1 (Accession # CAA34983); Cry3Ba2 (Accession # CAA00645); Cry3Ba3 (Accession # JQ397327); Cry3Bb1 (Accession # AAA22334); Cry3Bb2 (Accession # AAA74198); Cry3Bb3 (Accession #115475); Cry3Ca1 (Accession # CAA42469); Cry4Aa1 (Accession # CAA68485); Cry4Aa2 (Accession # BAA00179); Cry4Aa3 (Accession # CAD30148); Cry4Aa4 (Accession # AFB18317); Cry4A-like (Accession # AAY96321); Cry4Ba1 (Accession # CAA30312); Cry4Ba2 (Accession # CAA30114); Cry4Ba3 (Accession # AAA22337); Cry4Ba4 (Accession # BAA00178); Cry4Ba5 (Accession # CAD30095); Cry4Ba-like (Accession # ABC47686); Cry4Ca1 (Accession # EU646202); Cry4Cb1 (Accession # FJ403208); Cry4Cb2 (Accession # FJ597622); Cry4Cc1 (Accession # FJ403207); Cry5Aa1 (Accession # AAA67694); Cry5Ab1 (Accession # AAA67693); Cry5Ac1 (Accession #134543); Cry5Ad1 (Accession # ABQ82087); Cry5Ba1 (Accession # AAA68598); Cry5Ba2 (Accession # ABW88931); Cry5Ba3 (Accession # AFJQ4417); Cry5Ca1 (Accession # HM461869); Cry5Ca2 (Accession # ZP_04123426); Cry5Da1 (Accession # HM461870); Cry5Da2 (Accession # ZP_04123980); Cry5Ea1 (Accession # HM485580); Cry5Ea2 (Accession # ZP_04124038); Cry6Aa1 (Accession # AAA22357); Cry6Aa2 (Accession # AAM46849); Cry6Aa3 (Accession # ABH03377); Cry6Ba1 (Accession # AAA22358); Cry7Aa1 (Accession # AAA22351); Cry7Ab1 (Accession # AAA21120); Cry7Ab2 (Accession # AAA21121); Cry7Ab3 (Accession # ABX24522); Cry7Ab4 (Accession # EU380678); Cry7Ab5 (Accession # ABX79555); Cry7Ab6 (Accession # AC144005); Cry7Ab7 (Accession # ADB89216); Cry7Ab8 (Accession # GU145299); Cry7Ab9 (Accession # ADD92572); Cry7Ba1 (Accession # ABB70817); Cry7Bb1 (Accession # KC156653); Cry7Ca1 (Accession # ABR67863); Cry7Cb1 (Accession # KC156698); Cry7Da1 (Accession # ACQ99547); Cry7Da2 (Accession # HM572236); Cry7Da3 (Accession # KC156679); Cry7Ea1 (Accession # HM035086); Cry7Ea2 (Accession # HM132124); Cry7Ea3

(Accession # EEM19403); Cry7Fa1 (Accession # HM035088); Cry7Fa2 (Accession # EEM19090); Cry7Fb1 (Accession # HM572235); Cry7Fb2 (Accession # KC156682); Cry7Ga1 (Accession # HM572237); Cry7Ga2 (Accession # KC156669); Cry7Gb1 (Accession # KC156650); Cry7Gc1 (Accession # KC156654); Cry7Gd1 (Accession # KC156697); Cry7Ha1 (Accession # KC156651); Cry7Ia1 (Accession # KC156665); Cry7Ja1 (Accession # KC156671); Cry7Ka1 (Accession # KC156680); Cry7Kb1 (Accession # BAM99306); Cry7La1 (Accession # BAM99307); Cry8Aa1 (Accession # AAA21117); Cry8Ab1 (Accession # EU044830); Cry8Ac1 (Accession # KC156662); Cry8Ad1 (Accession # KC156684); Cry8Ba1 (Accession # AAA21118); Cry8Bb1 (Accession # CAD57542); Cry8Bc1 (Accession # CAD57543); Cry8Ca1 (Accession # AAA21119); Cry8Ca2 (Accession # AAR98783); Cry8Ca3 (Accession # EU625349); Cry8Ca4 (Accession # ADB54826); Cry8Da1 (Accession # BAC07226); Cry8Da2 (Accession # BD133574); Cry8Da3 (Accession # BD133575); Cry8Db1 (Accession # BAF93483); Cry8Ea1 (Accession # AAQ73470); Cry8Ea2 (Accession # EU047597); Cry8Ea3 (Accession # KC855216); Cry8Fa1 (Accession # AAT48690); Cry8Fa2 (Accession # H0174208); Cry8Fa3 (Accession # AFH78109); Cry8Ga1 (Accession # AAT46073); Cry8Ga2 (Accession # ABC42043); Cry8Ga3 (Accession # FJ198072); Cry8Ha1 (Accession # AAW81032); Cry8Ia1 (Accession # EU381044); Cry8Ia2 (Accession # GU073381); Cry8Ia3 (Accession # HM044664); Cry8Ia4 (Accession # KC156674); Cry8Ib1 (Accession # GU325772); Cry8Ib2 (Accession # KC156677); Cry8Ja1 (Accession # EU625348); Cry8Ka1 (Accession # FJ422558); Cry8Ka2 (Accession # ACN87262); Cry8Kb1 (Accession # HM123758); Cry8Kb2 (Accession # KC156675); Cry8La1 (Accession # GU325771); Cry8Ma1 (Accession # HM044665); Cry8Ma2 (Accession # EEM86551); Cry8Ma3 (Accession # HM210574); Cry8Na1 (Accession # HM640939); Cry8Pa1 (Accession # H0388415); Cry8Qa1 (Accession # H0441166); Cry8Qa2 (Accession # KC152468); Cry8Ra1 (Accession # AFP87548); Cry8Sa1 (Accession # JQ740599); Cry8Ta1 (Accession # KC156673); Cry8-like (Accession # FJ770571); Cry8-like (Accession # ABS53003); Cry9Aa1 (Accession # CAA41122); Cry9Aa2 (Accession # CAA41425); Cry9Aa3 (Accession # G0249293); Cry9Aa4 (Accession # G0249294); Cry9Aa5 (Accession # JX174110); Cry9Aa like (Accession # AAQ52376); Cry9Ba1 (Accession # CAA52927); Cry9Ba2 (Accession # GU299522); Cry9Bb1 (Accession # AAV28716); Cry9Ca1 (Accession # CAA85764); Cry9Ca2 (Accession # AAQ52375); Cry9Da1 (Accession # BAA19948); Cry9Da2 (Accession # AAB97923); Cry9Da3 (Accession # G0249293); Cry9Da4 (Accession # G0249297); Cry9Db1 (Accession # AAX78439); Cry9Dc1 (Accession # KC156683); Cry9Ea1 (Accession # BAA34908); Cry9Ea2 (Accession # AA012908); Cry9Ea3 (Accession # ABM21765); Cry9Ea4 (Accession # ACE88267); Cry9Ea5 (Accession # ACF04743); Cry9Ea6 (Accession # ACG63872); Cry9Ea7 (Accession # FJ380927); Cry9Ea8 (Accession # G0249292); Cry9Ea9 (Accession # JN651495); Cry9Eb1 (Accession # CAC50780); Cry9Eb2 (Accession # G0249298); Cry9Eb3 (Accession # KC156646); Cry9Ec1 (Accession # AAC63366); Cry9Ed1 (Accession # AAX78440); Cry9Ee1 (Accession # G0249296); Cry9Ee2 (Accession # KC156664); Cry9Fa1 (Accession # KC156692); Cry9Ga1 (Accession # KC156699); Cry9-like (Accession # AAC63366); Cry10Aa1 (Accession # AAA22614); Cry10Aa2 (Accession # E00614); Cry10Aa3 (Accession # CAD30098); Cry10Aa4 (Accession # AFB18318); Cry10A-like (Accession # D0167578); Cry11Aa1 (Accession # AAA22352); Cry11Aa2 (Accession # AAA22611); Cry11Aa3 (Accession # CAD30081); Cry11Aa4 (Accession # AFB18319); Cry11Aa-like (Accession # D0166531); Cry11 Ba1 (Accession # CAA60504); Cry11Bb1 (Accession # AAC97162); Cry11Bb2 (Accession # HM068615); Cry12Aa1 (Accession # AAA22355); Cry13Aa1 (Accession # AAA22356); Cry14Aa1 (Accession # AAA21516); Cry14Ab1 (Accession # KC156652); Cry15Aa1 (Accession # AAA22333); Cry16Aa1 (Accession # CAA63860); Cry17Aa1 (Accession # CAA67841); Cry18Aa1 (Accession # CAA67506); Cry18Ba1 (Accession # AAF89667); Cry18Ca1 (Accession # AAF89668); Cry19Aa1 (Accession # CAA68875); Cry19Ba1 (Accession # BAA32397); Cry19Ca1 (Accession # AFM37572); Cry20Aa1 (Accession # AAB93476); Cry20Ba1 (Accession # ACS93601); Cry20Ba2 (Accession # KC156694); Cry20-like (Accession # GQ144333); Cry21Aa1 (Accession #132932); Cry21Aa2 (Accession #166477); Cry21 Ba1 (Accession # BAC06484); Cry21Ca1 (Accession # JF521577); Cry21Ca2 (Accession # KC156687); Cry21Da1 (Accession # JF521578); Cry22Aa1 (Accession #134547); Cry22Aa2 (Accession # CAD43579); Cry22Aa3 (Accession # ACD93211); Cry22Ab1 (Accession # AAK50456); Cry22Ab2 (Accession # CAD43577); Cry22Ba1 (Accession # CAD43578); Cry22Bb1 (Accession # KC156672); Cry23Aa1 (Accession # AAF76375); Cry24Aa1 (Accession # AAC61891); Cry24Ba1 (Accession # BAD32657); Cry24Ca1 (Accession # CAJ43600); Cry25Aa1 (Accession # AAC61892); Cry26Aa1 (Accession # AAD25075); Cry27Aa1 (Accession # BAA82796); Cry28Aa1 (Accession # AAD24189); Cry28Aa2 (Accession # AAG00235); Cry29Aa1 (Accession # CAC80985); Cry30Aa1 (Accession # CAC80986); Cry30Ba1 (Accession # BAD00052); Cry30Ca1 (Accession # BAD67157); Cry30Ca2 (Accession # ACU24781); Cry30Da1 (Accession # EF095955); Cry30Db1 (Accession # BAE80088); Cry30Ea1 (Accession # ACC95445); Cry30Ea2 (Accession # FJ499389); Cry30Fa1 (Accession # ACI22625); Cry30Ga1 (Accession # ACG60020); Cry30Ga2 (Accession # HQ638217); Cry31Aa1 (Accession # BAB11757); Cry31Aa2 (Accession # AAL87458); Cry31Aa3 (Accession # BAE79808); Cry31Aa4 (Accession # BAF32571); Cry31Aa5 (Accession # BAF32572); Cry31Aa6 (Accession # BA144026); Cry31Ab1 (Accession # BAE79809); Cry31Ab2 (Accession # BAF32570); Cry31Ac1 (Accession # BAF34368); Cry31Ac2 (Accession # AB731600); Cry31Ad1 (Accession # BA144022); Cry32Aa1 (Accession # AAG36711); Cry32Aa2 (Accession # GU063849); Cry32Ab1 (Accession # GU063850); Cry32Ba1 (Accession # BAB78601); Cry32Ca1 (Accession # BAB78602); Cry32Cb1 (Accession # KC156708); Cry32Da1 (Accession # BAB78603); Cry32Ea1 (Accession # GU324274); Cry32Ea2 (Accession # KC156686); Cry32Eb1 (Accession # KC156663); Cry32Fa1 (Accession # KC156656); Cry32Ga1 (Accession # KC156657); Cry32Ha1 (Accession # KC156661); Cry32Hb1 (Accession # KC156666); Cry32Ia1 (Accession # KC156667); Cry32Ja1 (Accession # KC156685); Cry32Ka1 (Accession # KC156688); Cry32La1 (Accession # KC156689); Cry32Ma1 (Accession # KC156690); Cry32Mb1 (Accession # KC156704); Cry32Na1 (Accession # KC156691); Cry32Oa1 (Accession # KC156703); Cry32Pa1 (Accession # KC156705); Cry32Qa1 (Accession # KC156706); Cry32Ra1 (Accession # KC156707); Cry32Sa1 (Accession # KC156709);

Cry32Ta1 (Accession # KC156710); Cry32Ua1 (Accession # KC156655); Cry33Aa1 (Accession # AAL26871); Cry34Aa1 (Accession # AAG50341); Cry34Aa2 (Accession # AAK64560); Cry34Aa3 (Accession # AAT29032); Cry34Aa4 (Accession # AAT29030); Cry34Ab1 (Accession # AAG41671); Cry34Ac1 (Accession # AAG50118); Cry34Ac2 (Accession # AAK64562); Cry34Ac3 (Accession # AAT29029); Cry34Ba1 (Accession # AAK64565); Cry34Ba2 (Accession # AAT29033); Cry34Ba3 (Accession # AAT29031); Cry35Aa1 (Accession # AAG50342); Cry35Aa2 (Accession # AAK64561); Cry35Aa3 (Accession # AAT29028); Cry35Aa4 (Accession # AAT29025); Cry35Ab1 (Accession # AAG41672); Cry35Ab2 (Accession # AAK64563); Cry35Ab3 (Accession # AY536891); Cry35Ac1 (Accession # AAG50117); Cry35Ba1 (Accession # AAK64566); Cry35Ba2 (Accession # AAT29027); Cry35Ba3 (Accession # AAT29026); Cry36Aa1 (Accession # AAK64558); Cry37Aa1 (Accession # AAF76376); Cry38Aa1 (Accession # AAK64559); Cry39Aa1 (Accession # BAB72016); Cry40Aa1 (Accession # BAB72018); Cry40Ba1 (Accession # BAC77648); Cry40Ca1 (Accession # EU381045); Cry40Da1 (Accession # ACF15199); Cry41Aa1 (Accession # BAD35157); Cry41Ab1 (Accession # BAD35163); Cry41Ba1 (Accession # HM461871); Cry41Ba2 (Accession # ZP_04099652); Cry42Aa1 (Accession # BAD35166); Cry43Aa1 (Accession # BAD15301); Cry43Aa2 (Accession # BAD95474); Cry43Ba1 (Accession # BAD15303); Cry43Ca1 (Accession # KC156676); Cry43Cb1 (Accession # KC156695); Cry43Cc1 (Accession # KC156696); Cry43-like (Accession # BAD15305); Cry44Aa (Accession # BAD08532); Cry45Aa (Accession # BAD22577); Cry46Aa (Accession # BAC79010); Cry46Aa2 (Accession # BAG68906); Cry46Ab (Accession # BAD35170); Cry47Aa (Accession # AAY24695); Cry48Aa (Accession # CAJ18351); Cry48Aa2 (Accession # CAJ86545); Cry48Aa3 (Accession # CAJ86546); Cry48Ab (Accession # CAJ86548); Cry48Ab2 (Accession # CAJ86549); Cry49Aa (Accession # CAH56541); Cry49Aa2 (Accession # CAJ86541); Cry49Aa3 (Accession # CAJ86543); Cry49Aa4 (Accession # CAJ86544); Cry49Ab1 (Accession # CAJ86542); Cry50Aa1 (Accession # BAE86999); Cry50Ba1 (Accession # GU446675); Cry50Ba2 (Accession # GU446676); Cry51Aa1 (Accession # AB114444); Cry51Aa2 (Accession # GU570697); Cry52Aa1 (Accession # EF613489); Cry52Ba1 (Accession # FJ361760); Cry53Aa1 (Accession # EF633476); Cry53Ab1 (Accession # FJ361759); Cry54Aa1 (Accession # ACA52194); Cry54Aa2 (Accession # GQ140349); Cry54Ba1 (Accession # GU446677); Cry55Aa1 (Accession # ABW88932); Cry54Ab1 (Accession # JQ916908); Cry55Aa2 (Accession # AAE33526); Cry56Aa1 (Accession # ACU57499); Cry56Aa2 (Accession # G0483512); Cry56Aa3 (Accession # JX025567); Cry57Aa1 (Accession # ANC87261); Cry58Aa1 (Accession # ANC87260); Cry59Ba1 (Accession # JN790647); Cry59Aa1 (Accession # ACR43758); Cry60Aa1 (Accession # ACU24782); Cry60Aa2 (Accession # EA057254); Cry60Aa3 (Accession # EEM99278); Cry60Ba1 (Accession # GU810818); Cry60Ba2 (Accession # EA057253); Cry60Ba3 (Accession # EEM99279); Cry61Aa1 (Accession # HM035087); Cry61Aa2 (Accession # HM132125); Cry61Aa3 (Accession # EEM19308); Cry62Aa1 (Accession # HM054509); Cry63Aa1 (Accession # BA144028); Cry64Aa1 (Accession # BAJQ5397); Cry65Aa1 (Accession # HM461868); Cry65Aa2 (Accession # ZP_04123838); Cry66Aa1 (Accession # HM485581); Cry66Aa2 (Accession # ZP_04099945); Cry67Aa1 (Accession # HM485582); Cry67Aa2 (Accession # ZP_04148882); Cry68Aa1 (Accession # H0113114); Cry69Aa1 (Accession # H0401006); Cry69Aa2 (Accession # JQ821388); Cry69Ab1 (Accession # JN209957); Cry70Aa1 (Accession # JN646781); Cry70Ba1 (Accession # AD051070); Cry70Bb1 (Accession # EEL67276); Cry71Aa1 (Accession # JX025568); Cry72Aa1 (Accession # JX025569); Cry73A1 (Accession # AEH76822), Cry74Aa (NCBI Protein 657629748), Cyt1Aa (GenBank Accession Number X03182); Cyt1Ab (GenBank Accession Number X98793); Cyt1B (GenBank Accession Number U37196); Cyt2A (GenBank Accession Number Z14147); and Cyt2B (GenBank Accession Number U52043).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) Applied and Environmental Microbiology 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) J. Invert. Path. 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) Plant Biotech Journal 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) Biochem Biophys Res Commun 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as Xenorhabdus, *Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

In some embodiments the polynucleotides encoding the insecticidal polypeptide disclosed herein may be stacked with genes encoding a Cry1B, Cry9 and/or Cry1Ia14.

In some embodiments the polynucleotides encoding the insecticidal polypeptide disclosed herein may be stacked with genes encoding a Cry1B of U.S. Pat. Nos. 8,129,594, 8,772,577, WO2015/021139, and/or Serial No. PCT/US2015/55491.

In some embodiments the polynucleotides encoding the insecticidal polypeptide disclosed herein may be stacked with genes encoding a Cry1B polypeptide having at least 95% sequence identity to the amino acid sequence of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53 or SEQ ID NO: 55.

In some embodiments the polynucleotides encoding the insecticidal polypeptide disclosed herein may be stacked with genes encoding a Cry9 of U.S. Pat. Nos. 8,802,933, 8,802,934, 8,319,019, 8,445,749, and/or 9,000,261.

In some embodiments the polynucleotides encoding the insecticidal polypeptide disclosed herein may be stacked with genes encoding a Cry1Ia14 polypeptide having at least 95% sequence identity to the amino acid sequence of SEQ ID NO: 57 or SEQ ID NO: 59.

These stacked combinations can be created by any method including but not limited to cross breeding plants by any conventional or TOPCROSS® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Compositions of the embodiments find use in protecting plants, seeds, and plant products in a variety of ways. For example, the compositions can be used in a method that involves placing an effective amount of the pesticidal composition in the environment of the pest by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the embodiments comprising a nucleotide sequence encoding a pesticidal protein of the embodiments may be treated with a seed protectant coating comprising a seed treatment compound, such as, for example, captan, carboxin, thiram, methalaxyl, pirimiphos-methyl, and others that are commonly used in seed treatment. In one embodiment, a seed protectant coating comprising a pesticidal composition of the embodiments is used alone or in combination with one of the seed protectant coatings customarily used in seed treatment.

It is recognized that the genes encoding the pesticidal proteins can be used to transform insect pathogenic organisms. Such organisms include baculoviruses, fungi, protozoa, bacteria, and nematodes.

A gene encoding a pesticidal protein of the embodiments may be introduced via a suitable vector into a microbial host, and said host applied to the environment, or to plants or animals. The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid, or mitochondrial DNA), converted into an autonomous replicon, or transiently expressed (e.g., transfected mRNA).

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, Rhodotorula glutinis, Rhodotorula marina, Rhodotorula aurantiaca, Cryptococcus albidus, Cryptococcus diffluens, Cryptococcus laurentii, Saccharomyces rosei, Saccharomyces pretoriensis, Saccharomyces cerevisiae, Sporobolomyces roseus, Saccharomyces odorus, Kluyveromyces veronae*, and *Aureobasidium* pollulans. Of particular interest are the pigmented microorganisms.

A number of ways are available for introducing a gene expressing the pesticidal protein into the microorganism host under conditions that allow for stable maintenance and expression of the gene. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook; Maniatis et al. (Cold Spring Harbor Laboratory Press, Cold Spring Harbor, N.Y.); Davis et al., eds. (1980) *Advanced Bacterial Genetics* (Cold Spring Harbor Laboratory Press, Cold Spring Harbor, N.Y.) and the references cited therein.

Suitable host cells, where the pesticidal protein-containing cells will be treated to prolong the activity of the pesticidal proteins in the cell when the treated cell is applied to the environment of the target pest(s), may include either prokaryotes or eukaryotes, normally being limited to those cells that do not produce substances toxic to higher organisms, such as mammals. However, organisms that produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and gram-positive, include Enterobacteriaceae, such as *Escherichia, Erwinia, Shigella, Salmonella*, and *Proteus*; Bacillaceae; Rhizobiaceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Characteristics of particular interest in selecting a host cell for purposes of pesticidal protein production include ease of introducing the pesticidal protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* spp., *Aureobasidium* spp., *Saccharomyces* spp. (such as *Saccharomyces cerevisiae*), *Sporobolomyces* spp., phylloplane organisms such as *Pseudomonas* spp. (such as *Pseudomonas aeruginosa, Pseudomonas fluorescens*), *Erwinia* spp., and *Flavobacterium* spp., and other such organisms, including Bt, *E. coli, Bacillus subtilis*, and the like.

Genes encoding the pesticidal proteins of the embodiments can be introduced into microorganisms that multiply on plants (epiphytes) to deliver pesticidal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the pesticidal proteins of the embodiments can be introduced into a root-colonizing *Bacillus cereus* by standard methods known in the art.

Genes encoding pesticidal proteins can be introduced, for example, into the root-colonizing *Bacillus* by means of electrotransformation. Specifically, genes encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60: 211-218).

Expression systems can be designed so that pesticidal proteins are secreted outside the cytoplasm of gram-negative bacteria, such as *E. coli*, for example. Advantages of having pesticidal proteins secreted are: (1) avoidance of potential cytotoxic effects of the pesticidal protein expressed; and (2) improvement in the efficiency of purification of the pesticidal protein, including, but not limited to, increased efficiency in the recovery and purification of the protein per volume cell broth and decreased time and/or costs of recovery and purification per unit protein.

Pesticidal proteins can be made to be secreted in *E. coli*, for example, by fusing an appropriate *E. coli* signal peptide to the amino-terminal end of the pesticidal protein. Signal peptides recognized by *E. coli* can be found in proteins already known to be secreted in *E. coli*, for example the OmpA protein (Ghrayeb et al. (1984) *EMBO J,* 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153: 492).

In another embodiment polynucleotides encoding a MP448 (SEQ ID NO: 2) or MP627 (SEQ ID NO: 4) polypeptide may be fused to signal sequences which will direct the localization of the MP448 (SEQ ID NO: 2) or MP627 (SEQ ID NO: 4) polypeptide to particular compartments of a prokaryotic or eukaryotic cell and/or direct the secretion of the MP448 (SEQ ID NO: 2) or MP627 (SEQ ID NO: 4) polypeptide of the embodiments from a prokaryotic or eukaryotic cell. For example, in *E. coli*, one may wish to direct the expression of the protein to the periplasmic space. Examples of signal sequences or proteins (or fragments thereof) to which the MP448 (SEQ ID NO: 2) or MP627 (SEQ ID NO: 4) polypeptide may be fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit and the signal sequence of alkaline phosphatase. Several vectors are commercially available for the construction of fusion proteins which will direct the localization of a protein, such as the pMAL series of vectors (particularly the pMAL-p series) available from New England Biolabs. In a specific embodiment, the MP448 (SEQ ID NO: 2) or MP627 (SEQ ID NO: 4) polypeptide may be fused to the pelB pectate lyase signal sequence to increase the efficiency of expression and purification of such polypeptides in Gram-negative bacteria (see, U.S. Pat. Nos. 5,576,195 and 5,846,818). Plant plastid transit peptide/polypeptide fusions are well known in the art (see, U.S. Pat. No. 7,193,133). Apoplast transit peptides such as rice or barley alpha-amylase secretion signal are also well known in the art. The plastid transit peptide is generally fused N-terminal to the polypeptide to be targeted (e.g., the fusion partner). In one embodiment, the fusion protein consists essentially of the plastid transit peptide and the MP448 (SEQ ID NO: 2) or MP627 (SEQ ID NO: 4) polypeptide to be targeted. In another embodiment, the fusion protein comprises the plastid transit peptide and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third or N-terminal quarter of the fusion protein. Most or all of the plastid transit peptide is generally cleaved from the fusion protein upon insertion into the plastid. The position of cleavage may vary slightly between plant species, at different plant developmental stages, as a result of specific intercellular conditions or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins. The plastid transit peptide can be recombinantly fused to a second protein in one of several ways. For example, a restriction endonuclease recognition site can be introduced into the nucleotide sequence of the transit peptide at a position corresponding to its C-terminal end and the same or a compatible site can be engineered into the nucleotide sequence of the protein to be targeted at its N-terminal end. Care must be taken in designing these sites to ensure that the coding sequences of the transit peptide and the second protein are kept “in frame” to allow the synthesis of the desired fusion protein. In some cases, it may be preferable to remove the initiator methionine of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise cleavage site between the transit peptide and the second protein (with or without its initiator methionine) using gene synthesis (Stemmer, et al., (1995) Gene 164:49-53) or similar methods. In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai, et al., (1988) J. Biol. Chem. 263(29):15104-9.

Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) Methods Enzymol. 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. FEBS LETT 480:271-276, 2000; Peltier et al. Plant Cell 12:319-341, 2000; Bricker et al. Biochim. Biophys Acta 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., Photosynthesis Research, 78:249-264, 2003. In particular, Table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present disclosure.

Suitable chloroplast transit peptides (CTP) are well known to one skilled in the art also include chimeric CT's comprising but not limited to, an N-terminal domain, a central domain or a C-terminal domain from a CTP from *Oryza sativa* 1-decoy-D xylose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type US Patent Application Publication 2012/0304336).

The MP448 (SEQ ID NO: 2) or MP627 (SEQ ID NO: 4) polypeptide gene to be targeted to the chloroplast may be optimized for expression in the chloroplast to account for differences in usage between the plant nucleus and this organelle. In this manner, the nucleic acids of interest may be synthesized using chloroplast-preferred s. See, for example, U.S. Pat. No. 5,380,831, herein incorporated by reference.

Pesticidal proteins of the embodiments can be fermented in a bacterial host and the resulting bacteria processed and used as a microbial spray in the same manner that Bt strains have been used as insecticidal sprays. In the case of a pesticidal protein(s) that is secreted from *Bacillus*, the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins. Any suitable microorganism can be used for this purpose. *Pseudomonas* has been used to express Bt toxins as encapsulated proteins and the resulting cells processed and sprayed as an insecticide (Gaertner et al. (1993), in: *Advanced Engineered Pesticides*, ed. Kim).

Alternatively, the pesticidal proteins are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticidal proteins may then be formulated in accordance with conventional techniques for application to the environment hosting a target pest, e.g., soil, water, and foliage of plants. See, for example EP0192319, and the references cited therein.

In the embodiments, a transformed microorganism (which includes whole organisms, cells, spore(s), pesticidal protein (s), pesticidal component(s), pest-impacting component(s), mutant(s), living or dead cells and cell components, including mixtures of living and dead cells and cell components, and including broken cells and cell components) or an isolated pesticidal protein can be formulated with an acceptable carrier into a pesticidal composition(s) that is, for example, a suspension, a solution, an emulsion, a dusting powder, a dispersible granule or pellet, a wettable powder, and an emulsifiable concentrate, an aerosol or spray, an impregnated granule, an adjuvant, a coatable paste, a colloid, and also encapsulations in, for example, polymer substances. Such formulated compositions may be prepared by such conventional means as desiccation, lyophilization, homogenization, extraction, filtration, centrifugation, sedimentation, or concentration of a culture of cells comprising the polypeptide.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the embodiments are normally applied in the form of compositions and can be applied to the crop area, plant, or seed to be treated. For example, the compositions of the embodiments may be applied to grain in preparation for or during storage in a grain bin or silo, etc. The compositions of the embodiments may be applied simultaneously or in succession with other compounds. Methods of applying an active ingredient of the embodiments or an agrochemical composition of the embodiments that contains at least one of the pesticidal proteins produced by the bacterial strains of the embodiments include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the embodiments can be in a suitable form for direct application or as a concentrate of primary composition that requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and pesticidal proteins of the embodiments, can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

In other embodiments, it may be advantageous to treat the Cry toxin polypeptides with a protease, for example trypsin, to activate the protein prior to application of a pesticidal protein composition of the embodiments to the environment of the target pest. Methods for the activation of protoxin by a serine protease are well known in the art. See, for example, Cooksey (1968) *Biochem. J.* 6:445-454 and Carroll and Ellar (1989) *Biochem. J.* 261:99-105, the teachings of which are herein incorporated by reference. For example, a suitable activation protocol includes, but is not limited to, combining a polypeptide to be activated, for example a purified novel Cry polypeptide (e.g., having the amino acid sequence set forth in SEQ ID NO: 2 or SEQ ID NO: 4), and trypsin at a 1/100 weight ratio of protein/trypsin in 20 nM NaHCO$_3$, pH 8 and digesting the sample at 36 C for 3 hours.

The compositions (including the transformed microorganisms and pesticidal proteins of the embodiments) can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the pesticidal protein and/or transformed microorganisms of the embodiments may be mixed with grain to protect the grain during storage. It is generally important to obtain good control of pests in the early stages of plant growth, as this is the time when the plant can be most severely damaged. The compositions of the embodiments can conveniently contain another insecticide if this is thought necessary. In one embodiment, the composition is applied directly to the soil, at a time of planting, in granular form of a composition of a carrier and dead cells of a *Bacillus* strain or transformed microorganism of the embodiments. Another embodiment is a granular form of a composition comprising an agrochemical such as, for example, an herbicide, an insecticide, a fertilizer, an inert carrier, and dead cells of a *Bacillus* strain or transformed microorganism of the embodiments.

Those skilled in the art will recognize that not all compounds are equally effective against all pests. Compounds of the embodiments display activity against insect pests, which may include economically important agronomic, forest, greenhouse, nursery, ornamentals, food and fiber, public and animal health, domestic and commercial structure, household, and stored product pests. Insect pests include insects selected from the orders Coleoptera, Diptera, Hymenoptera, *Lepidoptera*, Mallophaga, Homoptera, Hemiptera, Orthoptera, Thysanoptera, Dermaptera, Isoptera, Anoplura, Siphonaptera, Trichoptera, etc., particularly Coleoptera and *Lepidoptera*.

Insects of the order *Lepidoptera* include, but are not limited to, armyworms, cutworms, loopers, and heliothines in the family Noctuidae *Agrotis ipsilon* Hufnagel (black cutworm); *Agrotis orthogonia* Morrison (western cutworm); *Agrotis segetum* Denis & Schiffermüller (turnip moth); *Agrotis subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *Earias vittella* Fabricius (spotted bollworm); *Egira* (*Xylomyges*) *curialis* Grote (citrus cutworm); *Euxoa messoria* Harris (darksided cutworm); *Helicoverpa armigera* Hübner (American bollworm); *Helicoverpa zea* Boddie (corn earworm or cotton bollworm); *Heliothis virescens* Fabricius (tobacco budworm); *Hypena scabra* Fabricius (green cloverworm); *Mamestra configurata* Walker (bertha armyworm); *Mamestra brassicae* Linnaeus (cabbage moth); *Melanchra picta* Harris (zebra caterpillar); *Pseudaletia unipuncta* Haworth (armyworm); *Pseudoplusia includens* Walker (soybean looper); *Richia albicosta* Smith (Western bean cutworm); *Spodoptera frugiperda* JE Smith (fall armyworm); *Spodoptera exigua* Hübner (beet armyworm); *Spodoptera litura* Fabricius (tobacco cutworm, cluster caterpillar); *Trichoplusia ni* Hübner (cabbage looper); borers, casebearers, webworms, coneworms, and skeletonizers from the families Pyralidae, Castniidae, and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo auricilius* (Stalk Borer); *Chilo infuscatellus* (Early shoot Borer); *Chilo partellus* Swinhoe (spotted stalk borer); *Chilo sacchariphagus indicus* (Internode Borer); *Chilo suppressalis* Walker (striped stem/rice borer); *Chilo terrenellus* Pagenstecher (sugarcane stemp borer); *Corcyra cephalonica* Stainton (rice moth); *Crambus caliginosellus* Clemens (corn root webworm); *Crambus teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *Diaphania nitidalis* Stoll (pickleworm); *Diatraea grandiosella* Dyar (southwestern corn borer), *Diatraea saccharalis* Fabricius (surgarcane borer); *Elasmopalpus lignosellus* Zeller (lesser cornstalk borer); *Emmalocera Depressella* (Root Borer); *Eoreuma loftini* Dyar (Mexican rice borer); *Ephestia elutella* Hübner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower head moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hübner (European corn borer); *Plodia interpunctella* Hübner (Indian meal moth); *Scirpophaga incertulas* Walker (yellow stem borer); *Scirpophaga nivella* (Sugarcane Top Borer); *Udea rubigalis* Guenée (celery leaftier); *Telchin licus* (banana stem borer); and leafrollers, budworms, seed worms, and fruit worms in the family Tortricidae *Acleris gloverana* Walsingham (Western blackheaded budworm); *Acleris variana* Fernald (Eastern blackheaded budworm); *Adoxophyes orana* Fischer von Rösslerstamm (summer fruit tortrix moth); *Archips* spp. including *Archips argyrospila* Walker (fruit tree leaf roller) and *Archips rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *Cydia pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermüller (European grape vine moth); *Platynota flavedana* Clemens (variegated leafroller); *Platynota stultana* Walsingham (omnivorous leafroller); *Spilonota ocellana* Denis & Schiffermüller (eyespotted bud moth); and *Suleima helianthana* Riley (sunflower bud moth).

Selected other agronomic pests in the order *Lepidoptera* include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Collas eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *Lambdina fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *Manduca sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leaf miner); *Phyllonorycter blancardella* Fabricius (spotted tentiform leafminer); *Pieris brassicae* Linnaeus (large white butterfly); *Pieris rapae* Linnaeus (small white butterfly); *Pieris napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (Diaprepes root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *Sitophilus oryzae* Linnaeus (rice weevil); *Smicronyx fulvus* LeConte (red sunflower seed weevil); *Smicronyx sordidus* LeConte (gray sunflower seed weevil); *Sphenophorus levis* (sugarcane weevil); *Sphenophorus maidis* Chittenden (maize billbug); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *Chaetocnema pulicaria* Melsheimer (corn flea beetle); *Colaspis brunnea* Fabricius (grape colaspis); *Diabrotica barberi* Smith & Lawrence (northern corn rootworm); *Diabrotica undecimpunctata howardi* Barber (southern corn rootworm); *Diabrotica virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *Cyclocephala immaculata* Olivier (southern masked chafer, white grub); *Dermolepida albohirtum* Waterhouse (Greyback cane beetle); *Euetheola humilis* rugiceps LeConte (sugarcane beetle); *Lepidiota frenchi* Blackburn (French's cane grub); *Tomarus gibbosus* De Geer (carrot beetle); *Tomarus subtropicus* Blatchley (sugarcane grub); *Phyllophaga crinita* Burmeister (white grub); *Phyllophaga latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *Melanotus communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

Adults and immatures of the order Diptera are of interest, including leafminers *Agromyza parvicornis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *Delia coarctata* Fallen (wheat bulb fly); *Fannia canicularis* Linnaeus, *Fannia femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are those of the order Hemiptera such as, but not limited to, the following families: Adelgidae, Aleyrodidae, Aphididae, Asterolecaniidae, Cercopidae, Cicadellidae, Cicadidae, Cixiidae, Coccidae, Coreidae, Dactylopiidae, Delphacidae, Diaspididae, Eriococcidae, Flatidae, Fulgoridae, lssidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *Aphis fabae* Scopoli (black bean aphid); *Aphis gossypii* Glover (cotton aphid, melon aphid); *Aphis maidiradicis* Forbes (corn root aphid); *Aphis pomi* De Geer (apple aphid); *Aphis spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *Bemisia argentifolii* Bellows & Perring (silverleaf whitefly); *Blissus leucopterus leucopterus* Say (chinch bug); *Blostomatidae* spp.; *Brevicoryne brassicae* Linnaeus (cabbage aphid); *Cacopsylla pyricola* Foerster (pear *psylla*); *Calocoris norvegicus* Gmelin (potato capsid bug); *Chaetosiphon fragaefolii* Cockerell (strawberry aphid); *Cimicidae* spp.; *Coreidae* spp.; *Corythuca gossypii* Fabricius (cotton lace bug); *Cyrtopeltis modesta* Distant (tomato bug); *Cyrtopeltis notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schaffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *Euschistus variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *Lygus Hesperus* Knight (Western tarnished plant bug); *Lygus pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *Melanaphis sacchari* Zehntner (sugarcane aphid); *Melanaspis*

*glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); Pyrrhocoridae spp.; *Quadraspidiotus perniciosus* Comstock (San Jose scale); *Reduviidae* spp.; *Rhopalosiphum maidis* Fitch (corn leaf aphid); *Rhopalosiphum padi* Linnaeus (bird cherry-oat aphid); *Saccharicoccus sacchari* Cockerell (pink sugarcane mealybug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); *Tinidae* spp.; *Toxoptera aurantii* Boyer de Fonscolombe (black citrus aphid); and *Toxoptera citricida* Kirkaldy (brown citrus aphid); *Trialeurodes abutiloneus* (bandedwinged whitefly) and *Trialeurodes vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as *Aceria tosichella* Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus grypus* Baker & Pritchard, *Oligonychus indicus* Hirst (sugarcane leaf mite), *Oligonychus pratensis* Banks (Banks grass mite), *Oligonychus stickneyi* McGregor (sugarcane spider mite); *Tetranychus urticae* Koch (two spotted spider mite); *Tetranychus mcdanieli* McGregor (McDaniel mite); *Tetranychus cinnabarinus* Boisduval (carmine spider mite); Tetranychus turkestani Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae: *Ixodes scapularis* Say (deer tick); *Ixodes holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cylindrotermes nordenskioeldi* Holmgren and *Pseudacanthotermes militaris* Hagen (sugarcane termite). Insects of the order Thysanoptera are also of interest, including but not limited to *thrips*, such as *Stenchaetothrips minutus* van Deventer (sugarcane thrips).

Insect pests may be tested for pesticidal activity of compositions of the embodiments in early developmental stages, e.g., as larvae or other immature forms. The insects may be reared in total darkness at from about 20° C. to about 30° C. and from about 30% to about 70% relative humidity. Bioassays may be performed as described in Czapla and Lang (1990) *J. Econ. Entomol.* 83(6): 2480-2485. Methods of rearing insect larvae and performing bioassays are well known to one of ordinary skill in the art.

A wide variety of bioassay techniques are known to one skilled in the art. General procedures include addition of the experimental compound or organism to the diet source in an enclosed container. Pesticidal activity can be measured by, but is not limited to, changes in mortality, weight loss, attraction, repellency and other behavioral and physical changes after feeding and exposure for an appropriate length of time. Bioassays described herein can be used with any feeding insect pest in the larval or adult stage.

The following examples are presented by way of illustration, not by way of limitation.

EXPERIMENTALS

Example 1: Gene Identification and *E. coli* Expression

A synthetic gene (SEQ ID NO: 1) was synthesized encoding the MP448 insecticidal protein of SEQ ID NO: 2 which was identified from a screen of *Bacillus thuringiensis* isolates from an internal DuPont proprietary collection from a strain designated as AM1014.

A synthetic gene (SEQ ID NO: 3) was synthesized encoding the MP627 insecticidal protein of SEQ ID NO: 4 which was identified from a screen of *Bacillus thuringiensis* isolates from an internal DuPont proprietary collection from a strain designated as DP1246.

Polynucleotides encoding the MP448 and MP627 polypeptides were cloned into a pET28a vector (Novagen®) and transformed into *E. coli* BL21 cells (Invitrogen). Large scale 1.0 L cultures were grown until O.D. 600 nm~0.8 and then the cultures were induced with isopropyl β-D-1-thiogalactopyranoside (IPTG) 1 mM and allowed to grow for 16 hours at 16° C. The cell pellets were lysed with 50 mL of 500 mM NaCl/20 mM Tris/5 mM Imidazole/pH 7.9 with 0.02% lysozyme (w/v) and 0.1% Tween-20 and 1 tablet of Complete Protease Inhibitor (Roche) added. After lysis, the solutions were sonicated and the lysate centrifuged at 25,000 rpm for 30 minutes. The supernatant containing the soluble protein fraction were filtered through a 0.45u vacuum filter and then 1 ml of Talon (Clontech) slurry is added and then incubated for binding on rotator at 100 rpm for 1 hour. The lysate was then added to a column and the bound protein was isolated and washed with 20 ml of 50 mM NaCl/20 mM Tris/5 mM Imidazole/pH 7.9 and then eluted with 1.5 ml of 50mmM NaCl/20 mM Tris/500 mM Imidazole/pH 7.9. The purified protein was then dialyzed into 50 mM sodium carbonate buffer pH10. The purified protein was submitted for insecticidal activity in panel of Lepidoptera in vitro feeding assays.

Example 2: Lepidoptera Assays with Partially Purified Proteins

Insecticidal activity bioassay screens were conducted to evaluate the effects of the insecticidal proteins on a variety of Lepidoptera species: European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*).

Lepidoptera feeding assays were conducted on an artificial diet containing the purified protein in a 96 well plate set up. The purified protein (25 ul) is then added to the artificial diet. Two to five neonate larvae were placed in each well to feed ad libitum for 5 days. Results were expressed as positive for larvae reactions such as stunting and or mortality. Results were expressed as negative if the larvae were similar to the negative control that is feeding diet to which the above buffer only has been applied. A primary bioassay screen was performed for each purified protein at a single concentration on European corn borer (*Ostrinia nubilalis*), corn earworm (*Helicoverpa zea*), black cutworm (*Agrotis ipsilon*), fall armyworm (*Spodoptera frugiperda*), Soybean looper (*Pseudoplusia includens*) and Velvet bean caterpillar (*Anticarsia gemmatalis*). The insect assays were scored as follows: 3=100% mortality; 2=severe stunting; 1=stunting; and 0=no activity.

The primary and secondary insecticidal assay screening results for the MP448 (SEQ ID NO: 2) insecticidal polypeptide are shown in Table 1.

The primary insecticidal assay screening results for the MP627 (SEQ ID NO: 4) insecticidal polypeptide is shown in Table 2.

*Diatraea saccharalis* (Sugarcane borer) neonates obtained from Benzon Research, PA. The plates were sealed with a Mylar sheet and holes punched in the Mylar to allow oxygen and moisture exchange. The plates were incubated in the dark for four days at 28° C. and then scored. LC50 values were determined based on mortality and Inhibition Concentrations (IC50) values were determined using a weighted scoring system based on development. The results are shown in Table 3.

TABLE 3

|  | LC50 | ILC50 |
|---|---|---|
| MP448 (SEQ ID NO: 2) | 9.7 ppm | 4.2 ppm |
| MP627 (SEQ ID NO: 4) | 3.9 ppm | 1.2 ppm |

Example 4: Cross Resistance of Insecticidal Polypeptides in Cry1Ab or Cry1F Resistant Strain of European Corn Borer (ECB)

To determine if Cry1Ab and Cry1F resistant insects were cross resistant to MP448 (SEQ ID NO: 2) and MP627 (SEQ ID NO: 4), European corn borer (*Ostrinia nubilalis*) larvae susceptible or resistant to Cry1Ab (Crespo A. et al., *Pest Manag Sci* 65: 1071-1081, 2009) or Cry1F (Siegfried B. et al., *Pest Manag Sci* 70: 725-733, 2014), were treated with MP448 (SEQ ID NO: 2) or MP627 (SEQ ID NO: 4).

The laboratory Cry1F-selected strain (Cry1F-R) was originated from a combination of five field populations collected in 2007 and was selected for resistance using increasing amounts of lyophilized leaf tissue of Cry1F expressing maize.

Larval susceptibility of the Bt susceptible (SS) and resistant strains (Cry1Ab-R and Cry1F-R) of *Ostrinia nubilalis*

TABLE 1

| | | 4 reps for all bugs | | | | | | | |
|---|---|---|---|---|---|---|---|---|---|
| Topical/Drop | Concentration | | | | | | | WCRW | |
| Plate | (ug/cm2) | ECB | FAW | BCW | CEW | SBL | VBC | −Trypsin | +Trypsin |
| Primary Screen | >200 | 3 | 0 | 2.5 | 2 | 3 | 2.25 | NA | 0 |
| Secondary Screen | 100 | 2.75 | | 0.75 | 1.5 | 3 | 2.25 | | |
| Repeat | 20 | 2.5 | 0 | 0 | 0 | 2 | 2 | | |

TABLE 2

| | | 4 observations per bug | | | | | | | |
|---|---|---|---|---|---|---|---|---|---|
| Topical/Drop | Concentration | | | | | | | WCRW | |
| Plate | (ug/cm2) | ECB | FAW | BCW | CEW | SBL | VBC | −Trypsin | +Trypsin |
| Primary Screen | 100 | 3 | 0 | 0 | 0 | 1 | 3 | 0 | NA |

Example 3: Sugar Cane Borer Insecticidal Activity 10 ul of sample were incorporated into 50 ul of solidified MultiSpecies Lepidopteran Diet (Southland Products, AR) in each well of a polystyrene 96 well bioassay plate (Falcon 353910). Each well was infested with between 2 to 4 to the insecticidal proteins were determined using a diet incorporated bioassay method. Briefly, 25 ul of a sample concentration is mixed with 75 ul of artificial diet per well in a 96 well plate format. Each bioassay included six to ten concentrations of a sample apart from the negative control, three to four replications for each concentration, and eight individuals for each replication. The protein solutions were prepared by mixing proteins with appropriate amount of buffer solutions. One neonate larva (<24 h after hatch) will be placed in each assay well. Mortality and larval growth inhibition (defined as inhibition if larva did not enter second instar within 6 days) by each sample were scored after 6 days of feeding on the treated diet at 27° C., 50% RH, and a photoperiod of 16:8 hours (L:D). Concentrations for 50% mortality (LC50) or inhibition of 50% of the individuals (1050) were calculated based on probit analysis, and statistical analyses performed by using statistical software.

The resistance ratio for MP448 (SEQ ID NO: 2) and MP627 (SEQ ID NO: 4) was determined to be ~1 indicating the lack of cross-resistance of MP448 (SEQ ID NO: 42 and MP627 (SEQ ID NO: 4) with Cry1Ab and Cry1F insecticidal polypeptides against European corn borer (*Ostrinia nubilalis*) larvae (Table 4 and Table 5).

TABLE 4

| Protein | ECB colony | LC/IC | ppm, 6 d | Lower 95% CL | Upper 95% CL | Res Ratio |
|---|---|---|---|---|---|---|
| MP448 | SS | LC50 | 25.78 | 15.69 | 39.66 | 1.0 |
| SEQ ID | | IC50 | 7.606 | 4.790 | 10.41 | 1.0 |
| NO: 2 | Cry1A-R | LC50 | 43.32 | 25.17 | 78.88 | 1.7 |
| | | IC50 | 7.171 | 3.723 | 11.77 | 0.9 |
| | Cry1F-R | LC50 | <100 | | | <4 |
| | | IC50 | <10 | | | <1.3 |

TABLE 5

| Protein | ECB colony | LC50, ppm, 6 d | Res Ratio |
|---|---|---|---|
| MP627 | SS | ~0.3 | 1.0 |
| SEQ ID NO: 4 | Cry1A-R | ~0.3 | ~1 |
| | Cry1F-R | ~0.3 | ~1 |

Example 5: Transient Expression in Maize Leaves and Bioassay

Polynucleotides encoding MP448 (SEQ ID NO: 2) or MP627 (SEQ ID NO: 4) polypeptides were optimized for expression in maize and cloned behind the maize ubiquitin promoter (Christensen and Quail, (1996) *Transgenic Research* 5:213-218) in a transient expression vector. The agro-infiltration method of introducing an *Agrobacterium* cell suspension to plant cells of intact tissues so that reproducible infection and subsequent plant derived transgene expression may be measured or studied is well known in the art (Kapila, et. al., (1997) Plant Science 122:101-108). Briefly, young plantlets of maize were agro-infiltrated with normalized bacterial cell cultures of test and control strains. Leaf discs were generated from each plantlet and infested with sugarcane borer larvae (SCB—*Diatraea saccharalis*) along with appropriate controls. The degree of consumption of green leaf tissues was scored after 2 days of infestation.

The efficacy and expression level of MP448 and MP627 were evaluated in two independent assays. Three different MP448 and MP627 gene designs were tested. The Sugarcane borer efficacy results are shown in Table 6.

TABLE 6

| | MP448 | MP627 | Cry1A.88 | Negative control |
|---|---|---|---|---|
| SCB-1 | ++ | + | + | ++++ |
| SCB-2 | ++ | + | + | ++++ |

Data is represented as the average percent of leaf damage normalized against the negative control (+ = significant feeding protection and ++++ = no feeding protection).

Leaf disks from the same experiments were also fed to European corn borer (ECB) larvae. The European corn borer efficacy results are shown in Table 7.

TABLE 7

| | MP448 | MP627 | Cry1A.88 | Negative control |
|---|---|---|---|---|
| ECB-1 | ++ | + | + | ++++ |
| ECB-2 | ++ | + | + | ++++ |

Data is represented as the average percent of leaf damage normalized against the negative control (+ = significant feeding protection and ++++ = no feeding protection).

Example 6: Transformation and Regeneration of Transgenic Sugarcane Plants

For *Agrobacterium*-mediated transformation of sugarcane with a DNA construct comprising the polynucleotide of SEQ ID NO: 1 or SEQ ID NO: 3 the method of Cho was employed (U.S. Patent No. 2013/0055472 A1; the contents of which are hereby incorporated by reference). Briefly, callus/green sugarcane regenerative tissue was contacted with a suspension of *Agrobacterium* under conditions whereby the bacteria were capable of transferring the regulatory element sequence of the disclosure to at least one callus/green tissue cell (step 1: the infection step). The tissue was co-cultured with the *Agrobacterium* for a period of time (step 2: the co-cultivation step), then a "resting" step was performed. During this resting step, callus/green regenerative tissue was incubated in the presence of at least one antibiotic known to inhibit the growth of *Agrobacterium* without selecting for plant transformants (step 3: resting step). Next, tissue was transferred and cultured in the presence of a selective agent to recover growing, transformed material (step 4: the selection step). Plantlets were regenerated from surviving material (step 5: the regeneration step) prior to transfer to the greenhouse.

Example 7: *Agrobacterium*-Mediated Transformation of Maize and Regeneration of Transgenic Plants For *Agrobacterium*-mediated transformation of maize with a toxin nucleotide sequence (e.g., SEQ ID NO: 1 or SEQ ID NO: 3), the method of Zhao can be used (U.S. Pat. No. 5,981,840 and PCT patent publication WO98/32326; the contents of which are hereby incorporated by reference). Briefly, immature embryos are isolated from maize and the embryos contacted with a suspension of *Agrobacterium* under conditions whereby the bacteria are capable of transferring the toxin nucleotide sequence (SEQ ID NO: 1 or SEQ ID NO: 3) to at least one cell of at least one of the immature embryos (step 1: the infection step). In this step the immature embryos can be immersed in an *Agrobacterium* suspension for the initiation of inoculation. The embryos are co-cultured for a time with the *Agrobacterium* (step 2: the co-cultivation step). The immature embryos can be cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos can be cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium can be cultured on solid medium to regenerate the plants.

Example 8: Transformation of Soybean Embryos

Soybean embryos are bombarded with a plasmid containing the toxin nucleotide sequence of SEQ ID NO: 1 or SEQ ID NO: 3 operably linked to a suitable promoter as follows. To induce somatic embryos, cotyledons, 3-5 mm in length dissected from surface-sterilized, immature seeds of an appropriate soybean cultivar are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation includes, but is not limited to: the 35S promoter from Cauliflower Mosaic Virus (Odell, et al., (1985) Nature 313:810-812), the hygromycin phosphotransferase gene from plasmid pJR225 (from *E. coli*; Gritz, et al., (1983) Gene 25:179-188), and the 3' region of the nopaline synthase gene from the T DNA of the Ti plasmid of *Agrobacterium tumefaciens*. The expression cassette comprising a toxin nucleotide sequence (e.g., SEQ ID NO: 1) operably linked to a suitable promoter can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1M), and 50 µL CaCl2 (2.5M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications, patents and patent applications mentioned in the specification are indicative of the level of those skilled in the art to which this disclosure pertains. All publications, patents and patent applications are herein incorporated by reference to the same extent as if each individual publication, patent or patent application was specifically and individually indicated to be incorporated by reference.

Although the foregoing disclosure has been described in some detail by way of illustration and example for purposes of clarity of understanding, it will be obvious that certain changes and modifications may be practiced within the scope of the embodiments.

That which is claimed:

1. An isolated nucleic acid molecule selected from:
   (a) a polynucleotide encoding an insecticidal polypeptide having at least 97% amino acid sequence identity to SEQ ID NO: 2; and
   (b) a polynucleotide encoding an insecticidal polypeptide having at least 97% amino acid sequence identity to SEQ ID NO: 4, wherein the polynucleotide encoding the insecticidal polypeptide is operably linked to a heterologous regulatory element.

2. The isolated nucleic acid molecule of claim 1, wherein said nucleotide sequence is a synthetic sequence that has been designed for expression in a plant.

3. A DNA construct comprising the nucleic acid molecule of claim 1 operably linked to a heterologous regulatory element.

4. The DNA construct of claim 3, further comprising a nucleic acid molecule encoding a Cry crystal forming domain, a heterologous signal sequence or a heterologous transit peptide operably linked to the insecticidal polypeptide.

5. A host cell comprising the DNA construct of claim 3.

6. The host cell of claim 5 that is a bacterial cell.

7. The host cell of claim 5 that is a plant cell.

8. A transgenic plant comprising the DNA construct of claim 3.

9. The transgenic plant of claim 8, wherein said plant is selected from the group consisting of: maize, sorghum, wheat, cabbage, sunflower, tomato, crucifer, pepper, potato, cotton, rice, soybean, sugar beet, sugarcane, tobacco, barley, and oilseed rape.

10. The transgenic plant of claim 8, wherein the polynucleotide encoding the insecticidal polypeptide is stacked with a polynucleotide encoding a Cry protein.

11. The transgenic plant of claim 10, wherein the Cry protein is selected from a Cry1B, a Cry9, and a Cry1Ia14 protein.

12. Transformed seed of the plant of claim 8, wherein the seed comprise the DNA construct.

13. A recombinant insecticidal polypeptide operably linked to a heterologous signal sequence or transit polypeptide, wherein the insecticidal polypeptide comprises an amino acid sequence selected from:
   (a) an amino acid sequence having at least 97% sequence identity to SEQ ID NO: 2; or
   (b) an amino acid sequence having at least 97% sequence identity to SEQ ID NO: 4.

14. The insecticidal polypeptide of claim 13, further comprising a heterologous Cry crystal forming domain operably linked to the insecticidal polypeptide.

15. A composition comprising the insecticidal polypeptide of claim 14.

16. The composition of claim 15, wherein said composition is a powder, dust, pellet, granule, spray, emulsion, colloid, or solution.

17. The composition of claim 16, wherein said composition is prepared by desiccation, lyophilization, homogenization, extraction, filtration, centrifugation, sedimentation, or concentration of a culture of Bacillus thuringiensis cells.

18. The composition of claim 15, comprising from 1% to 99% by weight of the insecticidal polypeptide.

19. The composition of claim 15, wherein the composition further comprises an additional insecticidal polypeptide.

20. The composition of claim 15, wherein the additional insecticidal polypeptide is selected from a Cry1B, a Cry9, and a Cry1Ia14 protein.

21. A method for controlling a Lepidopteran pest population comprising contacting said population with a pesticidally-effective amount of the polypeptide of claim 14.

22. A method for killing a Lepidopteran pest comprising contacting said pest with, or feeding to said pest, a pesticidally-effective amount of the polypeptide of claim 14.

23. A method for producing a polypeptide with pesticidal activity, comprising culturing the host cell of claim 4 under conditions in which a nucleic acid molecule encoding the polypeptide is expressed, wherein said polypeptide being selected from the group consisting of:
   (a) a polypeptide having at least 97% sequence identity to the amino acid sequence of SEQ ID NO: 2; and
   (b) a polypeptide having at least 97% sequence identity to the amino acid sequence of SEQ ID NO: 4.

24. A method for protecting a plant from an insect pest, comprising introducing into said plant or cell thereof at least one expression vector comprising a nucleotide sequence that encodes a pesticidal polypeptide, wherein said nucleotide sequence is selected from the group consisting of:
   (a) a polynucleotide encoding a polypeptide having at least 97% sequence identity to the amino acid sequence of SEQ ID NO: 2; and
   (b) a polynucleotide encoding a polypeptide having at least 97% sequence identity to the amino acid sequence of SEQ ID NO: 4.

25. The method of claim 24, wherein the plant is sugarcane.

26. The method of claim 25, wherein the insect pest is a Lepidopteran.

27. The method of claim 26, wherein the insect pest is sugarcane borer (Diatraea sacchralis).

* * * * *

SEQUENCE LISTING

```
<160> NUMBER OF SEQ ID NOS: 60

<210> SEQ ID NO 1
<211> LENGTH: 2160
<212> TYPE: DNA
<213> ORGANISM: Bacillus thuringiensis

<400> SEQUENCE: 1
atgaaatcta agaatcaaaa tatgtatcaa agtttgtcta gcaatacgac agttgataaa        60
aactttacaa attcactaga aaacaacaca aatatggaat tacaaaatat taattatgaa       120
```

```
gattgtttga gaatgtctga gtatgaaggt atagagccgt tgttagtgt atcaacaatt      180 caaacaggta ttggtattgc gggtaaaata cttggtaccc taggcgttcc ttttgcagga      240
caagtagcta gtctttatag ttttatctta ggtgagctat ggcctaaggg gaaaagccaa      300
tgggaaatct ttatggaaca gtagaagag attattaatc aaaaaatatc aacttatgca       360
agaagtaaag cacttacaga cttgaaagga ttaggagatg ccttagctgt ctaccatgaa      420
tcgctggaaa gttgggttgg aaatcgtaat aacacaaggg ctaggagtgt tgtcaagagc      480
caatatatcg cattagaatt gatgttcgtt cagaaactac cttcttttgc agtgtctgga      540
gaggaggtaa cattattacc gatatatgcc caagctgcaa atttacattt gttgctatta      600
cgagatgcgt ctattttggg aaaagagtgg ggattatcat cttcagaaat ttcaacattt      660
tataaccgtc aagtcgaacg agcaggagat tattccgacc attgtgtgaa atggtatagc      720
acaggtctaa ataacttgag gggtacaaat gccgaaagtt gggtacgata taatcaattc      780
cgtagagaca tgactttaat ggtactagat ttagtggcac tatttccaag ctatgataca      840
caaatgtatc caattaaaac tacagcccaa cttacaagag aagtatatac agacgcaatt      900
gggacaatac atccgcatcc aagttttaca agtacgactt ggtataataa taatgcacct      960
tcgttctctg ccatagaggc tgctgttgtt cgaaacccgc atctactcga tttctagaa      1020 caagttacaa tttacagctt attaagtcga tggagtaaca ctcagtatat gaatatgtgg      1080
ggaggacata aactagaatt ccgaacaata ggaggaacgt taaataccta aacacaagga      1140
tctactaata ctgctattaa tcctgtaaca ttaccgttca cttcacgaga cgtctatagg      1200
actgaatcat tggcagggct gaatctattt ttaactcaac ctgttaatgg agtacctagg      1260
gttgattttc attggaaatt cgtcacacat ccgatcgcat ctgataattt ctattatcca      1320
gggtatgctg gaattgggac gcaattacag gattcagaaa atgaattacc atctgaagca      1380
acaggacagc caaattatga atcttatagt catagattat ctcatatagg actcatttca      1440
gcatcacatg tgaaagcatt ggtatattct tggacacatc gtagtgcaga tcgtacaaat      1500
acaattgagc caaatagcat tacacaaata ccattagtaa aagcgttcaa tctgtcttca      1560
ggtgccgctg tagtgagagg accaggattt acaggtgggg atatccttcg aagaacgaat      1620
actggtacat ttgggggatat acgagtaaat attaatccac catttgcaca aagatatcgc      1680
gtgaggattc gctatgcttc tactacagat ttacaattcc atacgtcaat taacggtaaa      1740
gctattaatc aaggtaattt ttcagcaact atgaatagag gagaggactt agactataaa      1800 accttagaa ctgtaggctt taccactcca tttagctttt cagatgtaca agtacattc       1860 acaataggtg cttggaactt ctcttcaggt aacgaagttt atatagatag aattgaattt      1920
gttccggtag aagtaactta tgaggcagaa tatgattttg aaaaagcgca agagaaggtt      1980
actgcactgt ttacatctac gaatccaaga ggattaaaaa cagatgtaaa ggattatcat      2040
attgaccagg tatcaaattt agtagagtct ctatcagatg aattctatct tgatgaaaag      2100
agagaattat tcgagatagt taaatacgcg aagcaaatcc atattgagcg taacatgtag      2160
```

<210> SEQ ID NO 2
<211> LENGTH: 719
<212> TYPE: PRT
<213> ORGANISM: Bacillus thuringiensis

<400> SEQUENCE: 2

```
Met Lys Ser Lys Asn Gln Asn Met Tyr Gln Ser Leu Ser Ser Asn Thr
1               5                   10                  15
```

```
Thr Val Asp Lys Asn Phe Thr Asn Ser Leu Glu Asn Asn Thr Asn Met
             20                  25                  30

Glu Leu Gln Asn Ile Asn Tyr Glu Asp Cys Leu Arg Met Ser Glu Tyr
         35                  40                  45

Glu Gly Ile Glu Pro Phe Val Ser Val Ser Thr Ile Gln Thr Gly Ile
 50                  55                  60

Gly Ile Ala Gly Lys Ile Leu Gly Thr Leu Gly Val Pro Phe Ala Gly
 65                  70                  75                  80

Gln Val Ala Ser Leu Tyr Ser Phe Ile Leu Gly Glu Leu Trp Pro Lys
             85                  90                  95

Gly Lys Ser Gln Trp Glu Ile Phe Met Glu His Val Glu Glu Ile Ile
            100                 105                 110

Asn Gln Lys Ile Ser Thr Tyr Ala Arg Ser Lys Ala Leu Thr Asp Leu
            115                 120                 125

Lys Gly Leu Gly Asp Ala Leu Ala Val Tyr His Glu Ser Leu Glu Ser
130                 135                 140

Trp Val Gly Asn Arg Asn Asn Thr Arg Ala Arg Ser Val Val Lys Ser
145                 150                 155                 160

Gln Tyr Ile Ala Leu Glu Leu Met Phe Val Gln Lys Leu Pro Ser Phe
            165                 170                 175

Ala Val Ser Gly Glu Glu Val Thr Leu Leu Pro Ile Tyr Ala Gln Ala
            180                 185                 190

Ala Asn Leu His Leu Leu Leu Arg Asp Ala Ser Ile Phe Gly Lys
            195                 200                 205

Glu Trp Gly Leu Ser Ser Ser Glu Ile Ser Thr Phe Tyr Asn Arg Gln
            210                 215                 220

Val Glu Arg Ala Gly Asp Tyr Ser Asp His Cys Val Lys Trp Tyr Ser
225                 230                 235                 240

Thr Gly Leu Asn Asn Leu Arg Gly Thr Asn Ala Glu Ser Trp Val Arg
            245                 250                 255

Tyr Asn Gln Phe Arg Arg Asp Met Thr Leu Met Val Leu Asp Leu Val
            260                 265                 270

Ala Leu Phe Pro Ser Tyr Asp Thr Gln Met Tyr Pro Ile Lys Thr Thr
            275                 280                 285

Ala Gln Leu Thr Arg Glu Val Tyr Thr Asp Ala Ile Gly Thr Ile His
            290                 295                 300

Pro His Pro Ser Phe Thr Ser Thr Trp Tyr Asn Asn Asn Ala Pro
305                 310                 315                 320

Ser Phe Ser Ala Ile Glu Ala Ala Val Val Arg Asn Pro His Leu Leu
            325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
            355                 360                 365

Thr Ile Gly Gly Thr Leu Asn Thr Ser Thr Gln Gly Ser Thr Asn Thr
            370                 375                 380

Ala Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
            405                 410                 415

Gly Val Pro Arg Val Asp Phe His Trp Lys Phe Val Thr His Pro Ile
            420                 425                 430

Ala Ser Asp Asn Phe Tyr Tyr Pro Gly Tyr Ala Gly Ile Gly Thr Gln
```

```
                435                 440                 445
Leu Gln Asp Ser Glu Asn Glu Leu Pro Ser Glu Ala Thr Gly Gln Pro
    450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525

Gly Phe Thr Gly Gly Asp Ile Leu Arg Arg Thr Asn Thr Gly Thr Phe
    530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
        595                 600                 605

Thr Pro Phe Ser Phe Ser Asp Val Gln Ser Thr Phe Thr Ile Gly Ala
    610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Glu Phe Tyr Leu Asp Glu Lys Arg Glu Leu Phe
    690                 695                 700

Glu Ile Val Lys Tyr Ala Lys Gln Ile His Ile Glu Arg Asn Met
705                 710                 715

<210> SEQ ID NO 3
<211> LENGTH: 2082
<212> TYPE: DNA
<213> ORGANISM: Bacillus thuringiensis

<400> SEQUENCE: 3
atgaatcgaa ataatcaaaa tgaatatgaa gttattgatg cttccacttg cgggtgcccg       60
tcagatgatg ttgtaaaata tcctttgaca gatgatccga atgctggatt gcaaaatatg      120
aactataagg aatatttaca atgtatggt ggagactata cagatcctct tatcaaccct       180
aacttacctg ttagtggaaa agatgtaata caagttggaa ttaatattgt agggagatta      240
cttagctttt ttggattccc cttttctagt caatgggttg ctgtatatac ccatctttta      300
aacagcttgt ggccggatga tgagaattct gtatgggatg cttttatgaa gagagtagaa      360
gaacttattg atcaaaaaat cgcagaagca gtacatggtc tggcattgga tcacctaact      420
ggattacaac ataattataa tttatatgta gaagcattag atgagtggct gaatagaccg      480 aatgggggcaa gggcagcctt agtttctcag cgatttaaca atttagatag cctatttaca      540
```

-continued

```
caatttatgc ctagctttgg ctctggtcct ggaagtcgaa attatgcaac tatattactt    600
ccagtatatg cacaagcagc aaaccttcat ttgttattat taaaagatgt agacattttat   660
ggagctagat gggggctgaa tcaaactcaa atagatctat tccattctcg tcaacaaggg    720
cttactcaga cttatacaaa tcattgtgtt actgcgtata atgatggatt agcggaatta    780
agaggcacaa gcgttgagag ttggctcaaa tatcatcaat accgtaggga aatgacagta    840
acggcaatgg atttagtggc attattccca tactataatg ttcgacaata tccaaatggg    900
gcaaatccac aacttacacg tgaggtatat acagatccaa tcgtatttaa tccgcctaag    960
cctccaagtg gcgctttctg cgaaagtttt tatactatcc gagcggcacg agaacgttta   1020
acttttcgc aacttgaaaa tgcaataatt cgtccaccgc gcttgtttga aaggtttcaa    1080
gcattaggga tttatacaca cgaggcgaga ctgaatcaaa atagtgctcc aatgaactat   1140
tggattggac attttataag aaatactcgt ttgggtgact caacaacaat tacttcaaat   1200
tatgaacaa ccaataatcg tttaactaat ttcactcctc ctactaacag tgatgtttat    1260
caaattaatt caatctcaag taatttagcc gctattttag gcactatatt tggggttact   1320
aacgcagcat tccatcatgg atcaggaaat atttggtcgt atgtcggaca aaataacgtt   1380
cttgcacaat gtcatcaaaa ctataattca atagaagaat taccaaacca aagcgatgaa   1440
cctacagtta gaagttatag ccatagatta tctcatatca cctcttttaa tttcaatgta   1500
cagcttaata atcctgtact ctctactggc aatatgcctg tatatgtgtg acacatcgc    1560
ggtgtggacc ttaataacac gattacttca gatagaatta ctcaattacc attggtaaag   1620
gcatctgaac ttgttgcagg tactactgtc gtgaaaggac caggattcac aggaggagat   1680
atacttcgaa gaacgagcaa tggtaatttt ggaacaataa gagtaatggt tagttcacca   1740
ttaacacaac aatatcgcct aagagttcgt tatgcctcaa caggaaattt cagcatagtg   1800
gtaagacgtg gaagcactac tgtaggtaat attagagtcc caagtacaat gaacagggga   1860
gcggaattca ggtacgaatc cttttgacacg agagagttta ctactactgg tccgcagaat   1920
ccgccttta catttacaca aactcaagag agtctaacag tggctgcaga aggtgttagc     1980
accggtagtg aatattttat agatcgaatt gaaatcatcc ctgtaaatcc gacacgagaa   2040
gcggaagagg atttagaagc agcgaagaaa gcggtggcgt aa                       2082
```

<210> SEQ ID NO 4
<211> LENGTH: 693
<212> TYPE: PRT
<213> ORGANISM: Bacillus thuringiensis

<400> SEQUENCE: 4

```
Met Asn Arg Asn Asn Gln Asn Glu Tyr Glu Val Ile Asp Ala Ser Thr
1               5                   10                  15

Cys Gly Cys Pro Ser Asp Asp Val Val Lys Tyr Pro Leu Thr Asp Asp
                20                  25                  30

Pro Asn Ala Gly Leu Gln Asn Met Asn Tyr Lys Glu Tyr Leu Gln Met
            35                  40                  45

Tyr Gly Gly Asp Tyr Thr Asp Pro Leu Ile Asn Pro Asn Leu Pro Val
        50                  55                  60

Ser Gly Lys Asp Val Ile Gln Val Gly Ile Asn Ile Val Gly Arg Leu
65                  70                  75                  80

Leu Ser Phe Phe Gly Phe Pro Phe Ser Ser Gln Trp Val Ala Val Tyr
                85                  90                  95

Thr His Leu Leu Asn Ser Leu Trp Pro Asp Asp Glu Asn Ser Val Trp
```

-continued

```
                100             105             110
Asp Ala Phe Met Lys Arg Val Glu Glu Leu Ile Asp Gln Lys Ile Ala
            115                 120                 125
Glu Ala Val His Gly Leu Ala Leu Asp His Leu Thr Gly Leu Gln His
            130                 135                 140
Asn Tyr Asn Leu Tyr Val Glu Ala Leu Asp Glu Trp Leu Asn Arg Pro
145                 150                 155                 160
Asn Gly Ala Arg Ala Leu Val Ser Gln Arg Phe Asn Asn Leu Asp
            165                 170                 175
Ser Leu Phe Thr Gln Phe Met Pro Ser Phe Gly Ser Gly Pro Gly Ser
            180                 185                 190
Arg Asn Tyr Ala Thr Ile Leu Leu Pro Val Tyr Ala Gln Ala Ala Asn
            195                 200                 205
Leu His Leu Leu Leu Lys Asp Val Asp Ile Tyr Gly Ala Arg Trp
            210                 215                 220
Gly Leu Asn Gln Thr Gln Ile Asp Leu Phe His Ser Arg Gln Gln Gly
225                 230                 235                 240
Leu Thr Gln Thr Tyr Thr Asn His Cys Val Thr Ala Tyr Asn Asp Gly
            245                 250                 255
Leu Ala Glu Leu Arg Gly Thr Ser Val Glu Ser Trp Leu Lys Tyr His
            260                 265                 270
Gln Tyr Arg Arg Glu Met Thr Val Thr Ala Met Asp Leu Val Ala Leu
            275                 280                 285
Phe Pro Tyr Tyr Asn Val Arg Gln Tyr Pro Asn Gly Ala Asn Pro Gln
            290                 295                 300
Leu Thr Arg Glu Val Tyr Thr Asp Pro Ile Val Phe Asn Pro Pro Lys
305                 310                 315                 320
Pro Pro Ser Gly Ala Phe Cys Glu Ser Phe Tyr Thr Ile Arg Ala Ala
            325                 330                 335
Arg Glu Arg Leu Thr Phe Ser Gln Leu Glu Asn Ala Ile Ile Arg Pro
            340                 345                 350
Pro Arg Leu Phe Glu Arg Phe Gln Ala Leu Gly Ile Tyr Thr His Glu
            355                 360                 365
Ala Arg Leu Asn Gln Asn Ser Ala Pro Met Asn Tyr Trp Ile Gly His
            370                 375                 380
Phe Ile Arg Asn Thr Arg Leu Gly Asp Ser Thr Thr Ile Thr Ser Asn
385                 390                 395                 400
Tyr Gly Thr Thr Asn Asn Arg Leu Thr Asn Phe Thr Pro Thr Asn
            405                 410                 415
Ser Asp Val Tyr Gln Ile Asn Ser Ile Ser Ser Asn Leu Ala Ala Ile
            420                 425                 430
Leu Gly Thr Ile Phe Gly Val Thr Asn Ala Ala Phe His His Gly Ser
            435                 440                 445
Gly Asn Ile Trp Ser Tyr Val Gly Gln Asn Asn Val Leu Ala Gln Cys
            450                 455                 460
His Gln Asn Tyr Asn Ser Ile Glu Glu Leu Pro Asn Gln Ser Asp Glu
465                 470                 475                 480
Pro Thr Val Arg Ser Tyr Ser His Arg Leu Ser His Ile Thr Ser Phe
            485                 490                 495
Asn Phe Asn Val Gln Leu Asn Asn Pro Val Leu Ser Thr Gly Asn Met
            500                 505                 510
Pro Val Tyr Val Trp Thr His Arg Gly Val Asp Leu Asn Asn Thr Ile
            515                 520                 525
```

-continued

```
Thr Ser Asp Arg Ile Thr Gln Leu Pro Leu Val Lys Ala Ser Glu Leu
    530                 535                 540

Val Ala Gly Thr Thr Val Val Lys Gly Pro Gly Phe Thr Gly Gly Asp
545                 550                 555                 560

Ile Leu Arg Arg Thr Ser Asn Gly Asn Phe Gly Thr Ile Arg Val Met
                565                 570                 575

Val Ser Ser Pro Leu Thr Gln Gln Tyr Arg Leu Arg Val Arg Tyr Ala
            580                 585                 590

Ser Thr Gly Asn Phe Ser Ile Val Val Arg Arg Gly Ser Thr Thr Val
        595                 600                 605

Gly Asn Ile Arg Val Pro Ser Thr Met Asn Arg Gly Ala Glu Phe Arg
    610                 615                 620

Tyr Glu Ser Phe Asp Thr Arg Glu Phe Thr Thr Thr Gly Pro Gln Asn
625                 630                 635                 640

Pro Pro Phe Thr Phe Thr Gln Thr Gln Glu Ser Leu Thr Val Ala Ala
                645                 650                 655

Glu Gly Val Ser Thr Gly Ser Glu Tyr Phe Ile Asp Arg Ile Glu Ile
            660                 665                 670

Ile Pro Val Asn Pro Thr Arg Glu Ala Glu Glu Asp Leu Glu Ala Ala
        675                 680                 685

Lys Lys Ala Val Ala
    690
```

<210> SEQ ID NO 5
<211> LENGTH: 3531
<212> TYPE: DNA
<213> ORGANISM: Bacillus thuringiensis

<400> SEQUENCE: 5

```
atgaatcgaa ataatcaaaa tgaatatgaa gttattgatg cttccacttg cgggtgcccg     60
tcagatgatg ttgtaaaata tcctttgaca gatgatccga atgctggatt gcaaaatatg    120
aactataagg aatatttaca aatgtatggt ggagactata cagatcctct tatcaaccct    180
aacttacctg ttagtggaaa agatgtaata caagttggaa ttaatattgt agggagatta    240
ctaagctttt ttggattccc cttttctagt caatgggttg ctgtatatac ccatctttta    300
aacagcttgt ggccggatga tgagaattct gtatgggatg cttttatgaa gagagtagaa    360
gaacttattg atcaaaaaat cgcagaagca gtacatggtc tggcattgga tcacctaact    420
ggattacaac ataattataa tttatatgta gaagcattag atgagtggct gaatagaccg    480
aatggggcaa gggcagcctt agtttctcag cgatttaaca atttagatag cctatttaca    540
caatttatgc caagctttgg ctctggtcct ggaagtcgaa attatgcaac tatattactt    600
ccagtatatg cacaagcagc aaaccttcat ttgttattat taaaagatgt agacatttat    660
ggagctagat gggggctgaa tcaaactcaa atagatctat tccattctcg tcaacaaggg    720
cttactcaga cttatacaaa tcattgtgtt actgcgtata atgatggatt agcggaatta    780
agaggcacaa gcgttgagag ttggctcaaa tatcatcaat accgtaggga aatgacagta    840
acggcaatgg atttagtggc attattccca tactataatg ttcgacaata tccaaatggg    900
gcaaatccac aacttacacg tgaggtatat acagatccaa tcgtatttaa tccgcctaag    960
cctccaagtg gcgctttctg cgaaagtttt tatactatcc gagcggctcg agaacgttta   1020
actttttcgc aacttgaaaa tgcaataatt cgtccaccgc gcttgtttga aaggtttcaa   1080
gctttaggga tttatacaca cgaggcgaga ctgaatcaaa atagtgctcc aatgaactat   1140
```

```
tggattggac attttataag aaatactcgt ttgggtgact caacaacaat tacttcaaat    1200 tatgaacaa ccaataatcg tttaactaat ttcactcctc ctactaacag tgatgtttat    1260
caaattaatt caatctcaag taatttagcc gctattttag cactatatt tggggttact    1320 aacgcagcat tccatcatgg atcaggaaat atttggtcgt atgtcggaca aaataacgtt    1380
cttgcacaat gtcatcaaaa ctataattca atagaagaat taccaaacca aagcgatgaa    1440
cctacagtta gaagttatag ccatagatta tctcatatca cctctttaa tttcaatgta    1500 cagcttaata atcctgtact ctctactggc aatatgcctg tatatgtgtg gacacatcgc    1560
ggtgtggacc ttaataacac gattacttca gatagaatta ctcaattacc attggtaaag    1620
gcatctgaac ttgttgcagg tactactgtc gtgaaaggac caggattcac aggaggagat    1680
atacttcgaa gaacgagcaa tggtaatttt ggaacaataa gagtaatggt tagttcacca    1740
ttaacacaac aatatcgcct aagagttcgt tatgcctcaa caggaaattt cagcatagtg    1800
gtaagacgtg gaagcactac tgtaggtaat attagagtcc caagtacaat gaacagggga    1860
gcggaattca ggtacgaatc ctttgacacg agagagttta ctactactgg tccgcagaat    1920
ccgcctttta catttacaca aactcaagag agtctaacag tggctgcaga aggtgttagc    1980
accggtagtg aatattttat agatcgaatt gaaatcatcc ctgtaaatcc gacacgagaa    2040
gcggaagagg atttagaagc agcgaagaaa gcggtggcga gcttgtttac acgtactaga    2100
gatggattac aggtgaatgt gacagattac caagtcgatc aggcggcaaa tttagtgtca    2160
tgcttatcag atgaacaata tgggcatgac aaaaagatgt tattagaagc ggtacgcgcg    2220
gcaaaacgcc tctgccgcga acacaacttg cttcaagatc cagattttaa tgaaataaat    2280 agtacgaag agaatggctg gaaggcaagt aacggcgtta ctattagcga gggcggtcca    2340
ttctttaaag gccgtgcact tcagttagca agcgcaagag aaaattatcc aacatacatt    2400
tatcaaaagg tagtgcatc ggcgttaaag ccttatacac gctatagact ggatggattt    2460
gtgaagagta gtcaagattt agaaattgat ctcattcacc aaaataaagt ccatcttgta    2520
aaaaatgtac cagataattt agtatttgat acttacccag atggttcttg cagtggaatt    2580
aatcgatgtg aggaacaaca gatggtaaat acgcaactgg aaacagaaca gcatcatccg    2640
atggattgct gtgaagcggc ccaagcacat gagttttctt cctatattaa tacaggggat    2700
ttaaattcag gtgtagatca gggcatctgg gttgtattga agttcgaac aacagatggt    2760 tatgcaacgt taggaaatct tgaattggta gaagttggac cattatcagg tgaatcccta    2820
gaacatgaaa aagaaaaaa tgcggaatgg aatgcagagt taggaagaaa gcttgcagaa    2880
acagatcgcg tgtatcaagc tgcgaaacaa gcaattaatc atctatttgt agactatcaa    2940
gatcaacaat taaatccgga aatagggcta acggagatta atgaagtctc aaatcttgtg    3000
gagtcaattc cgggtgtata tagtgataca gtattgcaaa tccctggaat taactacgag    3060
atttacaaag agttatccga tcgattacaa caagcatcga atctgtacac gtctcgaaat    3120
gctgtgcaaa acggcgactt tgacagtggg ttagatggtt ggaacgcaac aacggataca    3180
tcggttcagc aggatggcaa tatgcatttc ttggttcttt cccattggga tgcacaagtt    3240
tcccaacaat tgagagtaca cccgaactgt aagtatgtct tacgtgtgac agcaagaaaa    3300
gtgggaggcg gcgatgggta cgtcacaatc cgagatggcg ctcatcacca aaaaaacctt    3360
acatttaatg catgtgatta cgatgtaaat ggtacgtatg tagatgataa tacgtatata    3420
acaaaagatg tgatattcta cccagagaca aaacatatgt gggtagaggt gagtgaatcc    3480
```

```
gaaggttcat tctatgtaga tagtattgag tttattgaaa cacaagagta g        3531
```

<210> SEQ ID NO 6
<211> LENGTH: 1176
<212> TYPE: PRT
<213> ORGANISM: Bacillus thuringiensis

<400> SEQUENCE: 6

```
Met Asn Arg Asn Asn Gln Asn Glu Tyr Glu Val Ile Asp Ala Ser Thr
1               5                   10                  15

Cys Gly Cys Pro Ser Asp Val Val Lys Tyr Pro Leu Thr Asp Asp
            20                  25                  30

Pro Asn Ala Gly Leu Gln Asn Met Asn Tyr Lys Glu Tyr Leu Gln Met
        35                  40                  45

Tyr Gly Gly Asp Tyr Thr Asp Pro Leu Ile Asn Pro Asn Leu Pro Val
    50                  55                  60

Ser Gly Lys Asp Val Ile Gln Val Gly Ile Asn Ile Val Gly Arg Leu
65                  70                  75                  80

Leu Ser Phe Phe Gly Phe Pro Phe Ser Ser Gln Trp Val Ala Val Tyr
                85                  90                  95

Thr His Leu Leu Asn Ser Leu Trp Pro Asp Asp Glu Asn Ser Val Trp
            100                 105                 110

Asp Ala Phe Met Lys Arg Val Glu Glu Leu Ile Asp Gln Lys Ile Ala
        115                 120                 125

Glu Ala Val His Gly Leu Ala Leu Asp His Leu Thr Gly Leu Gln His
    130                 135                 140

Asn Tyr Asn Leu Tyr Val Glu Ala Leu Asp Glu Trp Leu Asn Arg Pro
145                 150                 155                 160

Asn Gly Ala Arg Ala Ala Leu Val Ser Gln Arg Phe Asn Asn Leu Asp
                165                 170                 175

Ser Leu Phe Thr Gln Phe Met Pro Ser Phe Gly Ser Gly Pro Gly Ser
            180                 185                 190

Arg Asn Tyr Ala Thr Ile Leu Leu Pro Val Tyr Ala Gln Ala Ala Asn
        195                 200                 205

Leu His Leu Leu Leu Lys Asp Val Asp Ile Tyr Gly Ala Arg Trp
    210                 215                 220

Gly Leu Asn Gln Thr Gln Ile Asp Leu Phe His Ser Arg Gln Gln Gly
225                 230                 235                 240

Leu Thr Gln Thr Tyr Thr Asn His Cys Val Thr Ala Tyr Asn Asp Gly
                245                 250                 255

Leu Ala Glu Leu Arg Gly Thr Ser Val Glu Ser Trp Leu Lys Tyr His
            260                 265                 270

Gln Tyr Arg Arg Glu Met Thr Val Thr Ala Met Asp Leu Val Ala Leu
        275                 280                 285

Phe Pro Tyr Tyr Asn Val Arg Gln Tyr Pro Asn Gly Ala Asn Pro Gln
    290                 295                 300

Leu Thr Arg Glu Val Tyr Thr Asp Pro Ile Val Phe Asn Pro Pro Lys
305                 310                 315                 320

Pro Pro Ser Gly Ala Phe Cys Glu Ser Phe Tyr Thr Ile Arg Ala Ala
                325                 330                 335

Arg Glu Arg Leu Thr Phe Ser Gln Leu Glu Asn Ala Ile Ile Arg Pro
            340                 345                 350

Pro Arg Leu Phe Glu Arg Phe Gln Ala Leu Gly Ile Tyr Thr His Glu
        355                 360                 365
```

-continued

```
Ala Arg Leu Asn Gln Asn Ser Ala Pro Met Asn Tyr Trp Ile Gly His
    370                 375                 380

Phe Ile Arg Asn Thr Arg Leu Gly Asp Ser Thr Thr Ile Thr Ser Asn
385                 390                 395                 400

Tyr Gly Thr Thr Asn Asn Arg Leu Thr Asn Phe Thr Pro Pro Thr Asn
                    405                 410                 415

Ser Asp Val Tyr Gln Ile Asn Ser Ile Ser Ser Asn Leu Ala Ala Ile
                420                 425                 430

Leu Gly Thr Ile Phe Gly Val Thr Asn Ala Ala Phe His His Gly Ser
            435                 440                 445

Gly Asn Ile Trp Ser Tyr Val Gly Gln Asn Asn Val Leu Ala Gln Cys
        450                 455                 460

His Gln Asn Tyr Asn Ser Ile Glu Glu Leu Pro Asn Gln Ser Asp Glu
465                 470                 475                 480

Pro Thr Val Arg Ser Tyr Ser His Arg Leu Ser His Ile Thr Ser Phe
                    485                 490                 495

Asn Phe Asn Val Gln Leu Asn Asn Pro Val Leu Ser Thr Gly Asn Met
                500                 505                 510

Pro Val Tyr Val Trp Thr His Arg Gly Val Asp Leu Asn Asn Thr Ile
            515                 520                 525

Thr Ser Asp Arg Ile Thr Gln Leu Pro Leu Val Lys Ala Ser Glu Leu
        530                 535                 540

Val Ala Gly Thr Thr Val Val Lys Gly Pro Gly Phe Thr Gly Gly Asp
545                 550                 555                 560

Ile Leu Arg Arg Thr Ser Asn Gly Asn Phe Gly Thr Ile Arg Val Met
                    565                 570                 575

Val Ser Ser Pro Leu Thr Gln Gln Tyr Arg Leu Arg Val Arg Tyr Ala
                580                 585                 590

Ser Thr Gly Asn Phe Ser Ile Val Val Arg Arg Gly Ser Thr Thr Val
            595                 600                 605

Gly Asn Ile Arg Val Pro Ser Thr Met Asn Arg Gly Ala Glu Phe Arg
        610                 615                 620

Tyr Glu Ser Phe Asp Thr Arg Glu Phe Thr Thr Thr Gly Pro Gln Asn
625                 630                 635                 640

Pro Pro Phe Thr Phe Thr Gln Thr Gln Glu Ser Leu Thr Val Ala Ala
                    645                 650                 655

Glu Gly Val Ser Thr Gly Ser Glu Tyr Phe Ile Asp Arg Ile Glu Ile
                660                 665                 670

Ile Pro Val Asn Pro Thr Arg Glu Ala Glu Glu Asp Leu Glu Ala Ala
            675                 680                 685

Lys Lys Ala Val Ala Ser Leu Phe Thr Arg Thr Arg Asp Gly Leu Gln
        690                 695                 700

Val Asn Val Thr Asp Tyr Gln Val Asp Gln Ala Ala Asn Leu Val Ser
705                 710                 715                 720

Cys Leu Ser Asp Glu Gln Tyr Gly His Asp Lys Lys Met Leu Leu Glu
                    725                 730                 735

Ala Val Arg Ala Ala Lys Arg Leu Cys Arg Glu His Asn Leu Leu Gln
                740                 745                 750

Asp Pro Asp Phe Asn Glu Ile Asn Ser Thr Glu Glu Asn Gly Trp Lys
            755                 760                 765

Ala Ser Asn Gly Val Thr Ile Ser Glu Gly Gly Pro Phe Phe Lys Gly
        770                 775                 780

Arg Ala Leu Gln Leu Ala Ser Ala Arg Glu Asn Tyr Pro Thr Tyr Ile
```

```
            785                 790                 795                 800
        Tyr Gln Lys Val Asp Ala Ser Ala Leu Lys Pro Tyr Thr Arg Tyr Arg
                        805                 810                 815
        Leu Asp Gly Phe Val Lys Ser Ser Gln Asp Leu Glu Ile Asp Leu Ile
                        820                 825                 830
        His Gln Asn Lys Val His Leu Val Lys Asn Val Pro Asp Asn Leu Val
                        835                 840                 845
        Phe Asp Thr Tyr Pro Asp Gly Ser Cys Ser Gly Ile Asn Arg Cys Glu
                        850                 855                 860
        Glu Gln Gln Met Val Asn Thr Gln Leu Glu Thr Glu Gln His His Pro
        865                 870                 875                 880
        Met Asp Cys Cys Glu Ala Ala Gln Ala His Glu Phe Ser Ser Tyr Ile
                        885                 890                 895
        Asn Thr Gly Asp Leu Asn Ser Gly Val Asp Gln Gly Ile Trp Val Val
                        900                 905                 910
        Leu Lys Val Arg Thr Thr Asp Gly Tyr Ala Thr Leu Gly Asn Leu Glu
                        915                 920                 925
        Leu Val Glu Val Gly Pro Leu Ser Gly Glu Ser Leu Glu His Glu Lys
                        930                 935                 940
        Arg Lys Asn Ala Glu Trp Asn Ala Glu Leu Gly Arg Lys Leu Ala Glu
        945                 950                 955                 960
        Thr Asp Arg Val Tyr Gln Ala Ala Lys Gln Ala Ile Asn His Leu Phe
                        965                 970                 975
        Val Asp Tyr Gln Asp Gln Gln Leu Asn Pro Glu Ile Gly Leu Thr Glu
                        980                 985                 990
        Ile Asn Glu Val Ser Asn Leu Val  Glu Ser Ile Pro Gly  Val Tyr Ser
                        995                 1000                1005
        Asp Thr Val Leu Gln Ile Pro  Gly Ile Asn Tyr Glu  Ile Tyr Lys
                1010                1015                1020
        Glu Leu Ser Asp Arg Leu Gln  Gln Ala Ser Asn Leu  Tyr Thr Ser
                1025                1030                1035
        Arg Asn Ala Val Gln Asn Gly  Asp Phe Asp Ser Gly  Leu Asp Gly
                1040                1045                1050
        Trp Asn Ala Thr Thr Asp Thr  Ser Val Gln Gln Asp  Gly Asn Met
                1055                1060                1065
        His Phe Leu Val Leu Ser His  Trp Asp Ala Gln Val  Ser Gln Gln
                1070                1075                1080
        Leu Arg Val His Pro Asn Cys  Lys Tyr Val Leu Arg  Val Thr Ala
                1085                1090                1095
        Arg Lys Val Gly Gly Gly Asp  Gly Tyr Val Thr Ile  Arg Asp Gly
                1100                1105                1110
        Ala His His Gln Lys Asn Leu  Thr Phe Asn Ala Cys  Asp Tyr Asp
                1115                1120                1125
        Val Asn Gly Thr Tyr Val Asp  Asp Asn Thr Tyr Ile  Thr Lys Asp
                1130                1135                1140
        Val Ile Phe Tyr Pro Glu Thr  Lys His Met Trp Val  Glu Val Ser
                1145                1150                1155
        Glu Ser Glu Gly Ser Phe Tyr  Val Asp Ser Ile Glu  Phe Ile Glu
                1160                1165                1170
        Thr Gln Glu
                1175

<210> SEQ ID NO 7
```

<211> LENGTH: 657
<212> TYPE: PRT
<213> ORGANISM: Bacillus thuringiensis

<400> SEQUENCE: 7

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
                20                  25                  30

Ala Arg Ile Glu Asp Ser Leu Cys Ile Ala Glu Gly Asn Asn Ile Asn
            35                  40                  45

Pro Leu Val Ser Ala Ser Thr Val Gln Thr Gly Ile Asn Ile Ala Gly
50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
                100                 105                 110

Thr Glu Asn Thr Arg Asn Thr Ala Ile Ala Arg Leu Glu Gly Leu Gly
            115                 120                 125

Arg Gly Tyr Arg Ser Tyr Gln Gln Ala Leu Glu Thr Trp Leu Asp Asn
130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Trp Gly Met
            195                 200                 205

Ala Ser Ser Asp Val Asn Gln Tyr Tyr Gln Glu Gln Ile Arg Tyr Thr
210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Thr Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
                340                 345                 350

Met Asn Tyr Trp Val Gly His Arg Leu Asn Phe Arg Pro Ile Gly Gly
            355                 360                 365

Thr Leu Asn Thr Ser Thr Gln Gly Leu Thr Asn Asn Thr Ser Ile Asn
370                 375                 380

Pro Val Thr Leu Gln Phe Thr Ser Arg Asp Val Tyr Arg Thr Glu Ser
```

```
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
    450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495

Thr Asn Thr Ile Gly Pro Asn Arg Ile Thr Gln Ile Pro Ala Val Lys
            500                 505                 510

Gly Arg Phe Leu Phe Asn Gly Ser Val Ile Ser Gly Pro Gly Phe Thr
        515                 520                 525

Gly Gly Asp Val Val Arg Leu Asn Arg Asn Asn Gly Asn Ile Gln Asn
    530                 535                 540

Arg Gly Tyr Ile Glu Val Pro Ile Gln Phe Thr Ser Thr Ser Thr Arg
545                 550                 555                 560

Tyr Arg Val Arg Val Arg Tyr Ala Ser Val Thr Ser Ile Glu Leu Asn
                565                 570                 575

Val Asn Leu Gly Asn Ser Ser Ile Phe Thr Asn Thr Leu Pro Ala Thr
            580                 585                 590

Ala Ala Ser Leu Asp Asn Leu Gln Ser Gly Asp Phe Gly Tyr Val Glu
        595                 600                 605

Ile Asn Asn Ala Phe Thr Ser Ala Thr Gly Asn Ile Val Gly Ala Arg
    610                 615                 620

Asn Phe Ser Ala Asn Ala Glu Val Ile Ile Asp Arg Phe Glu Phe Ile
625                 630                 635                 640

Pro Val Thr Ala Thr Phe Glu Ala Glu Tyr Asp Leu Glu Arg Ala Gln
                645                 650                 655

Lys
```

<210> SEQ ID NO 8
<211> LENGTH: 1971
<212> TYPE: DNA
<213> ORGANISM: Bacillus thuringiensis

<400> SEQUENCE: 8

```
atgccttcaa ataggaaaaa tgagaatgaa attataaatg ccttatcgat tccagctgta     60
tcgaatcatt ccgcacaaat ggatctatcg ctagatgctc gtattgagga ttctttgtgt    120
atagccgagg ggaataatat caatccactt gttagcgcat caacagtcca aacgggtata    180
aacatagctg gtagaatatt gggcgtatta ggtgtgccgt ttgctggaca actagctagt    240
ttttatagtt ttcttgttgg ggaattatgg cctagtggca gagatccatg ggaaattttc    300
ctggaacatg tagaacaact tataagacaa caagtaacag aaaatactag gaatacggct    360
attgctcgat tagaaggtct aggaagaggc tatagatctt accagcaggc tcttgaaact    420
tggttagata accgaaatga tgcaagatca agaagcatta ttcttgagcg ctatgttgct    480
ttagaacttg acattactac tgctataccg cttttcagaa tacgaaatga agaagttcca    540
ttattaatgg tatatgctca agctgcaaat ttacacctat tattattgag agacgcatcc    600
```

```
cttttttggta gtgaatgggg gatggcatct tccgatgtta accaatatta ccaagaacaa    660
atcagatata cagaggaata ttctaaccat tgcgtacaat ggtataatac agggctaaat    720
aacttaagag ggacaaatgc tgaaagttgg ttgcggtata atcaattccg tagagaccta    780
acgttagggg tattagattt agtagcccta ttcccaagct atgatactcg cacttatcca    840
atcaatacga gtgctcagtt aacaagagaa atttatacag atccaattgg gagaacaaat    900
gcaccttcag gatttgcaag tacgaattgg tttaataata atgcaccatc gttttctgcc    960
atagaggctg ccattttcag gcctccgcat ctacttgatt ttccagaaca acttacaatt   1020
tacagtgcat caagccgttg gagtagcact caacatatga attattgggt gggacatagg   1080
cttaacttcc gcccaatagg agggacatta aatacctcaa cacaaggact tactaataat   1140
acttcaatta atcctgtaac attacagttt acgtctcgtg acgtttatag aacagaatca   1200
aatgcaggga caaatatact atttactact cctgtgaatg gagtaccttg ggctagattt   1260
aattttataa accctcagaa tatttatgaa agaggcgcca ctacctacag tcaaccgtat   1320
cagggagttg ggattcaatt atttgattca gaaactgaat taccaccaga aacaacagaa   1380
cgaccaaatt atgaatcata tagtcataga ttatctcata taggactaat cataggaaac   1440
actttgagag caccagtcta ttcttggacg catcgtagtg cagatcgtac gaatacgatt   1500
ggaccaaata gaattactca aattcctgca gtgaagggaa gatttctttt taatggttct   1560
gtaatttcag gaccaggatt tactggtgga gacgtagtta gattgaatag gaataatggt   1620
aatattcaaa atagagggta tattgaagtt ccaattcaat tcacgtcgac atctaccaga   1680
tatcgagttc gagtacgtta tgcttctgta acctcgattg agctcaatgt taatttgggc   1740
aattcatcaa tttttacgaa cacattacca gcaacagctg catcattaga taatctacaa   1800
tcaggggatt ttggttatgt tgaaatcaac aatgctttta catccgcaac aggtaatata   1860
gtaggtgcta gaaattttag tgcaaatgca gaagtaataa tagacagatt tgaatttatc   1920
ccagttactg caaccttcga ggcagaatat gatttagaaa gagcacaaaa g            1971
```

<210> SEQ ID NO 9
<211> LENGTH: 651
<212> TYPE: PRT
<213> ORGANISM: Artificial Sequence
<220> FEATURE:
<223> OTHER INFORMATION: Cry1B variant

<400> SEQUENCE: 9

```
Met Pro Ser Asn Arg Lys Asn Glu Asn Glu Ile Ile Asn Ala Val Ser
1               5                   10                  15

Asn His Ser Ala Gln Met Asp Leu Ser Leu Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Ser Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Met
                85                  90                  95

Glu His Val Glu Gln Ile Val Arg Gln Gln Ile Thr Asp Ser Val Arg
            100                 105                 110

Asp Thr Ala Ile Ala Arg Leu Glu Gly Leu Gly Arg Gly Tyr Arg Ser
```

```
            115                 120                 125
Tyr Gln Gln Ala Leu Glu Thr Trp Leu Asp Asn Arg Asn Asp Ala Arg
            130                 135                 140

Ser Arg Ser Ile Ile Arg Glu Arg Tyr Ile Ala Leu Glu Leu Asp Ile
145                 150                 155                 160

Thr Thr Ala Ile Pro Leu Phe Ser Ile Arg Asn Gln Glu Val Pro Leu
                    165                 170                 175

Leu Met Val Tyr Ala Gln Ala Ala Asn Leu His Leu Leu Leu Leu Arg
                    180                 185                 190

Asp Ala Ser Leu Phe Gly Ser Glu Trp Gly Met Ser Ser Ser Asp Val
                    195                 200                 205

Asn Gln Tyr Tyr Gln Glu Gln Ile Arg Tyr Thr Glu Glu Tyr Ser Asn
                    210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                    245                 250                 255

Leu Gly Val Leu Asp Leu Val Ala Leu Phe Pro Ser Tyr Asp Thr Arg
                    260                 265                 270

Val Tyr Pro Met Asn Thr Ser Ala Gln Leu Thr Arg Glu Ile Tyr Thr
                    275                 280                 285

Asp Pro Ile Gly Arg Thr Asn Ala Pro Ser Gly Phe Ala Ser Thr Asn
290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                    325                 330                 335

Ser Ala Ser Ser Arg Trp Ser Ser Thr Gln His Met Asn Tyr Trp Val
                    340                 345                 350

Gly His Arg Leu Asn Phe Arg Pro Ile Gly Gly Thr Leu Asn Thr Ser
                    355                 360                 365

Thr His Gly Ala Thr Asn Thr Ser Ile Asn Pro Val Thr Leu Gln Phe
                    370                 375                 380

Thr Ser Arg Asp Val Tyr Arg Thr Glu Ser Phe Ala Gly Thr Asn Ile
385                 390                 395                 400

Leu Phe Thr Thr Pro Val Asn Gly Val Pro Trp Ala Arg Phe Asn Phe
                    405                 410                 415

Ile Asn Pro Gln Asn Ile Tyr Glu Arg Gly Ala Thr Thr Tyr Ser Gln
                    420                 425                 430

Pro Tyr Gln Gly Val Gly Ile Gln Leu Phe Asp Ser Glu Thr Glu Leu
                    435                 440                 445

Pro Pro Glu Thr Thr Glu Arg Pro Asn Tyr Glu Ser Tyr Ser His Arg
                    450                 455                 460

Leu Ser His Ile Gly Leu Ile Ile Gly Asn Thr Leu Arg Ala Pro Val
465                 470                 475                 480

Tyr Ser Trp Thr His Arg Ser Ala Asp Arg Thr Asn Thr Ile Gly Pro
                    485                 490                 495

Asn Arg Ile Thr Gln Ile Pro Ala Val Lys Gly Arg Phe Leu Phe Asn
                    500                 505                 510

Gly Ser Val Ile Ser Gly Pro Gly Phe Thr Gly Gly Asp Val Val Arg
                    515                 520                 525

Leu Asn Arg Asn Asn Gly Asn Ile Gln Asn Arg Gly Tyr Ile Glu Val
                    530                 535                 540
```

Pro Ile Gln Phe Thr Ser Thr Ser Thr Arg Tyr Arg Val Arg Val Arg
545                 550                 555                 560

Tyr Ala Ser Val Thr Ser Ile Glu Leu Asn Val Asn Leu Gly Asn Ser
                565                 570                 575

Ser Ile Phe Thr Asn Thr Leu Pro Ala Thr Ala Ser Leu Asp Asn
            580                 585                 590

Leu Gln Ser Gly Asp Phe Gly Tyr Val Glu Ile Asn Asn Ala Phe Thr
            595                 600                 605

Ser Ala Thr Gly Asn Ile Val Gly Ala Arg Asn Phe Ser Ala Asn Ala
        610                 615                 620

Glu Val Ile Ile Asp Arg Phe Glu Phe Ile Pro Val Thr Ala Thr Phe
625                 630                 635                 640

Glu Ala Glu Tyr Asp Leu Glu Arg Ala Gln Lys
                645                 650

<210> SEQ ID NO 10
<211> LENGTH: 1953
<212> TYPE: DNA
<213> ORGANISM: Artificial Sequence
<220> FEATURE:
<223> OTHER INFORMATION: coding sequence of Cry1B variant

<400> SEQUENCE: 10

| | |
|---|---|
| atgccttcaa ataggaaaaa tgagaatgaa attataaatg ctgtatcgaa tcattccgca | 60 |
| caaatggatc tatcgctaga tgctcgtatt gaagatagct tgtgtgtagc cgaggtgaac | 120 |
| aatattgatc catttgttag cgcatcaaca gtccaaacag gtattagtat agctggtaga | 180 |
| atattgggcg tattaggtgt gccgtttgct ggacaactag ctagttttta tagttttctt | 240 |
| gttggggaat tatggcctag cggcagagat ccatgggaaa ttttatgga acatgtcgag | 300 |
| caaattgtaa gacaacaaat aacggacagt gttagggata ccgctattgc tcgtttagaa | 360 |
| ggtctaggaa gagggtatag atcttaccag caggctcttg aaactggtt agataaccga | 420 |
| aatgatgcaa gatcaagaag cattattcgt gagagatata ttgctttaga acttgacatt | 480 |
| actactgcta taccgctttt cagcatacga atcaagagg ttccattatt aatggtatat | 540 |
| gctcaagctg caaatttaca cctattatta ttgagagacg catccctttt tggtagtgaa | 600 |
| tggggggatgt catcttccga tgttaaccaa tattaccaag aacaaatcag atatacagag | 660 |
| gaatattcta accattgcgt acaatggtat aatacagggc taataactt aagagggaca | 720 |
| aatgctgaaa gttggttgcg gtataatcaa ttccgtagag atctaacgtt aggagtatta | 780 |
| gatctagtgg cactattccc aagctatgac acgcgtgttt atccaatgaa taccagtgct | 840 |
| caattaacaa gagaaattta tacagatcca attgggagaa caaatgcacc ttcaggattt | 900 |
| gcaagtacga attggtttaa taataatgca ccatcgtttt ctgccataga ggctgccatt | 960 |
| ttcaggcctc cgcatctact tgattttcca gaacaactta caatttacag tgcatcaagc | 1020 |
| cgttggagta gcactcaaca tatgaattat tgggtgggac ataggcttaa cttccgccca | 1080 |
| ataggaggga cattaaatac ctcaacgcat ggggctacca atacttctat taatcctgta | 1140 |
| acattacagt tcacatctcg agacgtttat aggactgaat catttgcagg acaaatata | 1200 |
| ctatttacta ctcctgtgaa tggagtacct tgggctagat ttaattttat aaaccctcag | 1260 |
| aatatttatg aaagaggcgc cactacctac agtcaaccgt atcagggagt tgggattcaa | 1320 |
| ttatttgatt cagaaactga attaccacca gaaacaacag aacgaccaaa ttatgaatca | 1380 |
| tatagtcata gattatctca tataggacta atcataggaa acactttgag agcaccagtc | 1440 |

```
tattcttgga cgcaccgtag tgcagatcgt acgaatacga ttggaccaaa tagaattact    1500
caaattcctg cagtgaaggg aagatttctt tttaatggtt ctgtaatttc aggaccagga    1560
tttactggtg agacgtagt tagattgaat aggaataatg gtaatattca aaatagaggg    1620
tatattgaag ttccaattca attcacgtcg acatctacca gatatcgagt tcgagtacgt    1680
tatgcttctg taacctcgat tgagctcaat gttaatttgg gcaattcatc aatttttacg    1740
aacacattac cagcaacagc tgcatcatta gataatctac aatcagggga ttttggttat    1800
gttgaaatca acaatgcttt tacatccgca acaggtaata tagtaggtgc tagaaatttt    1860
agtgcaaatg cagaagtaat aatagacaga tttgaattta tcccagttac tgcaaccttc    1920
gaggcagaat atgatttaga aagagcacaa aag                                 1953

<210> SEQ ID NO 11
<211> LENGTH: 655
<212> TYPE: PRT
<213> ORGANISM: Artificial Sequence
<220> FEATURE:
<223> OTHER INFORMATION: Cry1B variant

<400> SEQUENCE: 11

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270
```

Ser Tyr Asp Thr Arg Ile Tyr Pro Ile Asn Thr Ser Ala Gln Leu Thr
              275                 280                 285

Arg Glu Ile Tyr Thr Asp Pro Ile Gly Arg Thr Asn Ala Pro Ser Gly
        290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Thr Gln His
                340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
                435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
                500                 505                 510

Phe Leu Phe Asn Gly Ser Val Ile Ser Gly Pro Gly Phe Thr Gly Gly
                515                 520                 525

Asp Leu Val Arg Leu Asn Asn Ser Gly Asn Asn Ile Gln Asn Arg Gly
530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Ser Ile Val Pro Ala Thr Ala Thr
                580                 585                 590

Ser Leu Asp Asn Leu Gln Ser Arg Asn Phe Gly Tyr Phe Glu Ser Thr
                595                 600                 605

Asn Ala Phe Thr Ser Ala Thr Gly Asn Val Val Gly Val Arg Asn Phe
610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 12
<211> LENGTH: 1965
<212> TYPE: DNA
<213> ORGANISM: Artificial Sequence
<220> FEATURE:

<223> OTHER INFORMATION: coding sequence of Cry1B variant

<400> SEQUENCE: 12

```
atgccgagca atcgtaagaa tgaaaatgaa atcattaacg cactgtccat ccctgcagtg      60
agcaatcaca gcgcgcagat ggatttgagc ctggatgcgc gtatcgagga cagcctgtgt     120
attgccgagg caacaacat caatccgttg gtcagcgcga gcaccgtgca aaccggcatt      180
aacattgccg tcgtatcct gggtgtcctg ggcgttccgt ttgcgggtca gctggcgagc      240
ttttacagct ttatcgttgg tgagttgtgg ccgtcgggtc gtgacccttg ggagattttc     300
atggagcacg tcgagcaact ggtgcgccaa cagattacgg agaatgcgcg caacaccgct     360
ctggcgcgtc tgcaaggtct gggtgcaagc ttccgcgctt accagcagtc cctggaagat     420
tggttggaaa accgtgataa tgcgcgcact cgctccgtcc tgtacacgca gtacatcgcg     480
ctggagctgg acttcttgaa cgcgatgccg ctgtttgcaa tcaacaacca gcaagtgccg     540
ctgctgatgg tctacgccca agccgcgaat ctgcacttgc tgctgctgcg cgacgcatct     600
ctgttcggta gcgaatttgg cctgaccagc caggagatcc agcgctacta tgagcgtcag     660
gccgagaaaa cgcgtgaata ctccgactac tgcgctcgtt ggtacaacac gggtctgaac     720
aatctgcgtg gcaccaacgc ggagtcctgg ctgcgttaca accagtttcg tcgcgatctg     780
accctgggtg ttttggattt ggttgcgctg tttccgagct atgacacccg catctatccg     840
atcaacacca gcgcgcaact gactcgtgaa atctatacgg acccgattgg ccgcactaat     900
gcaccgtccg gtttcgcaag caccaactgg ttcaataaca atgcaccgag cttcagcgcg     960
atcgaggccg cgatctttcg tccgccgcac ctgttggact cccggagca gctgaccatc    1020
tactctgcat ctagccgttg gagcagcacg cagcacatga attactgggt tggccatcgt    1080
ctgaacttcc gcccgattgg tggtacgctg aacactagca cgcacggtgc cactaacacg    1140
agcatcaacc cggtgacgct gcaattcacc agccgtgatg tttaccgtac cgagtcctac    1200
gccggcatca acattctgct gaccaccccg gttaacggcg tcccttgggc tcgtttcaat    1260
tggcgtaacc cactgaatag cctgcgtggt tctttgctgt acaccattgg ttataccggc    1320
gtcggtacgc aactgtttga ctcggaaact gagctgccac cggaaactac cgagcgtccg    1380
aactacgaat cttatagcca ccgtctgtcc aatatccgtc tgatcatcgg caacaccctg    1440
cgtgcgccgg tgtacagctg gacccatcgt agcgccgatc gcacgaacac gattgccacc    1500
aacattatca cccagatccc ggcagtgaaa ggcaactttc tgtttaacgg cagcgtgatc    1560
agcggtccag gttttaccgg cggtgacctg gtgcgcctga caacagcgg caacaatatc    1620
caaaaccgtg gttatatcga agtcccgatt caattcatca gcacgagcac ccgttaccgc    1680
gtccgtgttc gctacgcatc cgttacgccg atccaactga gcgttaactg ggcaattcc    1740
aacattttca gcagcattgt ccctgctacg gcgacctctc tggacaattt gcagagccgt    1800
aacttcggct atttcgaaag caccaacgct ttcaccagcg ctacgggcaa tgtggttggt    1860
gttcgcaatt tcagcgagaa tgcgggcgtc atcattgacc gttttgagtt tatcccggtg    1920
accgcgacct tcgaagcgga gtacgatctg agcgtgcgc aggaa                    1965
```

<210> SEQ ID NO 13
<211> LENGTH: 655
<212> TYPE: PRT
<213> ORGANISM: Artificial Sequence
<220> FEATURE:
<223> OTHER INFORMATION: Cry1B variant

<400> SEQUENCE: 13

-continued

```
Met Pro Ser Asn Arg Lys Asn Glu Asn Gly Ile Ile Asn Ala Leu Ser
 1               5                  10                  15

Ile Pro Ala Val Ser Asn His Ser Ala Gln Met Asp Leu Ser Pro Asp
             20                  25                  30

Ala Arg Ile Glu Asp Ser Leu Cys Val Ala Glu Val Asn Asn Ile Asp
         35                  40                  45

Pro Phe Val Ser Ala Ser Thr Val Gln Thr Gly Ile Asn Ile Ala Gly
     50                  55                  60

Arg Ile Leu Gly Val Leu Gly Val Pro Phe Ala Gly Gln Leu Ala Ser
 65                  70                  75                  80

Phe Tyr Ser Phe Ile Val Gly Glu Leu Trp Pro Ser Gly Arg Asp Pro
                 85                  90                  95

Trp Glu Ile Phe Leu Glu His Val Glu Gln Leu Val Arg Gln Gln Ile
             100                 105                 110

Thr Glu Asn Ala Arg Asn Thr Ala Leu Ala Arg Leu Gln Gly Leu Gly
         115                 120                 125

Ala Ser Phe Arg Ala Tyr Gln Gln Ser Leu Glu Asp Trp Leu Glu Asn
     130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                 165                 170                 175

Gln Arg Val Pro Leu Leu Met Val Tyr Ala Gln Ala Ala Asn Leu His
             180                 185                 190

Leu Leu Leu Leu Arg Asp Ala Ser Leu Phe Gly Ser Glu Phe Gly Leu
         195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                 245                 250                 255

Arg Arg Asp Leu Thr Leu Gly Val Leu Asp Leu Val Ala Leu Phe Pro
             260                 265                 270

Ser Tyr Asp Thr Arg Val Tyr Pro Ile Asn Thr Ser Ala Gln Leu Thr
         275                 280                 285

Arg Glu Ile Tyr Thr Asp Pro Ile Gly Arg Thr Asn Ala Pro Ser Gly
     290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                 325                 330                 335

Gln Leu Thr Ile Phe Ser Val Leu Ser Arg Trp Ser Ser Thr Gln His
             340                 345                 350

Met Asn Tyr Trp Val Gly His Arg Leu Glu Ser Arg Thr Ile Arg Gly
         355                 360                 365

Ser Leu Ser Thr Ser Thr His Gly Asn Thr Asn Thr Ser Ile Asn Pro
     370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                 405                 410                 415
```

-continued

```
Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser His Ile Gly Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Thr Gly Pro Asn Arg Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Leu Glu Val Pro Ile Gln Phe Ile Ser Thr Ser Thr Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asp Phe Gly Tyr Phe Glu Ser Thr
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 14
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 14

```
atgccgagca atcgtaagaa tgaaaatgga atcattaacg cgctgtccat ccctgcagtg      60
agcaatcaca gcgcgcagat ggatttgagc ccggatgcgc gtatcgagga cagcctgtgt     120
gtcgccgagg taaacaatat tgatccgttc gtcagcgcga gcaccgtgca aaccggcatt     180
aacattgccg gtcgtatcct gggtgtcctg ggcgttccgt ttgcgggtca gctggcgagc     240
ttttacagct ttatcgttgg tgagttgtgg ccgtcgggtc gtgacccttg ggagattttc     300
ttggagcacg tcgagcaact ggtgcgccaa cagattacgg agaatgcgcg caacaccgct     360
ctggcgcgtc tgcaaggtct gggtgcaagc ttccgcgctt accagcagtc cctggaagat     420
tggttggaaa accgtgatga tgcgcgcact cgctccgtcc tgtacacgca gtacatcgcg     480
ctggagctgg acttcttgaa cgcgatgccg ctgtttgcaa tcaacaacca gcgagtgccg     540
ctgctgatgg tctacgccca agccgcgaat ctgcacttgc tgctgctgcg cgacgcatct     600
ctgttcggta gcgaatttgg cctgaccagc caggagatcc agcgctacta tgagcgtcag     660
gccgagaaaa cgcgtgaata ctccgactac tgcgctcgtt ggtacaacac gggtctgaac     720
```

```
aatctgcgtg gcaccaacgc ggagtcctgg ctgcgttata accagtttcg tcgcgatctg    780
accctgggtg tattggattt ggttgcgctg tttccgagct atgacacccg cgtgtatccg    840
atcaacacca gcgcgcaact gactcgtgaa atctatacgg acccgattgg ccgcactaat    900
gcaccgtccg gtttcgcaag caccaactgg ttcaataaca atgcaccgag cttcagcgcg    960
atcgaggcgg ctgtcatccg tccgccgcac ctgttggact cccggagca gctgaccatc    1020
ttttctgtgt tgtctcgttg gagcagcacg cagcacatga attactgggt tggccatcgt    1080
ctggaaagcc gcaccattcg cggtagcctg agcactagca cgcacggtaa tactaacacg    1140
agcatcaacc cggtgacgct gcaattcacc agccgtgatg tttaccgtac cgagtcctac    1200
gccggcatca acattctgct gaccaccccg gttaacggcg tcccttgggc tcgtttcaat    1260
tggcgtaacc cactgaatag cctgcgtggt tctttgctgt acaccattgg ttataccggc    1320
gtcggtacgc aactgtttga ctcggaaact gagctgccac cggaaactac cgagcgtccg    1380
aactacgaat cttatagcca ccgtctgtcc catattggtc tgatcatcgg caacaccctg    1440
cgtgcaccgg tgtacagctg gacccatcgt agcgccgatc gcacgaacac gactggtccg    1500
aaccgtatca cccagatccc ggcagtgaaa ggcaactttc tgtttaacgg cagcgtgatc    1560
agcggtccag gttttaccgg cggtgacctg gtgcgcctga acaacagcgg caacaatatc    1620
caaaaccgtg gttatctgga agtcccgatt caattcatca gcacgagcac ccgttaccgc    1680
gtccgtgttc gctacgcatc cgttacgccg atccaactga cgttaactg gggcaattcc    1740
aacattttca gcagcattgt ccctgctacg gcgacctctc tggacaattt gcagagccgt    1800
gacttcggct atttcgaaag caccaacgct ttcaccagcg ctacgggcaa tgtggttggt    1860
gttcgcaatt tcagcgagaa tgcgggcgtc atcattgacc gttttgagtt tatcccggtg    1920
accgcgacct tcgaagcgga gtacgatctg gagcgtgcgc aggaa                    1965
```

<210> SEQ ID NO 15
<211> LENGTH: 650
<212> TYPE: PRT
<213> ORGANISM: Artificial Sequence
<220> FEATURE:
<223> OTHER INFORMATION: Cry1B variant

<400> SEQUENCE: 15

```
Met Pro Ser Asn Arg Lys Asn Glu Asn Glu Ile Ile Asn Ala Val Ser
1               5                   10                  15

Asn His Ser Ala Gln Met Asp Leu Ser Pro Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Met
                85                  90                  95

Glu His Val Glu Gln Ile Val Arg Gln Gln Ile Thr Glu Asn Ala Arg
            100                 105                 110

Asn Thr Ala Leu Ala Arg Leu Gln Gly Leu Gly Ala Ser Phe Arg Ala
        115                 120                 125

Tyr Gln Gln Ser Leu Glu Asp Trp Leu Glu Asn Arg Asp Asp Ala Arg
    130                 135                 140
```

-continued

Thr Arg Ser Val Leu Tyr Thr Gln Tyr Ile Ala Leu Glu Leu Asp Phe
145                 150                 155                 160

Leu Asn Ala Met Pro Leu Phe Ala Ile Asn Asn Gln Gln Val Pro Leu
            165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
            195                 200                 205

Gln Arg Tyr Tyr Glu Arg Gln Ala Glu Lys Thr Arg Glu Tyr Ser Asp
    210                 215                 220

Tyr Cys Ala Arg Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Ile Tyr Pro Ile Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
290                 295                 300

Trp Phe Asn Asn Asn Ala Pro Ser Phe Ser Ala Ile Glu Ala Ala Val
305                 310                 315                 320

Ile Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
        355                 360                 365

Thr His Gly Ala Thr Asn Thr Ser Ile Asn Pro Val Thr Leu Gln Phe
    370                 375                 380

Thr Ser Arg Asp Val Tyr Arg Thr Glu Ser Tyr Ala Gly Ile Asn Ile
385                 390                 395                 400

Leu Leu Thr Thr Pro Val Asn Gly Val Pro Trp Ala Arg Phe Asn Trp
                405                 410                 415

Arg Asn Pro Leu Asn Ser Leu Arg Gly Ser Leu Leu Tyr Thr Ile Gly
            420                 425                 430

Tyr Thr Gly Val Gly Ile Gln Leu Phe Asp Ser Glu Thr Glu Leu Pro
        435                 440                 445

Pro Glu Thr Thr Glu Arg Pro Asn Tyr Glu Ser Tyr Ser His Arg Leu
    450                 455                 460

Ser Asn Ile Arg Leu Ile Ser Gly Asn Thr Leu Arg Ala Pro Val Tyr
465                 470                 475                 480

Ser Trp Thr His Arg Ser Ala Asp Arg Thr Asn Thr Ile Ala Thr Asn
                485                 490                 495

Ile Ile Thr Gln Ile Pro Ala Val Lys Gly Asn Phe Leu Phe Asn Gly
            500                 505                 510

Ser Val Thr Ser Gly Pro Gly Phe Thr Gly Gly Asp Leu Val Arg Leu
        515                 520                 525

Asn Asn Ser Gly Asn Asn Ile Gln Asn Arg Gly Tyr Leu Glu Val Pro
    530                 535                 540

Ile Gln Phe Ile Ser Thr Ser Thr Arg Tyr Arg Val Arg Val Arg Tyr
545                 550                 555                 560

Ala Ser Val Thr Pro Ile Gln Leu Ser Val Asn Trp Gly Asn Ser Asn

-continued

```
                565                 570                 575

Ile Phe Ser Ser Ile Val Pro Ala Thr Ala Thr Ser Leu Asp Asn Leu
            580                 585                 590

Gln Ser Arg Asp Phe Gly Tyr Phe Glu Ser Thr Asn Ala Phe Thr Ser
        595                 600                 605

Ala Thr Gly Asn Val Val Gly Val Arg Asn Phe Ser Glu Asn Ala Gly
    610                 615                 620

Val Ile Ile Asp Arg Phe Glu Phe Ile Pro Val Thr Ala Thr Phe Glu
625                 630                 635                 640

Ala Glu Tyr Asp Leu Glu Arg Ala Gln Glu
                645                 650

<210> SEQ ID NO 16
<211> LENGTH: 1950
<212> TYPE: DNA
<213> ORGANISM: Artificial Sequence
<220> FEATURE:
<223> OTHER INFORMATION: coding sequence of Cry1B variant

<400> SEQUENCE: 16
atgccgagca atcgtaagaa tgaaaatgaa atcattaacg cagtgagcaa tcacagcgcg      60
cagatggatt tgagcccgga tgcgcgtatc gaggacagcc tgtgtgtcgc cgaggtaaac     120
aatattgatc cgttcgtcag cgcgagcacc gtgcaaaccg gcattaacat tgccggtcgt     180
atcctgggtg tcctgggcgt tccgtttgcg ggtcagctgg cgagctttta cagctttttg     240
gttggtgagt tgtggccgtc gggtcgtgac ccttgggaga ttttcatgga gcacgtcgag     300
caaattgtgc gccaacagat tacggagaat gcgcgcaaca ccgctctggc gcgtctgcaa     360
ggtctgggtg caagcttccg cgcttaccag cagtccctgg aagattggtt ggaaaaccgt     420
gatgatgcgc gcactcgctc cgtcctgtac acgcagtaca tcgcgctgga gctggacttc     480
ttgaacgcga tgccgctgtt tgcaatcaac aaccagcaag tgccgctgct gatggtctac     540
gcccaagccg cgaatctgca cttgctgctg ctgcgcgacg catctctgtt cggtagcgaa     600
tttggcctga ccagccagga gatccagcgc tactatgagc gtcaggccga gaaaacgcgt     660
gaatactccg actactgcgc tcgttggtac aacacgggtc tgaacaatct gcgtggcacc     720
aacgcggagt cctggctgcg ttacaaccag tttcgtcgcg atctgaccct gggtgttttg     780
gatttggttg cgctgtttcc gagctatgac acccgcatct atccgatcaa caccagcgcg     840
caactgactc gtgaaatcta tacggacccg attggccgca ctaatgcacc gtccggtttc     900
gcaagcacca actggttcaa taacaatgca ccgagcttca gcgcgatcga ggcggctgtc     960
atccgtccgc cgcacctgtt ggacttcccg gagcagctga ccatctactc tgcatctagc    1020
cgttggagca gcacgcagca catgaattac tgggttggcc atcgtctgaa cttccgcccg    1080
attggtggta cgctgaacac tagcacgcac ggtgccacta acacgagcat caacccggtg    1140
acgctgcaat tcaccagccg tgatgtttac cgtaccgagt cctacgccgg gatcaacatt    1200
ctgctgacca ccccggttaa cggcgtccct tgggctcgtt tcaattggcg taacccactg    1260
aatagcctgc gtggttcttt gctgtacacc attggttata ccggcgtcgg tattcaactg    1320
tttgactcgg aaactgagct gccaccggaa actaccgagc gtccgaacta cgaatcttat    1380
agccaccgtc tgtccaatat ccgtctgatc agcggcaaca ccctgcgtgc gccggtgtac    1440
agctggaccc accgtagcgc cgatcgcacg aacacgattg ccaccaacat tatcacccag    1500
atcccggcag tgaaaggcaa ctttctgttt aacggcagcg tgaccagcgg tccaggtttt    1560
```

```
accggcggtg acctggtgcg cctgaacaac agcggcaaca atatccaaaa ccgtggttat    1620
ctggaagtcc cgattcaatt catcagcacg agcacccgtt accgcgtccg tgttcgctac    1680
gcatccgtta cgccgatcca actgagcgtt aactggggca attccaacat tttcagcagc    1740
attgtccctg ctacggcgac ctctctggac aatttgcaga gccgtgactt cggctatttc    1800
gaaagcacca acgctttcac cagcgctacg ggcaatgtgg ttggtgttcg caatttcagc    1860
gagaatgcgg gcgtcatcat tgaccgtttt gagtttatcc cggtgaccgc gaccttcgaa    1920
gcggagtacg atctggagcg tgcgcaggaa                                     1950

<210> SEQ ID NO 17
<211> LENGTH: 655
<212> TYPE: PRT
<213> ORGANISM: Artificial Sequence
<220> FEATURE:
<223> OTHER INFORMATION: Cry1B variant

<400> SEQUENCE: 17
```

Met Pro Ser Asn Arg Lys Asn Glu Asn Glu Ile Ile Asn Ala Leu Ser
1               5                   10                  15

Ile Pro Ala Val

```
                290             295             300
Phe Ala Ser Thr Asn Trp Phe Asn Asn Asn Ala Pro Ser Phe Ser Ala
305             310             315             320
Ile Glu Ala Ala Ile Phe Arg Pro Pro His Leu Leu Asp Phe Pro Glu
                325             330             335
Gln Leu Thr Ile Tyr Ser Ala Ser Arg Trp Ser Ser Thr Gln His
                340             345             350
Met Asn Tyr Trp Val Gly His Arg Leu Asn Phe Arg Pro Ile Gly Gly
        355             360             365
Thr Leu Asn Thr Ser Thr His Gly Ala Thr Asn Thr Ser Ile Asn Pro
370             375             380
Val Thr Leu Gln Phe Thr Ser Arg Asp Val Tyr Arg Thr Glu Ser Tyr
385             390             395             400
Ala Gly Ile Asn Ile Leu Leu Thr Thr Pro Val Asn Gly Val Pro Trp
                405             410             415
Ala Arg Phe Asn Trp Arg Asn Pro Leu Asn Ser Leu Arg Gly Ser Leu
                420             425             430
Leu Tyr Thr Ile Gly Tyr Thr Gly Val Gly Thr Gln Leu Phe Asp Ser
            435             440             445
Glu Thr Glu Leu Pro Pro Glu Thr Thr Glu Arg Pro Asn Tyr Glu Ser
450             455             460
Tyr Ser His Arg Leu Ser Asn Ile Arg Leu Ile Ile Gly Asn Thr Leu
465             470             475             480
Arg Ala Pro Val Tyr Ser Trp Thr His Arg Ser Ala Asp Arg Thr Asn
                485             490             495
Thr Ile Ala Thr Asn Ile Ile Thr Gln Ile Pro Ala Val Lys Gly Asn
                500             505             510
Phe Leu Phe Asn Gly Ser Val Ile Ser Gly Pro Gly Phe Thr Gly Gly
            515             520             525
Asp Leu Val Arg Leu Asn Asn Ser Gly Asn Asn Ile Gln Asn Arg Gly
530             535             540
Tyr Ile Glu Val Pro Ile Gln Phe Ile Ser Thr Ser Thr Arg Tyr Arg
545             550             555             560
Val Arg Val Arg Tyr Ala Ser Val Thr Pro Ile Gln Leu Ser Val Asn
                565             570             575
Trp Gly Asn Ser Asn Ile Phe Ser Arg Ile Val Pro Ala Thr Ala Tyr
            580             585             590
Ser Leu Asp Asn Leu Gln Ser Arg Asn Phe Gly Tyr Phe Glu Ser Thr
            595             600             605
Asn Ala Phe Thr Ser Ala Thr Gly Asn Val Val Gly Val Arg Asn Phe
610             615             620
Ser Glu Asn Ala Gly Val Ile Ile Asp Arg Phe Glu Phe Ile Pro Val
625             630             635             640
Thr Ala Thr Phe Glu Ala Glu Tyr Asp Leu Glu Arg Ala Gln Glu
                645             650             655

<210> SEQ ID NO 18
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 18
atgccgagca atcgtaagaa tgaaaatgaa atcattaacg cactgtccat ccctgcagtg    60
```

```
agcaatcaca gcgcgcagat ggatttgagc ctggatgcgc gtatcgagga cagcctgtgt    120
attgccgagg gcaacaacat caatccgttg gtcagcgcga gcaccgtgca aaccggcatt    180
aacattgccg tcgtatcct gggtgtcctg ggcgttccgt ttgcgggtca gctggcgagc    240
ttttacagct ttatcgttgg tgagttgtgg ccgtcgggtc gtgacccttg ggagattttc    300
atggagcacg tcgagcaact ggtgcgccaa cagattacgg agaatgcgcg caacaccgct    360
ctggcgcgtc tgcaaggtct gggtgcaagc ttccgcgctt accagcagtc cctggaagat    420
tggttggaaa accgtgataa tgcgcgcact cgctccgtcc tgtacacgca gtacatcgcg    480
ctggagctgg acttcttgaa cgcgatgccg ctgtttgcaa tcaacaacca gcaagtgccg    540
ctgctgatgg tctacgccca agccgcgaat ctgcacttgc tgctgctgcg cgacgcatct    600
ctgttcggta gcgaatttgg cctgaccagc caggagatcc agcgctacta tgagcgtcag    660
gccgagaaaa cgcgtgaata ctccgactac tgcgctcgtt ggtacaacac gggtctgaac    720
aatctgcgtg gcaccaacgc ggagtcctgg ctgcgttaca accagtttcg tcgcgatctg    780
accctgggtg tttttggattt ggttgcgctg tttccgagct atgacacccg catctatccg    840
atcaacacca gcgcgcaact gactcgtgaa atctatacgg acccgattgg ccgcactaat    900
gcaccgtccg gtttcgcaag caccaactgg ttcaataaca atgcaccgag cttcagcgcg    960
atcgaggccc gatctttcg tccgccgcac ctgttggact cccggagca gctgaccatc   1020
tactctgcat ctagccgttg gagcagcacg cagcacatga attactgggt tggccatcgt   1080
ctgaacttcc gcccgattgg tggtacgctg aacactagca cgcacggtgc cactaacacg   1140
agcatcaacc cggtgacgct gcaattcacc agccgtgatg tttaccgtac cgagtcctac   1200
gccggcatca acattctgct gaccaccccg gttaacggcg tcccttgggc tcgtttcaat   1260
tggcgtaacc cactgaatag cctgcgtggt tctttgctgt acaccattgg ttataccggc   1320
gtcggtacgc aactgtttga ctcggaaact gagctgccac cggaaactac cgagcgtccg   1380
aactacgaat cttatagcca ccgtctgtcc aatatccgtc tgatcatcgg caacaccctg   1440
cgtgcgccgg tgtacagctg gacccatcgt agcgccgatc gcacgaacac gattgccacc   1500
aacattatca cccagatccc ggcagtgaaa ggcaactttc tgtttaacgg cagcgtgatc   1560
agcggtccag gttttaccgg cggtgacctg gtgcgcctga caacagcgg caacaatatc   1620
caaaaccgtg ttatatcga agtcccgatt caattcatca gcacgagcac ccgttaccgc   1680
gtccgtgttc gctacgcatc cgttacgccg atccaactga gcgttaactg gggcaattcc   1740
aacattttca gccgcattgt ccctgctacg gcgtactctc tggacaattt gcagagccgt   1800
aacttcggct atttcgaaag caccaacgct ttcaccagcg ctacgggcaa tgtggttggt   1860
gttcgcaatt tcagcgagaa tgcgggcgtc atcattgacc gttttgagtt tatcccggtg   1920
accgcgacct tcgaagcgga gtacgatctg gagcgtgcgc aggaa              1965
```

<210> SEQ ID NO 19
<211> LENGTH: 655
<212> TYPE: PRT
<213> ORGANISM: Artificial Sequence
<220> FEATURE:
<223> OTHER INFORMATION: Cry1B variant

<400> SEQUENCE: 19

Met Pro Ser Asn Arg Lys Asn Glu Asn Glu Ile Ile Asn Ala Leu Ser
1 5 10 15

Ile Pro Ala Val Ser Asn His Ser Ala Gln Met Asp Leu Ser Leu Asp

```
            20                  25                  30
Ala Arg Ile Glu Asp Ser Leu Cys Ile Ala Glu Gly Asn Asn Ile Asn
            35                  40                  45

Pro Leu Val Ser Ala Ser Thr Val Gln Thr Gly Ile Asn Ile Ala Gly
        50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Gln Leu Val Arg Gln Gln Ile
                100                 105                 110

Thr Glu Asn Ala Arg Asn Thr Ala Leu Ala Arg Leu Gln Gly Leu Gly
                115                 120                 125

Ala Ser Phe Arg Ala Tyr Gln Gln Ser Leu Glu Asp Trp Leu Glu Asn
        130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Ile Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
        290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
                340                 345                 350

Met Asn Tyr Trp Val Gly His Arg Leu Asn Phe Arg Pro Ile Gly Gly
            355                 360                 365

Thr Leu Asn Thr Ser Thr His Gly Ala Thr Asn Thr Ser Ile Asn Pro
        370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445
```

-continued

```
                Glu Thr Glu Leu Pro Pro Glu Thr Thr Glu Arg Pro Asn Tyr Glu Ser
                    450                 455                 460

Tyr Ser His Arg Leu Ser Asn Ile Arg Leu Ile Ile Gly Asn Thr Leu
                465                 470                 475                 480

Arg Ala Pro Val Tyr Ser Trp Thr His Arg Ser Ala Asp Arg Thr Asn
                                485                 490                 495

Thr Ile Ala Thr Asn Ile Ile Thr Gln Ile Pro Ala Val Lys Gly Asn
                                500                 505                 510

Phe Leu Phe Asn Gly Ser Val Ile Ser Gly Pro Gly Phe Thr Gly Gly
                            515                 520                 525

Asp Leu Val Arg Leu Asn Asn Ser Gly Asn Asn Ile Gln Asn Arg Gly
                    530                 535                 540

Tyr Ile Glu Val Pro Ile Gln Phe Ile Ser Thr Ser Thr Arg Tyr Arg
                545                 550                 555                 560

Val Arg Val Arg Tyr Ala Ser Val Thr Pro Ile Arg Leu Ser Val Asn
                                565                 570                 575

Trp Gly Asn Ser Asn Ile Phe Ser Ser Ile Val Pro Ala Thr Ala Thr
                                580                 585                 590

Ser Leu Asp Asn Leu Gln Ser Arg Asn Phe Gly Tyr Phe Glu Ser Arg
                            595                 600                 605

Asn Ala Phe Thr Ser Ala Thr Gly Asn Val Val Gly Val Arg Asn Phe
                    610                 615                 620

Ser Glu Asn Ala Gly Val Ile Ile Asp Arg Phe Glu Phe Ile Pro Val
                625                 630                 635                 640

Thr Ala Thr Phe Glu Ala Glu Tyr Asp Leu Glu Arg Ala Gln Glu
                                645                 650                 655

<210> SEQ ID NO 20
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 20
atgccgagca atcgtaagaa tgaaaatgaa atcattaacg cactgtccat ccctgcagtg     60
agcaatcaca gcgcgcagat ggatttgagc ctggatgcgc gtatcgagga cagcctgtgt    120
attgccgagg caacaacat caatccgttg gtcagcgcga gcaccgtgca aaccggcatt    180
aacattgccg tcgtatcct gggtgtcctg ggcgttccgt ttgcgggtca gctggcgagc    240
ttttacagct ttatcgttgg tgagttgtgg ccgtcgggtc gtgacccttg ggagattttc    300
atggagcacg tcgagcaact ggtgcgccaa cagattacgg agaatgcgcg caacaccgct    360
ctggcgcgtc tgcaaggtct gggtgcaagc ttccgcgctt accagcagtc cctggaagat    420
tggttggaaa accgtgataa tgcgcgcact cgctccgtcc tgtacacgca gtacatcgcg    480
ctggagctgg acttcttgaa cgcgatgccg ctgtttgcaa tcaacaacca gcaagtgccg    540
ctgctgatgg tctacgccca agccgcgaat ctgcacttgc tgctgctgcg cgacgcatct    600
ctgttcggta gcgaatttgg cctgaccagc caggagatcc agcgctacta tgagcgtcag    660
gccgagaaaa cgcgtgaata ctccgactac tgcgctcgtt ggtacaacac gggtctgaac    720
aatctgcgtg gcaccaacgc ggagtcctgg ctgcgttaca accagtttcg tcgcgatctg    780
accctgggtg ttttggattt ggttgcgctg tttccgagct atgacacccg catctatccg    840
atcaacacca gcgcgcaact gactcgtgaa atctatacgg acccgattgg ccgcactaat    900
```

```
gcaccgtccg gtttcgcaag caccaactgg ttcaataaca atgcaccgag cttcagcgcg    960
atcgaggccg cgatctttcg tccgccgcac ctgttggact tcccggagca gctgaccatc   1020
tactctgcat ctagccgttg gagcagcacg cagcacatga attactgggt tggccatcgt   1080
ctgaacttcc gcccgattgg tggtacgctg aacactagca cgcacggtgc cactaacacg   1140
agcatcaacc cggtgacgct gcaattcacc agccgtgatg tttaccgtac cgagtcctac   1200
gccggcatca acattctgct gaccaccccg gttaacggcg tcccttgggc tcgtttcaat   1260
tggcgtaacc cactgaatag cctgcgtggt tctttgctgt acaccattgg ttataccggc   1320
gtcggtacgc aactgtttga ctcggaaact gagctgccac cggaaactac cgagcgtccg   1380
aactacgaat cttatagcca ccgtctgtcc aatatccgtc tgatcatcgg caacaccctg   1440
cgtgcgccgg tgtacagctg gacccatcgt agcgccgatc gcacgaacac gattgccacc   1500
aacattatca cccagatccc ggcagtgaaa ggcaactttc tgtttaacgg cagcgtgatc   1560
agcggtccag gttttaccgg cggtgacctg gtgcgcctga caacagcgg caacaatatc   1620
caaaaccgtg gttatatcga agtcccgatt caattcatca gcacgagcac ccgttaccgc   1680
gtccgtgttc gctacgcatc cgttacgccg atccgcctga gcgttaactg gggcaattcc   1740
aacattttca gcagcattgt ccctgctacg gcgacctctc tggacaattt gcagagccgt   1800
aacttcggct atttcgaaag ccgcaacgct ttcaccagcg ctacgggcaa tgtggttggt   1860
gttcgcaatt tcagcgagaa tgcgggcgtc atcattgacc gttttgagtt tatcccggtg   1920
accgcgacct tcgaagcgga gtacgatctg gagcgtgcgc aggaa                  1965

<210> SEQ ID NO 21
<211> LENGTH: 655
<212> TYPE: PRT
<213> ORGANISM: Artificial Sequence
<220> FEATURE:
<223> OTHER INFORMATION: Cry1B variant

<400> SEQUENCE: 21

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175
```

```
Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590
```

```
Ser Leu Asp Asn Leu Gln Ser Arg Asn Phe Gly Tyr Phe Glu Ser Arg
            595                 600                 605

Asn Ala Phe Thr Ser Ala Thr Gly Asn Val Val Gly Val Arg Asn Phe
        610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
            645                 650                 655

<210> SEQ ID NO 22
<211> LENGTH: 1965
<212> TYPE: DNA
<213> ORGANISM: Artificial Sequence
<220> FEATURE:
<223> OTHER INFORMATION: coding sequence of Cry1B variant

<400

```
aacattttca gcagcattgt ccctgctacg gcgacctctc tggacaattt gcagagccgt    1800
aacttcggct atttcgaaag ccgcaacgct ttcaccagcg ctacgggcaa tgtggttggt    1860
gttcgcaatt tcagcgagaa tgcgggcgtc atcattgacc gttttgagtt tatcccggtg    1920
accgcgacct tcgaagcgga gtacgatctg gagcgtgcgc aggaa                   1965
```

<210> SEQ ID NO 23
<211> LENGTH: 655
<212> TYPE: PRT
<213> ORGANISM: Artificial Sequence
<220> FEATURE:
<223> OTHER INFORMATION: Cry1B variant

<400> SEQUENCE: 23

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn

```
Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Ser Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 24
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 24
atgccgagca atcgtaagaa tgaaaatgaa atcattaacg cactgtccat ccctgcagtg      60
agcaatcaca gcgcgcagat ggatttgagc ctggatgcgc gtatcgagga cagcctgtgt     120
attgccgagg caacaacat caatccgttg gtcagcgcga gcaccgtgca aaccggcatt      180
```

```
aacattgccg gtcgtatcct gggtgtcctg ggcgttccgt ttgcgggtca gctggcgagc    240
ttttacagct ttatcgttgg tgagttgtgg ccgtcgggtc gtgacccttg ggagattttc    300
atggagcacg tcgagcaact ggtgcgccaa gcgattacgc tgaatgcgcg caacaccgct    360
ctggcgcgtc tgcaaggtct gggtgcaagc ttccgcgctt accagcagtc cctggaagat    420
tggttggaaa accgtgataa tgcgcgcact cgctccgtcc tgtacacgca gtacatcgcg    480
ctggagctgg acttcttgaa cgcgatgccg ctgtttgcaa tcaacaacca gcaagtgccg    540
ctgctgatgg tctacgccca agccgcgaat ctgcacttgc tgctgctgcg cgacgcatct    600
ctgttcggta gcgaatttgg cctgaccagc caggagatcc agcgctacta tgagcgtcag    660
gccgagaaaa cgcgtgaata ctccgactac tgcgctcgtt ggtacaacac gggtctgaac    720
aatctgcgtg gcaccaacgc ggagtcctgg ctgcgttaca accagtttcg tcgcgatctg    780
accctgggtg ttttggattt ggttgcgctg tttccgagct atgacacccg catctatccg    840
atcaacacca gcgcgcaact gactcgtgaa atctataccgg accgattgg ccgcactaat    900 gcaccgtccg gtttcgcaag caccaactgg ttcaataaca atgcaccgag cttcagcgcg    960
atcgaggccg cgatctttcg tccgccgcac ctgttggact cccggagca gctgaccatc   1020 tactctgcat ctagccgttg gagcagcacg cagcacatga attactgggt tggccatcgt   1080
ctgaacttcc gcccgattgg tggtacgctg aacactagca cgcacggtgc cactaacacg   1140
agcatcaacc cggtgacgct gcaattcacc agccgtgatg tttaccgtac cgagtcctac   1200
gccggcatca acattctgct gaccaccccg gttaacggcg tcccttgggc tcgtttcaat   1260
tggcgtaacc cactgaatag cctgcgtggt tctttgctgt acaccattgg ttataccggc   1320
gtcggtacgc aactgtttga ctcggaaact gagctgccac cggaaactac cgagcgtccg   1380
aactacgaat cttatagcca ccgtctgtcc aatatccgtc tgatcatcag cggcaccctg   1440
cgtgcgccgg tgtacagctg gacccatcgt agcgccgatc gcacgaacac gattgccacc   1500
aacattatca cccagatccc ggcagtgaaa ggcaactttc tgtttaacgg cagcgtgatc   1560
agcggtccag gttttaccgg cggtgacctg gtgcgcctga caacagcgg caacaatatc   1620 caaaaccgtg gttatatcga agtcccgatt caattcatca gcacgagcac ccgttaccgc   1680
gtccgtgttc gctacgcatc cgttacgccg atccgcctga gcgttaactg ggcaattcc    1740 aacatttttca gcagcattgt ccctgctacg gcgacctctc tggacaattt gcagagccgt   1800
aacttcggct atttcgaaag ccgcaacgct ttcaccagcg ctacgggcaa tgtggttggt   1860
gttcgcaatt tcagcgagaa tgcgggcgtc atcattgacc gtttgagtt tatcccggtg    1920 accgcgacct tcgaagcgga gtacgatctg gagcgtgcgc aggaa                   1965
```

<210> SEQ ID NO 25
<211> LENGTH: 655
<212> TYPE: PRT
<213> ORGANISM: Artificial Sequence
<220> FEATURE:
<223> OTHER INFORMATION: Cry1B variant

<400> SEQUENCE: 25

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45
```

```
Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Ala Ile
                100                 105                 110

Thr Leu Asn Ala Arg Asn Thr Ala Leu Ala Arg Leu Gln Gly Leu Gly
            115                 120                 125

Ala Ser Phe Arg Ala Tyr Gln Gln Ser Leu Glu Asp Trp Leu Glu Asn
130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Ile Tyr Pro Ile Asn Thr Ser Ala Gln Leu Thr
    275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Arg Trp Ser Ser Thr Gln His
            340                 345                 350

Met Asn Tyr Trp Val Gly His Arg Leu Tyr Phe Arg Pro Ile Asn Gly
            355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ile Gly Asn Thr Leu
```

-continued

```
465                 470                 475                 480

Arg Ala Pro Val Tyr Ser Trp Thr His Arg Ser Ala Asp Arg Thr Asn
                485                 490                 495
Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560
Val Arg Val Arg Tyr Ala Ser Val Thr Pro Ile Arg Leu Ser Val Asn
                565                 570                 575
Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640
Thr Ala Thr Phe Glu Ala Glu Tyr Asp Leu Glu Arg Ala Gln Glu
                645                 650                 655

<210> SEQ ID NO 26
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 26
atgccgagca atcgtaagaa tgaaaatgaa atcattaacg cactgtccat ccctgcagtg     60
agcaatcaca gcgcgcagat ggatttgagc ctggatgcgc gtatcgagga cagcctgtgt    120
attgccgagg gcaacaacat caatccgttg gtcagcgcga gcaccgtgca aaccggcatt    180
aacattgccg gtcgtatcct gggtgtcctg ggcgttccgt ttgcgggtca gctggcgagc    240
ttttacagct ttatcgttgg tgagttgtgg ccgtcgggtc gtgacccttg ggagattttc    300
atggagcacg tcgagcaact ggtgcgccaa gcgattacgc tgaatgcgcg caacaccgct    360
ctggcgcgtc tgcaaggtct gggtgcaagc ttccgcgctt accagcagtc cctggaagat    420
tggttggaaa accgtgataa tgcgcgcact cgctccgtcc tgtacacgca gtacatcgcg    480
ctggagctgg acttcttgaa cgcgatgccg ctgtttgcaa tcaacaacca gcaagtgccg    540
ctgctgatgg tctacgccca agccgcgaat ctgcacttgc tgctgctgcg cgacgcatct    600
ctgttcggta gcgaatttgg cctgaccagc caggagatcc agcgctacta tgagcgtcag    660
gccgagaaaa cgcgtgaata ctccgactac tgcgctcgtt ggtacaacac gggtctgaac    720
aatctgcgtg gcaccaacgc ggagtcctgg ctgcgttaca accagtttcg tcgcgatctg    780
accctgggtg ttttggattt ggttgcgctg tttccgagct atgacacccg catctatccg    840
atcaacacca gcgcgcaact gactcgtgaa atctatacgg acccgattgg ccgcactaat    900
gcaccgtccg gtttcgcaag caccaactgg ttcaataaca atgcaccgag cttcagcgcg    960
atcgaggccg cgatctttcg tccgccgcac ctgttggact tcccggagca gctgaccatc   1020
```

-continued

```
tactctgcat ctagccgttg gagcagcacg cagcacatga attactgggt tggccatcgt    1080
ctgtatttcc gcccgattaa cggtacgctg aacactagca cgcacggtgc cactaacacg    1140
agcatcaacc cggtgacgct gcaattcacc agccgtgatg tttaccgtac cgagtcctac    1200
gccggcatca acattctgct gaccacccg gttaacggcg tcccttgggc tcgtttcaat    1260
tggcgtaacc cactgaatag cctgcgtggt tctttgctgt acaccattgg ttataccggc    1320
gtcggtacgc aactgtttga ctcggaaact gagctgccac cggaaactac cgagcgtccg    1380
aactacgaat cttatagcca ccgtctgtcc aatatccgtc tgatcatcgg caacaccctg    1440
cgtgcgccgg tgtacagctg gacccatcgt agcgccgatc gcacgaacac gattgccacc    1500
aacattatca cccagatccc ggcagtgaaa ggcaactttc tgtttaacgg cagcgtgatc    1560
agcggtccag ttttaccgg cggtgacctg gtgcgcctga acaacagcgg caacaatatc    1620
caaaaccgtg gttatatcga agtcccgatt caattcatca gcacgagcac ccgttaccgc    1680
gtccgtgttc gctacgcatc cgttacgccg atccgcctga gcgttaactg ggcaattcc    1740 aacattttca gcagcattgt ccctgctacg gcgacctctc tggacaattt gcagagccgt    1800
aacttcggct atttcgaaag ccgcaacgct ttcaccagcg ctacgggcaa tgtggttggt    1860
gttcgcaatt tcagcgagaa tgcgggcgtc atcattgacc gttttgagtt tatcccggtg    1920
accgcgacct tcgaagcgga gtacgatctg gagcgtgcgc aggaa                   1965
```

<210> SEQ ID NO 27
<211> LENGTH: 655
<212> TYPE: PRT
<213> ORGANISM: Artificial Sequence
<220> FEATURE:
<223> OTHER INFORMATION: Cry1B variant

<400> SEQUENCE: 27

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Ala Ile
            100                 105                 110

Thr Leu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
```

-continued

```
            195                 200                 205
Thr Ser Gln Glu Ile Gln Arg Tyr Tyr Glu Arg Gln Ala Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Ile Tyr Pro Ile Asn Thr Ser Ala Gln Leu Thr
                275                 280                 285

Arg Glu Ile Tyr Thr Asp Pro Ile Gly Arg Thr Asn Ala Pro Ser Gly
                290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
                340                 345                 350

Met Asn Tyr Trp Val Gly His Arg Leu Tyr Phe Arg Pro Ile Gln Gly
                355                 360                 365

Thr Leu Asn Thr Ser Thr His Gly Ala Thr Asn Thr Ser Ile Asn Pro
370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
                435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
                500                 505                 510

Phe Leu Phe Asn Gly Ser Val Ile Ser Gly Pro Gly Phe Thr Gly Gly
                515                 520                 525

Asp Leu Val Arg Leu Asn Asn Ser Gly Asn Asn Ile Gln Asn Arg Gly
                530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ile Val Pro Ala Thr Ala Thr
                580                 585                 590

Ser Leu Asp Asn Leu Gln Ser Arg Asn Phe Gly Tyr Phe Glu Ser Arg
                595                 600                 605

Asn Ala Phe Thr Ser Ala Thr Gly Asn Val Val Gly Val Arg Asn Phe
610                 615                 620
```

```
Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 28
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 28
atgccgagca atcgtaagaa tgaaaatgaa atcattaacg cactgtccat ccctgcagtg     60
agcaatcaca gcgcgcagat ggatttgagc ctggatgcgc gtatcgagga cagcctgtgt    120
attgccgagg gcaacaacat caatccgttg gtcagcgcga gcaccgtgca aaccggcatt    180
aacattgccg gtcgtatcct gggtgtcctg ggcgttccgt ttgcgggtca gctggcgagc    240
ttttacagct ttatcgttgg tgagttgtgg ccgtcgggtc gtgacccttg ggagattttc    300
atggagcacg tcgagcaact ggtgcgccaa gcgattacgc tgaatgcgcg caacaccgct    360
ctggcgcgtc tgcaaggtct gggtgcaagc ttccgcgctt accagcagtc cctggaagat    420
tggttggaaa accgtgataa tgcgcgcact cgctccgtcc tgtacacgca gtacatcgcg    480
ctggagctgg acttcttgaa cgcgatgccg ctgtttgcaa tcaacaacca gcaagtgccg    540
ctgctgatgg tctacgccca agccgcgaat ctgcacttgc tgctgctgcg cgacgcatct    600
ctgttcggta gcgaatttgg cctgaccagc caggagatcc agcgctacta tgagcgtcag    660
gccgagaaaa cgcgtgaata ctccgactac tgcgctcgtt ggtacaacac gggtctgaac    720
aatctgcgtg gcaccaacgc ggagtcctgg ctgcgttaca accagtttcg tcgcgatctg    780
accctgggtg ttttggattt ggttgcgctg tttccgagct atgacacccg catctatccg    840
atcaacacca gcgcgcaact gactcgtgaa atctatacgg acccgattgg ccgcactaat    900
gcaccgtccg gtttcgcaag caccaactgg ttcaataaca atgcaccgag cttcagcgcg    960
atcgaggccg cgatctttcg tccgccgcac ctgttggact tcccggagca gctgaccatc   1020
tactctgcat ctagccgttg gagcagcacg cagcacatga attactgggt tggccatcgt   1080
ctgtatttcc gcccgattca gggtacgctg aacactagca cgcacggtgc cactaacacg   1140
agcatcaacc cggtgacgct gcaattcacc agccgtgatg tttaccgtac cgagtcctac   1200
gccggcatca acattctgct gaccaccccg gttaacggcg tcccttgggc tcgtttcaat   1260
tggcgtaacc cactgaatag cctgcgtggt tctttgctgt acaccattgg ttataccggc   1320
gtcggtacgc aactgtttga ctcggaaact gagctgccac cggaaactac cgagcgtccg   1380
aactacgaat cttatagcca ccgtctgtcc aatatccgtc tgatcatcgg caacaccctg   1440
cgtgcgccgg tgtacagctg gacccatcgt agcgccgatc gcacgaacac gattgccacc   1500
aacattatca cccagatccc ggcagtgaaa ggcaactttc tgtttaacgg cagcgtgatc   1560
agcggtccag gttttaccgg cggtgacctg gtgcgcctga acaacagcgg caacaatatc   1620
caaaaccgtg gttatatcga agtcccgatt caattcatca gcacgagcac ccgttaccgc   1680
gtccgtgttc gctacgcatc cgttacgccg atccgcctga gcgttaactg gggcaattcc   1740
aacattttca gcagcattgt ccctgctacg gcgacctctc tggacaattt gcagagccgt   1800
aacttcggct atttcgaaag ccgcaacgct ttcaccagcg ctacgggcaa tgtggttggt   1860
```

```
gttcgcaatt tcagcgagaa tgcgggcgtc atcattgacc gttttgagtt tatcccggtg    1920
accgcgacct tcgaagcgga gtacgatctg gagcgtgcgc aggaa                    1965
```

<210> SEQ ID NO 29
<211> LENGTH: 663
<212> TYPE: PRT
<213> ORGANISM: Artificial Sequence
<220> FEATURE:
<223> OTHER INFORMATION: Cry1B variant

<400> SEQUENCE: 29

```
Met Pro Ser Asn Arg Lys Asn Glu Asn Glu Ile Ile Asn Ala Val Ser
1               5                   10                  15

Asn His Ser Ala Gln Met Asp Leu Ser Leu Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Ser Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Met
                85                  90                  95

Glu His Val Glu Gln Ile Val Arg Gln Gln Ile Thr Asp Ser Val Arg
            100                 105                 110

Asp Thr Ala Ile Ala Arg Leu Glu Gly Leu Gly Arg Gly Tyr Arg Ser
        115                 120                 125

Tyr Gln Gln Ala Leu Glu Thr Trp Leu Asp Asn Arg Asn Asp Ala Arg
    130                 135                 140

Ser Arg Ser Ile Ile Arg Glu Arg Tyr Ile Ala Leu Glu Leu Asp Ile
145                 150                 155                 160

Thr Thr Ala Ile Pro Leu Phe Ser Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Trp Gly Met Ser Ser Ser Asp Val
        195                 200                 205

Asn Gln Tyr Tyr Gln Glu Gln Ile Arg Tyr Thr Glu Glu Tyr Ser Asn
    210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Val Tyr Pro Met Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
    290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350
```

Gly His Arg Leu Asn Phe Arg Pro Ile Gly Gly Thr Leu Asn Thr Ser
            355                 360                 365

Thr Gln Gly Leu Thr Asn Asn Thr Ser Ile Asn Pro Val Thr Leu Gln
    370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
        435                 440                 445

Leu Pro Pro Glu Thr Thr Glu Arg Pro Asn Tyr Glu Ser Tyr Ser His
    450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
            500                 505                 510

Gly Gly Thr Ser Val Ile Thr Gly Pro Gly Phe Thr Gly Gly Asp Ile
        515                 520                 525

Leu Arg Arg Asn Thr Phe Gly Asp Phe Val Ser Leu Gln Val Asn Ile
    530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
        595                 600                 605

Asn Pro Phe Ser Phe Arg Ala Asn Pro Asp Ile Ile Gly Ile Ser Glu
    610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Arg Ala Gln Lys
            660

<210> SEQ ID NO 30
<211> LENGTH: 1989
<212> TYPE: DNA
<213> ORGANISM: Artificial Sequence
<220> FEATURE:
<223> OTHER INFORMATION: coding sequence of Cry1B variant

<400> SEQUENCE: 30
atgccttcaa ataggaaaaa tgagaatgaa attataaatg ctgtatcgaa tcattccgca      60
caaatggatc tatcgctaga tgctcgtatt gaagatagct tgtgtgtagc cgaggtgaac     120
aatattgatc catttgttag cgcatcaaca gtccaaacag gtattagtat agctggtaga     180
atattgggcg tattaggtgt gccgtttgct ggacaactag ctagttttta tagttttctt     240

```
gttggggaat tatggcctag cggcagagat ccatgggaaa tttttatgga acatgtcgag      300
caaattgtaa gacaacaaat aacggacagt gttaggata ccgctattgc tcgtttagaa      360
ggtctaggaa gagggtatag atcttaccag caggctcttg aaacttggtt agataaccga      420
aatgatgcaa gatcaagaag cattattcgt gagagatata ttgctttaga acttgacatt      480
actactgcta taccgctttt cagcatacga aatcaagagg ttccattatt aatggtatat      540
gctcaagctg caaatttaca cctattatta ttgagagacg catcccttt tggtagtgaa       600 tgggggatgt catcttccga tgttaaccaa tattaccaag aacaaatcag atatacagag      660
gaatattcta accattgcgt acaatggtat aatacagggc taaataactt aagagggaca      720
aatgctgaaa gttggttgcg gtataatcaa ttccgtagag atctaacgtt aggagtatta      780
gatctagtgg cactattccc aagctatgac acgcgtgttt atccaatgaa tacgagtgct      840
cagttaacaa gagaaattta tacagatcca attggagaga caaatgcacc ttcaggattt      900
gcaagtacga attggtttaa taataatgca ccatcgtttt ctgccataga ggctgccatt      960
ttcaggcctc cgcatctact tgattttcca gaacaactta caatttacag tgcatcaagc     1020
cgttggagta gcactcaaca tatgaattat tgggtgggac ataggcttaa cttccgccca     1080
ataggaggga cattaaatac ctcaacacaa ggacttacta taatacttc aattaatcct      1140 gtaacattac agtttacgtc tcgtgacgtt tatagaacag aatcaaatgc agggacaaat     1200
atactattta ctactcctgt gaatggagta ccttgggcta gatttaattt tataaaccct     1260
cagaatattt atgaaagagg cgccactacc tacagtcaac cgtatcaggg agttgggatt     1320
caattatttg attcagaaac tgaattacca ccagaaacaa cagaacgacc aaattatgaa     1380
tcatatagtc atagattatc tcatataggg ctaatcatag gaaacacttt gagagcacca     1440
gtctattctt ggacgcatcg tagtgcaact cttacaaata caattgatcc agagagaatt     1500
aatcaaatac ctttagtgaa aggatttaga gtttgggggg gcacctctgt cattacagga     1560
ccaggattta caggaggga tatccttcga agaaatacct ttggtgattt tgtatctcta     1620
caagtcaata ttaattcacc aattacccaa agataccgtt taagatttcg ttacgcttcc     1680
agtagggatg cacgagttat agtattaaca ggagcggcat ccacaggagt ggggaggccaa     1740 gttagtgtaa atatgcctct tcagaaaact atggaaatag gggagaactt aacatctaga     1800
acatttagat ataccgattt tagtaatcct ttttcattta gagctaatcc agatataatt     1860
gggataagtg aacaacctct atttggtgca ggttctatta gtagcggtga actttatata     1920
gataaaattg aaattattct agcagatgca acatttgaag cagaatctga tttagaaaga     1980
gcacaaaag                                                              1989
```

<210> SEQ ID NO 31
<211> LENGTH: 663
<212> TYPE: PRT
<213> ORGANISM: Artificial Sequence
<220> FEATURE:
<223> OTHER INFORMATION: Cry1B variant

<400> SEQUENCE: 31

```
Met Pro Ser Asn Arg Lys Asn Glu Asn Glu Ile Ile Asn

```
Ser Thr Val Gln Thr Gly Ile Ser Ile Ala Gly Arg Ile Leu Gly Val
    50                  55                  60

Leu Gly Val Pro Phe Ala Gly Gln Leu Ala Ser Phe Tyr Ser Phe Leu
 65              70                  75                      80

Val Gly Glu Leu Trp Pro Ser Gly Arg Asp Pro Trp Glu Ile Phe Met
                 85                  90                  95

Glu His Val Glu Gln Ile Val Arg Gln Gln Ile Thr Asp Ser Val Arg
            100                 105                 110

Asp Thr Ala Ile Ala Arg Leu Glu Gly Leu Gly Arg Gly Tyr Arg Ser
            115                 120                 125

Tyr Gln Gln Ala Leu Glu Thr Trp Leu Asp Asn Arg Asn Asp Ala Arg
130                 135                 140

Ser Arg Ser Ile Ile Arg Glu Arg Tyr Ile Ala Leu Glu Leu Asp Ile
145                 150                 155                 160

Thr Thr Ala Ile Pro Leu Phe Ser Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Trp Gly Met Ser Ser Ser Asp Val
            195                 200                 205

Asn Gln Tyr Tyr Gln Glu Gln Ile Arg Tyr Thr Glu Glu Tyr Ser Asn
210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Ile Tyr Thr
            275                 280                 285

Asp Pro Ile Gly Arg Thr Asn Ala Pro Ser Gly Phe Ala Ser Thr Asn
            290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
            355                 360                 365

Thr Gln Gly Leu Thr Asn Asn Thr Ser Ile Asn Pro Val Thr Leu Gln
370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
            435                 440                 445

Leu Pro Pro Glu Thr Thr Glu Arg Pro Asn Tyr Glu Ser Tyr Ser His
450                 455                 460

Arg Leu Ser His Ile Gly Leu Ile Ile Gly Asn Thr Leu Arg Ala Pro
```

```
                465                 470                 475                 480
Val Tyr Ser Trp Thr His Arg Ser Ala Thr Leu Thr Asn Thr Ile Asp
                    485                 490                 495
Pro Glu Arg Ile Asn Gln Ile Pro Leu Val Lys Gly Phe Arg Val Trp
                500                 505                 510
Gly Gly Thr Ser Val Ile Thr Gly Pro Gly Phe Thr Gly Gly Asp Ile
            515                 520                 525
Leu Arg Arg Asn Thr Phe Gly Asp Phe Val Ser Leu Gln Val Asn Ile
        530                 535                 540
Asn Ser Pro Ile Thr Gln Arg Tyr Arg Leu Arg Phe Arg Tyr Ala Ser
545                 550                 555                 560
Ser Arg Asp Ala Arg Val Ile Val Leu Thr Gly Ala Ala Ser Thr Gly
                565                 570                 575
Val Gly Gly Gln Val Ser Val Asn Met Pro Leu Gln Lys Thr Met Glu
                580                 585                 590
Ile Gly Glu Asn Leu Thr Ser Arg Thr Phe Arg Tyr Thr Asp Phe Ser
            595                 600                 605
Asn Pro Phe Ser Phe Arg Ala Asn Pro Asp Ile Ile Gly Ile Ser Glu
        610                 615                 620
Gln Pro Leu Phe Gly Ala Gly Ser Ile Ser Ser Gly Glu Leu Tyr Ile
625                 630                 635                 640
Asp Lys Ile Glu Ile Ile Leu Ala Asp Ala Thr Phe Glu Ala Glu Ser
                645                 650                 655
Asp Leu Glu Gly Ala Arg Lys
            660
```

<210> SEQ ID NO 32
<211> LENGTH: 1989
<212> TYPE: DNA
<213> ORGANISM: Artificial Sequence
<220> FEATURE:
<223> OTHER INFORMATION: coding sequence of Cry1B variant

<400> SEQUENCE: 32

```
atgccttcaa ataggaaaaa tgagaatgaa attataaatg ctgtatcgaa tcattccgca    60
caaatggatc tatcgctaga tgctcgtatt gaagatagct tgtgtgtagc cgaggtgaac   120
aatattgatc catttgttag cgcatcaaca gtccaaacag gtattagtat agctggtaga   180
atattgggcg tattaggtgt gccgtttgct ggacaactag ctagttttta gtttttctt    240
gttggggaat tatggcctag cggcagagat ccatgggaaa ttttttatgga acatgtcgag   300
caaattgtaa gacaacaaat aacggacagt gttagggata ccgctattgc tcgtttagaa   360
ggtctaggaa gagggtatag atcttaccag caggctcttg aaacttggtt agataaccga   420
aatgatgcaa gatcaagaag cattattcgt gagagatata ttgctttaga acttgacatt   480
actactgcta taccgctttt cagcatacga aatcaagagg ttccattatt aatggtatat   540
gctcaagctg caaatttaca cctattatta ttgagagacg catcccttt tggtagtgaa   600
tgggggatgt catcttccga tgttaaccaa tattaccaag aacaaatcag atatacagag   660
gaatattcta accattgcgt acaatggtat aatacagggc taaataactt aagagggaca   720
aatgctgaaa gttggttgcg gtataatcaa ttccgtagag atctaacgtt aggagtatta   780
gatctagtgg cactattccc aagctatgac actcgcactt atccaatcaa tacgagtgct   840
cagttaacaa gagaaattta tacagatcca attggggagaa caaatgcacc ttcaggattt   900
gcaagtacga attggtttaa taataatgca ccatcgtttt ctgccataga ggctgccatt   960
```

```
ttcaggcctc cgcatctact tgattttcca gaacaactta caatttacag tgcatcaagc    1020
cgttggagta gcactcaaca tatgaattat tgggtgggac ataggcttaa cttccgccca    1080
ataggaggga cattaaatac ctcaacacaa ggacttacta ataatacttc aattaatcct    1140
gtaacattac agtttacgtc tcgtgacgtt tatagaacag aatcaaatgc agggacaaat    1200
atactattta ctactcctgt gaatggagta ccttgggcta gatttaattt tataaaccct    1260
cagaatattt atgaaagagg cgccactacc tacagtcaac cgtatcaggg agttgggatt    1320
caattatttg attcagaaac tgaattacca ccagaaacaa cagaacgacc aaattatgaa    1380
tcatatagtc atagattatc tcatatagga ctaatcatag aaacacttt gagagcacca    1440 gtctattctt ggacgcatcg tagtgcaact cttacaaata caattgatcc agagagaatt    1500
aatcaaatac ctttagtgaa aggatttaga gtttgggggg gcacctctgt cattacagga    1560
ccaggattta caggagggga tatccttcga agaaatacct ttggtgattt tgtatctcta    1620
caagtcaata ttaattcacc aattacccaa agataccgtt taagatttcg ttacgcttcc    1680
agtagggatg cacgagttat agtattaaca ggagcggcat ccacaggagt gggaggccaa    1740
gttagtgtaa atatgcctct tcagaaaact atggaaatag gggagaactt aacatctaga    1800
acatttagat ataccgattt tagtaatcct tttcattta gagctaatcc agatataatt    1860
gggataagtg aacaacctct atttggtgca ggttctatta gtagcggtga actttatata    1920
gataaaattg aaattattct agcagatgca acatttgaag cagaatctga tttagaaggg    1980
gcgcggaag                                                           1989
```

<210> SEQ ID NO 33
<211> LENGTH: 663
<212> TYPE: PRT
<213> ORGANISM: Artificial Sequence
<220> FEATURE:
<223> OTHER INFORMATION: Cry1B variant

<400> SEQUENCE: 33

```
Met Pro Ser Asn Arg Lys Asn Glu Asn Glu Ile Ile Asn Ala Val Ser
1               5                   10                  15

Asn His Ser Ala Gln Met Asp Leu Ser Leu Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Met
                85                  90                  95

Glu His Val Glu Gln Ile Val Arg Gln Gln Ile Thr Asp Ser Val Arg
            100                 105                 110

Asp Thr Ala Ile Ala Arg Leu Glu Gly Leu Gly Arg Gly Tyr Arg Ser
        115                 120                 125

Tyr Gln Gln Ala Leu Glu Thr Trp Leu Asp Asn Arg Asn Asp Ala Arg
    130                 135                 140

Ser Arg Ser Ile Ile Leu Glu Arg Tyr Ile Ala Leu Glu Leu Asp Ile
145                 150                 155                 160

Thr Thr Ala Ile Pro Leu Phe Ser Ile Arg Asn Gln Glu Val Pro Leu
                165                 170                 175
```

```
Leu Met Val Tyr Ala Gln Ala Ala Asn Leu His Leu Leu Leu Arg
            180                 185                 190

Asp Ala Ser Leu Phe Gly Ser Glu Trp Gly Met Ala Ser Ser Asp Val
            195                 200                 205

Asn Gln Tyr Tyr Gln Glu Gln Ile Arg Tyr Thr Glu Glu Tyr Ser Asn
        210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
    290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
        355                 360                 365

Thr Gln Gly Leu Thr Asn Asn Thr Ser Ile Asn Pro Val Thr Leu Gln
    370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
        435                 440                 445

Leu Pro Pro Glu Thr Thr Glu Arg Pro Asn Tyr Glu Ser Tyr Ser His
    450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
            500                 505                 510

Gly Gly Thr Ser Val Ile Thr Gly Pro Gly Phe Thr Gly Gly Asp Ile
        515                 520                 525

Leu Arg Arg Asn Thr Phe Gly Asp Phe Val Ser Leu Gln Val Asn Ile
    530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590
```

```
Ile Gly Glu Asn Leu Thr Ser Arg Thr Phe Arg Tyr Thr Asp Phe Ser
        595                 600                 605

Asn Pro Phe Ser Phe Arg Ala Asn Pro Asp Ile Gly Ile Ser Glu
    610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Lys Ala Gln Lys
        660

<210> SEQ ID NO 34
<211> LENGTH: 1989
<212> TYPE: DNA
<213> ORGANISM: Artificial Sequence
<220> FEATURE:
<223> OTHER INFORMATION: coding sequence of Cry1B variant

<400> SEQUENCE: 34
```

| | | |
|---|---|---|
| atgccttcaa ataggaaaaa tgagaatgaa attataaatg ctgtatcgaa tcattccgca | 60 |
| caaatggatc tatcgctaga tgctcgtatt gaagatagct tgtgtgtagc cgaggtgaac | 120 |
| aatattgatc catttgttag cgcatcaaca gtccaaacgg gtattaacat agctggtaga | 180 |
| atactaggcg tattaggggt gccgtttgct ggacaactag ctagttttta tagttttctt | 240 |
| gttggggaat tatggcctag cggcagagat ccatgggaaa tttttatgga acatgtcgag | 300 |
| caaattgtaa gacaacaaat aacggacagt gttaggggata ccgctattgc tcgtttagaa | 360 |
| ggtctaggaa gagggtatag atcttaccag caggctcttg aaacttggtt agataaccga | 420 |
| aatgatgcaa gatcaagaag cattattctt gagcgctata ttgctttaga acttgacatt | 480 |
| actactgcta taccgctttt cagcatacga aatcaagagg ttccattatt gatggtatat | 540 |
| gctcaagctg caaatttaca cctattatta ttgagagacg catccctttt ggtagtgaa | 600 |
| tgggggatgg catcttccga tgttaaccaa tattaccaag aacaaatcag atatacagag | 660 |
| gaatattcta accattgcgt acaatggtat aatacagggc taaataactt aagagggaca | 720 |
| aatgctgaaa gttggttgcg gtataatcaa ttccgtagag acctaacgtt aggggtatta | 780 |
| gatttagtag ccctattccc aagctatgat actcgcactt atccaatcaa tacgagtgct | 840 |
| cagttaacaa gagaaattta tacagatcca attggggaga caaatgcacc ttcaggattt | 900 |
| gcaagtacga attggtttaa taataatgca ccatcgtttt ctgccataga ggctgccatt | 960 |
| ttcaggcctc cgcatctact tgattttcca gaacaactta caatttacag tgcatcaagc | 1020 |
| cgttggagta gcactcaaca tatgaattat tgggtgggac ataggcttaa cttccgccca | 1080 |
| ataggaggga cattaaatac ctcaacacaa ggacttacta ataatacttc aattaatcct | 1140 |
| gtaacattac agtttacgtc tcgtgacgtt tatagaacag aatcaaatgc agggacaaat | 1200 |
| atactattta ctactcctgt gaatggagta ccttgggcta gatttaattt tataaaccct | 1260 |
| cagaatattt atgaaagagg cgccactacc tacagtcaac cgtatcaggg agttgggatt | 1320 |
| caattatttg attcagaaac tgaattacca ccagaaacaa cagaacgacc aaattatgaa | 1380 |
| tcatatagtc atagattatc tcatatagga ctaatcatag aaacactttt gagagcacca | 1440 |
| gtctattctt ggacgcatcg tagtgcaact cttacaaata caattgatcc agagagaatt | 1500 |
| aatcaaatac ctttagtgaa aggatttaga gtttgggggg gcacctctgt cattacagga | 1560 |
| ccaggattta caggagggga tatccttcga agaaatacct ttggtgattt tgtatctcta | 1620 |

```
caagtcaata ttaattcacc aattacccaa agataccgtt taagatttcg ttacgcttcc    1680
agtagggatg cacgagttat agtattaaca ggagcggcat ccacaggagt gggaggccaa    1740
gttagtgtaa atatgcctct tcagaaaact atggaaatag gggagaactt aacatctaga    1800
acatttagat ataccgattt tagtaatcct ttttcattta gagctaatcc agatataatt    1860
gggataagtg aacaacctct atttggtgca ggttctatta gtagcggtga actttatata    1920
gataaaattg aaattattct agcagatgca acatttgaag cagaatctga tttagagaaa    1980
gctcagaaa                                                            1989

<210> SEQ ID NO 35
<211> LENGTH: 663
<212> TYPE: PRT
<213> ORGANISM: Artificial Sequence
<220> FEATURE:
<223> OTHER INFORMATION: Cry1B variant

<400> SEQUENCE: 35

Met Pro Ser Asn Arg Lys Asn Glu Asn Glu Ile Ile Asn Ala Val

```
            290                 295                 300
Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
                355                 360                 365

Thr Gln Gly Leu Thr Asn Asn Thr Ser Ile Asn Pro Val Thr Leu Gln
        370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
                420                 425                 430

Gln Pro Tyr Gln Gly Val Gly Ile Gln Leu Phe Asp Ser Glu Thr Glu
            435                 440                 445

Leu Pro Pro Glu Thr Thr Glu Arg Pro Asn Tyr Glu Ser Tyr Ser His
        450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
            500                 505                 510

Gly Gly Thr Ser Val Ile Thr Gly Pro Gly Phe Thr Gly Gly Asp Ile
            515                 520                 525

Leu Arg Arg Asn Thr Phe Gly Asp Phe Val Ser Leu Gln Val Asn Ile
        530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
            595                 600                 605

Asn Pro Phe Ser Phe Arg Ala Asn Pro Asp Ile Ile Gly Ile Ser Glu
        610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Arg Ala Gln Lys
            660

<210> SEQ ID NO 36
<211> LENGTH: 1989
<212> TYPE: DNA
<213> ORGANISM: Artificial Sequence
<220> FEATURE:
<223> OTHER INFORMATION: coding sequence of Cry1B variant
```

<400> SEQUENCE: 36

```
atgccttcaa ataggaaaaa tgagaatgaa attataaatg ctgtatcgaa tcattccgca      60
caaatggatc tatcgctaga tgctcgtatt gaagatagct tgtgtgtagc cgaggtgaac     120
aatattgatc catttgttag cgcatcaaca gtccaaacag gtattagtat agctggtaga     180
atattgggcg tattaggtgt gccgtttgct ggacaactag ctagttttta gtttttctt     240
gttggggaat tatggcctag cggcagagat ccatgggaaa ttttcctgga acatgtcgaa     300
caacttataa gacaacaagt aacagaaaat actaggaata cggctattgc tcgattagaa     360
ggtctaggaa gaggctatag atcttaccag caggctcttg aaacttggtt agataaccga     420
aatgatgcaa gatcaagaag cattattctt gagcgctatg ttgctttaga acttgacatt     480
actactgcta taccgctttt cagcatacga atcaagagg ttccattatt aatggtatat      540
gctcaagctg caaatttaca cctattatta ttgagagacg catccctttt tggtagtgaa     600
tgggggatgt catctgccga tgttaaccaa tattaccaag aacaaatcag atatacagag     660
gaatattcta accattgcgt acaatggtat aatacagggc taaataactt aagagggaca     720
aatgctgaaa gttggttgcg gtataatcaa ttccgtagag acctaacgtt aggggtatta     780
gatttagtag ccctattccc aagctatgac actcgcactt atccaatcaa tacgagtgct     840
cagttaacaa gagaaattta tacagatcca attgggagaa caaatgcacc ttcaggattt     900
gcaagtacga attggtttaa taataatgca ccatcgtttt ctgccataga ggctgccatt     960
ttcaggcctc cgcatctact tgattttcca gaacaactta caatttacag tgcatcaagc    1020
cgttggagta gcactcaaca tatgaattat tgggtgggac ataggcttaa cttccgccca    1080
ataggaggga cattaaatac ctcaacacaa ggacttacta ataatacttc aattaatcct    1140
gtaacattac agtttacgtc tcgtgacgtt tatagaacga atcaaatgc agggacaaat     1200
atactattta ctactcctgt gaatggagta ccttgggcta gatttaattt tataaaccct    1260
cagaatattt atgaaagagg cgccactacc tacagtcaac cgtatcaggg agttgggatt    1320
caattatttg attcagaaac tgaattacca ccagaaacaa cagaacgacc aaattatgaa    1380
tcatatagtc atagattatc tcatatagga ctaatcatag gaaacacttt gagagcacca    1440
gtctattctt ggacgcatcg tagtgcaact cttacaaata caattgatcc agagagaatt    1500
aatcaaatac ctttagtgaa aggatttaga gtttgggggg gcacctctgt cattacagga    1560
ccaggattta caggagggga tatccttcga agaaatacct ttggtgattt tgtatctcta    1620
caagtcaata ttaattcacc aattacccaa agataccgtt taagatttcg ttacgcttcc    1680
agtagggatg cacgagttat agtattaaca ggagcggcat ccacaggagt gggaggccaa    1740
gttagtgtaa atatgcctct tcagaaaact atggaaatag gggagaactt aacatctaga    1800
acatttagat ataccgattt tagtaatcct ttttcattta gagctaatcc agatataatt    1860
gggataagtg aacaacctct atttggtgca ggttctatta gtagcggtga acttatata    1920
gataaaattg aaattattct agcagatgca acatttgaag cagaatctga tttagaaaga    1980
gcacaaaag                                                            1989
```

<210> SEQ ID NO 37
<211> LENGTH: 655
<212> TYPE: PRT
<213> ORGANISM: Artificial Sequence
<220> FEATURE:
<223> OTHER INFORMATION: Cry1B variant

<400> SEQUENCE: 37

-continued

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln His Ile
                100                 105                 110

Thr Glu Asn Ala Arg Asn Thr Ala Leu Ala Arg Leu Gln Gly Leu Gly
                115                 120                 125

Ala Ser Phe Arg Ala Tyr Gln Gln Ser Leu Glu Asp Trp Leu Glu Asn
130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
                195                 200                 205

Thr Ser Gln Glu Ile Gln Arg Tyr Tyr Glu Arg Gln Ala Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Ile Tyr Pro Ile Asn Thr Ser Ala Gln Leu Thr
                275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
                340                 345                 350

Met Asn Tyr Trp Val Gly His Arg Leu Asn Phe Arg Pro Ile His Gly
                355                 360                 365

Thr Leu Asn Thr Ser Thr His Gly Ala Thr Asn Thr Ser Ile Asn Pro
370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415
```

```
Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Ser Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Tyr Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 38
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 38
atgccctcca accgcaagaa cgagaacgag ataatcaacg ccctgtcgat cccagccgtc      60
tccaaccact ccgcgcagat ggacctctca ctggacgctc gcatcgagga ctcactctgc     120
atcgccgagg gcaacaacat caacccgctc gtcagcgcct cgaccgtgca gactggcatc     180
aacatcgccg gtcgcatact cggcgtcctc ggagtcccat tcgcaggtca gctggcgagc     240
ttctacagct tcatcgtcgg cgagctctgg ccatcaggtc gcgatccctg ggagatcttc     300
atggagcacg tcgagcagct ggtcaggcag cacatcacgg agaacgctcg caacacggct     360
ctcgccagac tccaaggcct cggagccagc ttcagagcct accagcagtc cctcgaggac     420
tggctcgaga accgcgacaa cgcgaggacc cggagcgtcc tctacaccca gtacatcgcg     480
ctggagctcg acttcctgaa cgcgatgcca ctcttcgcca tcaacaacca gcaggtgccg     540
ctcctcatgg tctacgccca agctgccaac ctccacctcc tgctcctcag agacgctagc     600
ctgttcggca gcgagttcgg actcacgtcg caggagatcc agcgctacta cgagcgccag     660
gcggagaaga cccgggagta cagcgactac tgcgcacgct ggtacaacac cggcctgaac     720
```

```
aacctgcgcg gcacgaacgc tgagagctgg ctccgctaca accagttccg cagggacctc    780
acactcggag tcctcgacct cgtcgcgctg ttcccgagct acgacacgcg gatctacccg    840
atcaacacga gcgcgcagct cactcgcgag atctacacgg accccatcgg tcgcacgaac    900
gctccatccg gcttcgcctc caccaactgg ttcaacaaca acgcgccgtc gttcagcgcc    960
atcgaagctg caatcttccg cccacctcac ctgctggact cccagagca gctcaccatc   1020 tacagcgcct ccagccgctg gtccagcacg cagcacatga actactgggt cggccaccgc   1080
ctcaacttca ggcctatcca cggtaccctc aacacctcga cccacggcgc cacgaacacg   1140
tccatcaacc cggtgacgct ccagttcacg agccgggacg tctaccgcac tgagagctac   1200
gctggcatca acatcctgct cacgacgcca gtgaacggcg tcccgtgggc acgcttcaac   1260
tggaggaacc ctctcaactc cctgcgcgga tcgctcctct acaccatcgg ctacaccgga   1320
gtcggtaccc agctcttcga cagcgagacc gagctcccac ctgagaccac cgagaggccc   1380
aactacgaga gctactccca ccgcctgtcg aacatccgcc tcatcatctc caacacgctc   1440
agagctcccg tctactcctg gacgcacagg tcagctgacc ggacgaacac catcgcgacg   1500
aacatcatca cccagatccc ggccgtcaag ggcaacttcc tcttcaacgg ctccgtcatc   1560
tccggaccag gcttcaccgg aggagacctc gtccgcctca caactccgg caacaacatc   1620 tacaaccggg gctacatcga ggtgccgatc cagttcatct ccacgagcac tcggtaccgc   1680
gtcagagtgc gctacgcgag cgtcactccg atccgcctct ccgtcaactg ggcaactcg   1740 aacatcttca gctccatcgt cccagccacc gcgactagcc tcgacaacct gcagtcccgc   1800
aacttcggct acttcgagag ccgcaacgcc ttcacgagcg cgactggcaa cgtcgtcggc   1860
gtccgcaact tctccgagaa cgccggagtg atcatcgacc gcttcgagtt catccccgtg   1920
accgcgacct cgaggccgga gtacgacctt gagagagctc aggaggcc                1968

<210> SEQ ID NO 39
<211> LENGTH: 655
<212> TYPE: PRT
<213> ORGANISM: Artificial Sequence
<220> FEATURE:
<223> OTHER INFORMATION: Cry1B variant

<400> SEQUENCE: 39

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln His Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140
```

```
Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
            165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
            325                 330                 335

Gln Leu Thr Ile Tyr Ser Ala Ser Ser Arg Trp Ser Thr Gln His
            340                 345                 350

Met Asn Tyr Trp Val Gly His Arg Leu Asn Phe Arg Pro Ile His Gly
            355                 360                 365

Thr Leu Asn Thr Ser Thr His Gly Ala Thr Asn Thr Ser Ile Asn Pro
        370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
        450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
            485                 490                 495

Thr Ile Ala Thr Asn Ile Ile Thr Gln Ile Pro Ala Val Lys Gly Asn
        500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Tyr Asn Arg Gly
        530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
```

|      |      | 565  |      |      | 570  |      |      |      | 575  |      |      |
|------|------|------|------|------|------|------|------|------|------|------|------|
| Trp  | Gly  | Asn  | Ser  | Asn  | Ile  | Phe  | Ser  | Thr  | Ile  | Val  | Pro  | Ala | Thr | Ala | Thr |

Trp Gly Asn Ser Asn Ile Phe Ser Thr Ile Val Pro Ala Thr Ala Thr
          565                 570                 575
                    580                 585                 590

Ser Leu Asp Asn Leu Gln Ser Arg Asn Phe Gly Tyr Phe Glu Ser Arg
            595                 600                 605

Asn Ala Phe Thr Ser Ala Thr Gly Asn Val Val Gly Val Arg Asn Phe
        610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 40
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 40

```
atgccctcca accgcaagaa cgagaacgag ataatcaacg ccctgtcgat cccagccgtc    60
tccaaccact ccgcgcagat ggacctctca ctggacgctc gcatcgagga ctcactctgc   120
atcgccgagg caacaacat caacccgctc gtcagcgcct cgaccgtgca gactggcatc   180
aacatcgccg tcgcatact cggcgtcctc ggagtcccat cgcaggtca gctggcgagc   240
ttctacagct tcatcgtcgg cgagctctgg ccatcaggtc gcgatccctg ggagatcttc   300
atggagcacg tcgagcagct ggtcaggcag cacatcacgg agaacgctcg caacacggct   360
ctcgccagac tccaaggcct cggagccagc ttcagagcct accagcagtc cctcgaggac   420
tggctcgaga ccgcgacaa cgcgaggacc cggagcgtcc tctacaccca gtacatcgcg   480
ctggagctcg acttcctgaa cgcgatgcca ctcttcgcca tcaacaacca gcaggtgccg   540
ctcctcatgg tctacgccca agctgccaac ctccacctcc tgctcctcag agacgctagc   600
ctgttcggca gcgagttcgg actcacgtcg caggagatcc agcgctacta cgagcgccag   660
gcggagaaga cccgggagta cagcgactac tgcgcacgct ggtacaacac cggcctgaac   720
aacctgcgcg gcacgaacgc tgagagctgg ctccgctaca accagttccg cagggacctc   780
acactcggag tcctcgaccc tgtcgcgctg ttcccgagct acgacacgcg gatctacccg   840
atcaacacga gcgcgcagct cactcgcgag atctacacgg accccatcgg tcgcacgaac   900
gctccatccg gcttcgcctc caccaactgg ttcaacaaca acgcgccgtc gttcagcgcc   960
atcgaagctg caatcttccg cccacctcac ctgctggact cccagagca gctcaccatc  1020
tacagcgcct ccagccgctg gtccagcacg cagcacatga actactgggt cggccaccgc  1080
ctcaacttca ggcctatcca cggtacccct caacacctcga cccacggcgc cacgaacacg  1140
tccatcaacc cggtgacgct ccagttcacg agccggacg tctaccgcac tgagagctac  1200
gctggcatca acatcctgct cacgacgcca gtgaacggcg tcccgtgggc acgcttcaac  1260
tggaggaacc ctctcaactc cctgcgcgga tcgctcctct acaccatcgg ctacaccgga  1320
gtcggtacccc agctcttcga cagcgagacc gagctcccac tgagaccac cgagaggccc  1380
aactacgaga gctactccca ccgcctgtcg aacatccgcc tcatcatcgg caacacgctc  1440
agagctcccg tctactcctg gacgcacagg tcagctgacc ggacgaacac catcgcgacg  1500
aacatcatca cccagatccc ggccgtcaag ggcaacttcc tcttcaacgg ctccgtcatc  1560
```

```
tccggaccag gcttcaccgg aggagacctc gtccgcctca caactccgg caacaacatc    1620 tacaaccggg gctacatcga ggtgccgatc cagttcatct ccacgagcac tcggtaccgc    1680
gtcagagtgc gctacgcgag cgtcactccg atccgcctct ccgtcaactg gggcaactcg    1740
aacatcttca gcaccatcgt cccagccacc gcgactagcc tcgacaacct gcagtcccgc    1800
aacttcggct acttcgagag ccgcaacgcc ttcacgagcg cgactggcaa cgtcgtcggc    1860
gtccgcaact tctccgagaa cgccggagtg atcatcgacc gcttcgagtt catccccgtg    1920
accgcgacct tcgaggccga gtacgacctt gagagagctc aggaggcc                 1968
```

```
<210> SEQ ID NO 41
<211> LENGTH: 655
<212> TYPE: PRT
<213> ORGANISM: Artificial Sequence
<220> FEATURE:
<223> OTHER INFORMATION: Cry1B variant

<400> SEQUENCE: 41

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
                20                  25                  30

Ala Arg Ile Glu Asp Ser Leu Cys Ile Ala Glu Gly Asn Asn Ile Asn
            35                  40                  45

Pro Leu Val Ser Ala Ser Thr Val Gln Thr Gly Ile Asn Ile Ala Gly
        50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Met Ile
                100                 105                 110

Thr Leu Asn Ala Arg Asn Thr Ala Leu Ala Arg Leu Gln Gly Leu Gly
            115                 120                 125

Ala Ser Phe Arg Ala Tyr Gln Gln Ser Leu Glu Asp Trp Leu Glu Asn
        130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Ile Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
```

```
               290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Arg Trp Ser Ser Thr Gln His
                340                 345                 350

Met Asn Tyr Trp Val Gly His Arg Leu Asn Phe Arg Pro Ile Gly Gly
            355                 360                 365

Thr Leu Asn Thr Ser Thr His Gly Ala Thr Asn Thr Ser Ile Asn Pro
370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ile Gly Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
                500                 505                 510

Phe Leu Phe Asn Gly Ser Val Ile Ser Gly Pro Gly Phe Thr Gly Gly
            515                 520                 525

Asp Leu Val Arg Leu Asn Asn Ser Gly Asn Asn Ile Gln Asn Arg Gly
530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
            595                 600                 605

Asn Ala Phe Thr Ser Ala Thr Gly Asn Val Val Gly Val Arg Asn Phe
610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 42
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 42
atgccctcca accgcaagaa cgagaacgag ataatcaacg ccctgtcgat cccagccgtc        60
```

```
tccaaccact ccgcgcagat ggacctctca ctggacgctc gcatcgagga ctcactctgc    120
atcgccgagg caacaacat  caacccgctc gtcagcgcct cgaccgtgca gactggcatc    180
aacatcgccg gtcgcatact cggcgtcctc ggagtcccat cgcaggtca gctggcgagc    240 ttctacagct tcatcgtcgg cgagctctgg ccatcaggtc gcgatccctg ggagatcttc    300
atggagcacg tcgagcagct ggtcaggcag atgatcacgc tcaacgctcg caacacggct    360
ctcgccagac tccaaggcct cggagccagc ttcagagcct accagcagtc cctcgaggac    420
tggctcgaga accgcgacaa cgcgaggacc cggagcgtcc tctacaccca gtacatcgcg    480
ctggagctcg acttcctgaa cgcgatgcca ctcttcgcca tcaacaacca gcaggtgccg    540
ctcctcatgg tctacgccca agctgccaac ctccacctcc tgctcctcag agacgctagc    600
ctgttcggca gcgagttcgg actcacgtcg caggagatcc agcgctacta cgagcgccag    660
gcggagaaga cccgggagta cagcgactac tgcgcacgct ggtacaacac cggcctgaac    720
aacctgcgcg gcacgaacgc tgagagctgg ctccgctaca accagttccg cagggacctc    780
acactcggag tcctcgacct cgtcgcgctg ttcccgagct acgacacgcg gatctacccg    840
atcaacacga gcgcgcagct cactcgcgag atctacacgg accccatcgg tcgcacgaac    900
gctccatccg gcttcgcctc caccaactgg ttcaacaaca cgcgccgtc gttcagcgcc     960 atcgaagctg caatcttccg cccacctcac ctgctggact cccagagca gctcaccatc    1020 tacagcgcct ccagccgctg gtccagcacg cagcacatga actactgggt cggccaccgc    1080
ctcaacttca ggcctatcgg cggtaccctc aacacctcga cccacggcgc cacgaacacg    1140
tccatcaacc cggtgacgct ccagttcacg agccgggacg tctaccgcac tgagagctac    1200
gctggcatca acatcctgct cacgacgcca gtgaacggcg tcccgtgggc acgcttcaac    1260
tggaggaacc ctctcaactc cctgcgcgga tcgctcctct acaccatcgg ctacaccgga    1320
gtcggtaccc agctcttcga cagcgagacc gagctcccac ctgagaccac cgagaggccc    1380
aactacgaga gctactccca ccgcctgtcg aacatccgcc tcatcatcgg cggcacgctc    1440
agagctcccg tctactcctg gacgcacagg tcagctgacc ggacgaacac catcgcgacg    1500
aacatcatca cccagatccc ggccgtcaag gcaacttcc tcttcaacgg ctccgtcatc    1560
tccggaccag gcttcaccgg aggagacctc gtccgcctca caactccgg caacaacatc    1620 cagaaccggg gctacatcga ggtgccgatc cagttcatct ccacgagcac tcggtaccgc    1680
gtcagagtgc gctacgcgag cgtcactccg atccgcctct ccgtcaactg gggcaactcg    1740
aacatcttca gctccatcgt cccagccacc gcgactagcc tcgacaacct gcagtcccgc    1800
aacttcggct acttcgagag ccgcaacgcc ttcacgagcg cgactggcaa cgtcgtcggc    1860
gtccgcaact tctccgagaa cgccggagtg atcatcgacc gcttcgagtt catccccgtg    1920
accgcgacct tcgaggccga gtacgacctt gagagagctc aggaggcc                 1968
```

<210> SEQ ID NO 43
<211> LENGTH: 655
<212> TYPE: PRT
<213> ORGANISM: Artificial Sequence
<220> FEATURE:
<223> OTHER INFORMATION: Cry1B variant

<400> SEQUENCE: 43

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp

-continued

```
                20                  25                  30
Ala Arg Ile Glu Asp Ser Leu Cys Ile Ala Glu Gly Asn Asn Ile Asn
            35                  40                  45

Pro Leu Val Ser Ala Ser Thr Val Gln Thr Gly Ile Asn Ile Ala Gly
        50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Gln Leu Val Arg Gln Met Ile
            100                 105                 110

Thr Met Asn Ala Arg Asn Thr Ala Leu Ala Arg Leu Gln Gly Leu Gly
            115                 120                 125

Ala Ser Phe Arg Ala Tyr Gln Gln Ser Leu Glu Asp Trp Leu Glu Asn
            130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
            210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
            290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
            355                 360                 365

Thr Leu Asn Thr Ser Thr His Gly Ala Thr Asn Thr Ser Ile Asn Pro
            370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445
```

```
Glu Thr Glu Leu Pro Pro Glu Thr Thr Glu Arg Pro Asn Tyr Glu Ser
    450                 455                 460
Tyr Ser His Arg Leu Ser Asn Ile Arg Leu Ile Ile Gly Gly Thr Leu
465                 470                 475                 480
Arg Ala Pro Val Tyr Ser Trp Thr His Arg Ser Ala Asp Arg Thr Asn
                485                 490                 495
Thr Ile Ala Thr Asn Ile Ile Thr Gln Ile Pro Ala Val Lys Gly Asn
            500                 505                 510
Phe Leu Phe Asn Gly Ser Val Ile Ser Gly Pro Gly Phe Thr Gly Gly
        515                 520                 525
Asp Leu Val Arg Leu Asn Asn Ser Gly Asn Asn Ile Gln Asn Arg Gly
    530                 535                 540
Tyr Ile Glu Val Pro Ile Gln Phe Ile Ser Thr Ser Thr Arg Tyr Arg
545                 550                 555                 560
Val Arg Val Arg Tyr Ala Ser Val Thr Pro Ile Arg Leu Ser Val Asn
                565                 570                 575
Trp Gly Asn Ser Asn Ile Phe Ser Ser Ile Val Pro Ala Thr Ala Thr
            580                 585                 590
Ser Leu Asp Asn Leu Gln Ser Arg Asn Phe Gly Tyr Phe Glu Ser Arg
        595                 600                 605
Asn Ala Phe Thr Ser Ala Thr Gly Asn Val Val Gly Val Arg Asn Phe
    610                 615                 620
Ser Glu Asn Ala Gly Val Ile Ile Asp Arg Phe Glu Phe Ile Pro Val
625                 630                 635                 640
Thr Ala Thr Phe Glu Ala Glu Tyr Asp Leu Glu Arg Ala Gln Glu
                645                 650                 655

<210> SEQ ID NO 44
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 44
atgccctcca accgcaagaa cgagaacgag ataatcaacg ccctgtcgat cccagccgtc      60
tccaaccact ccgcgcagat ggacctctca ctggacgctc gcatcgagga ctcactctgc     120
atcgccgagg caacaacat caacccgctc gtcagcgcct cgaccgtgca gactggcatc      180
aacatcgccg tcgcatact cggcgtcctc ggagtccat cgcaggtca gctggcgagc       240 ttctacagct tcatcgtcgg cgagctctgg ccatcaggtc gcgatccctg ggagatcttc     300
atggagcacg tcgagcagct ggtcaggcag atgatcacga tgaacgctcg caacacggct     360
ctcgccagac tccaaggcct cggagccagc ttcagagcct accagcagtc cctcgaggac     420
tggctcgaga accgcgacaa cgcgaggacc cggagcgtcc tctacaccca gtacatcgcg     480
ctggagctcg acttcctgaa cgcgatgcca ctcttcgcca tcaacaacca gcaggtgccg     540
ctcctcatgg tctacgccca agctgccaac ctccacctcc tgctcctcag agacgctagc     600
ctgttcggca gcgagttcgg actcacgtcg caggagatcc agcgctacta cgagcgccag     660
gcggagaaga cccgggagta cagcgactac tgcgcacgct ggtacaacac cggcctgaac     720
aacctgcgcg gcacgaacgc tgagagctgg ctccgctaca accagttccg cagggacctc     780
acactcggag tcctcgacct cgtcgcgctg ttcccgagct acgacacgcg gatctacccg     840
atcaacacga gcgcgcagct cactcgcgag atctacacgg accccatcgg tcgcacgaac     900
```

```
gctccatccg gcttcgcctc caccaactgg ttcaacaaca acgcgccgtc gttcagcgcc    960
atcgaagctg caatcttccg cccacctcac ctgctggact ccccagagca gctcaccatc   1020
tacagcgcct ccagccgctg gtccagcacg cagcacatga actactgggt cggccaccgc   1080
ctcaacttca ggcctatcgg cggtacccctc aacacctcga cccacggcgc cacgaacacg   1140
tccatcaacc cggtgacgct ccagttcacg agccgggacg tctaccgcac tgagagctac   1200
gctggcatca acatcctgct cacgacgcca gtgaacggcg tcccgtgggc acgcttcaac   1260
tggaggaacc ctctcaactc cctgcgcgga tcgctcctct acaccatcgg ctacaccgga   1320
gtcggtaccc agctcttcga cagcgagacc gagctcccac ctgagaccac cgagaggccc   1380
aactacgaga gctactccca ccgcctgtcg aacatccgcc tcatcatcgg cggcacgctc   1440
agagctcccg tctactcctg gacgcacagg tcagctgacc ggacgaacac catcgcgacg   1500
aacatcatca cccagatccc ggccgtcaag ggcaacttcc tcttcaacgg ctccgtcatc   1560
tccggaccag gcttcaccgg aggagacctc gtccgcctca caactccgg caacaacatc   1620
cagaaccggg gctacatcga ggtgccgatc cagttcatct ccacgagcac tcggtaccgc   1680
gtcagagtgc gctacgcgag cgtcactccg atccgcctct ccgtcaactg ggcaactcg   1740
aacatcttca gctccatcgt cccagccacc gcgactagcc tcgacaacct gcagtcccgc   1800
aacttcggct acttcgagag ccgcaacgcc ttcacgagcg cgactggcaa cgtcgtcggc   1860
gtccgcaact ctccgagaa cgccggagtg atcatcgacc gcttcgagtt catccccgtg   1920
accgcgacct tcgaggccga gtacgacctt gagagagctc aggaggcc                1968
```

<210> SEQ ID NO 45
<211> LENGTH: 655
<212> TYPE: PRT
<213> ORGANISM: Artificial Sequence
<220> FEATURE:
<223> OTHER INFORMATION: coding sequence of Cry1B variant

<400> SEQUENCE: 45

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
                20                  25                  30

Ala Arg Ile Glu Asp Ser Leu Cys Ile Ala Glu Gly Asn Asn Ile Asn
            35                  40                  45

Pro Leu Val Ser Ala Ser Thr Val Gln Thr Gly Ile Asn Ile Ala Gly
        50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Met Ile
                100                 105                 110

Thr His Asn Ala Arg Asn Thr Ala Leu Ala Arg Leu Gln Gly Leu Gly
            115                 120                 125

Ala Ser Phe Arg Ala Tyr Gln Gln Ser Leu Glu Asp Trp Leu Glu Asn
        130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175
```

```
Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
            245                 250                 255

Arg Arg Asp Leu Thr Leu Gly Val Leu Asp Leu Val Ala Leu Phe Pro
        260                 265                 270

Ser Tyr Asp Thr Arg Ile Tyr Pro Ile Asn Thr Ser Ala Gln Leu Thr
    275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Ala Pro Ser Phe Ser Ala
305                 310                 315                 320

Ile Glu Ala Ala Ile Phe Arg Pro Pro His Leu Leu Asp Phe Pro Glu
            325                 330                 335

Gln Leu Thr Ile Tyr Ser Ala Ser Ser Arg Trp Ser Ser Thr Gln His
        340                 345                 350

Met Asn Tyr Trp Val Gly His Arg Leu Asn Phe Arg Pro Ile Gly Gly
    355                 360                 365

Thr Leu Asn Thr Ser Thr His Gly Ala Thr Asn Thr Ser Ile Asn Pro
            370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
            405                 410                 415

Ala Arg Phe Asn Trp Arg Asn Pro Leu Asn Ser Leu Arg Gly Ser Leu
        420                 425                 430

Leu Tyr Thr Ile Gly Tyr Thr Gly Val Gly Thr Gln Leu Phe Asp Ser
    435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ile Gly Gly Thr Leu
465                 470                 475                 480

Arg Ala Pro Val Tyr Ser Trp Thr His Arg Ser Ala Asp Arg Thr Asn
            485                 490                 495

Thr Ile Ala Thr Asn Ile Ile Thr Gln Ile Pro Ala Val Lys Gly Asn
        500                 505                 510

Phe Leu Phe Asn Gly Ser Val Ile Ser Gly Pro Gly Phe Thr Gly Gly
    515                 520                 525

Asp Leu Val Arg Leu Asn Asn Ser Gly Asn Asn Ile Gln Asn Arg Gly
            530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
            565                 570                 575

Trp Gly Asn Ser Asn Ile Phe Ser Ile Val Pro Ala Thr Ala Thr
        580                 585                 590
```

```
Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 46
<211> LENGTH: 1968
<212> TYPE: DNA
<213> ORGANISM: Artificial Sequence
<220> FEATURE:
<223> OTHER INFORMATION: Cry1B variant

<400> SEQUENCE: 46
atgccctcca accgcaagaa cgagaacgag ataatcaacg ccctgtcgat cccagccgtc     60
tccaaccact ccgcgcagat ggacctctca ctggacgctc gcatcgagga ctcactctgc    120
atcgccgagg gcaacaacat caacccgctc gtcagcgcct cgaccgtgca gactggcatc    180
aacatcgccg gtcgcatact cggcgtcctc ggagtcccat tcgcaggtca gctggcgagc    240
ttctacagct tcatcgtcgg cgagctctgg ccatcaggtc gcgatccctg ggagatcttc    300
atggagcacg tcgagcagct ggtcaggcag atgatcacgc acaacgctcg caacacggct    360
ctcgccagac tccaaggcct cggagccagc ttcagagcct accagcagtc cctcgaggac    420
tggctcgaga accgcgacaa cgcgaggacc cggagcgtcc tctacaccca gtacatcgcg    480
ctggagctcg acttcctgaa cgcgatgcca ctcttcgcca tcaacaacca gcaggtgccg    540
ctcctcatgg tctacgccca agctgccaac ctccacctcc tgctcctcag agacgctagc    600
ctgttcggca gcgagttcgg actcacgtcg caggagatcc agcgctacta cgagcgccag    660
gcggagaaga cccgggagta cagcgactac tgcgcacgct ggtacaacac cggcctgaac    720
aacctgcgcg gcacgaacgc tgagagctgg ctccgctaca accagttccg cagggacctc    780
acactcggag tcctcgacct cgtcgcgctg ttcccgagct acgacacgcg gatctacccg    840
atcaacacga gcgcgcagct cactcgcgag atctacacgg accccatcgg tcgcacgaac    900
gctccatccg gcttcgcctc caccaactgg ttcaacaaca acgcgccgtc gttcagcgcc    960
atcgaagctg caatcttccg cccacctcac ctgctggact tcccagagca gctcaccatc   1020
tacagcgcct ccagccgctg gtccagcacg cagcacatga actactgggt cggccaccgc   1080
ctcaacttca ggcctatcgg cggtaccctc aacacctcga cccacggcgc cacgaacacg   1140
tccatcaacc cggtgacgct ccagttcacg agccgggacg tctaccgcac tgagagctac   1200
gctggcatca acatcctgct cacgacgcca gtgaacggcg tcccgtgggc acgcttcaac   1260
tggaggaacc ctctcaactc cctgcgcgga tcgctcctct acaccatcgg ctacaccgga   1320
gtcggtaccc agctcttcga cagcgagacc gagctcccac ctgagaccac cgagaggccc   1380
aactacgaga gctactccca ccgcctgtcg aacatccgcc tcatcatcgg cggcacgctc   1440
agagctcccg tctactcctg gacgcacagg tcagctgacc ggacgaacac catcgcgacg   1500
aacatcatca cccagatccc ggccgtcaag ggcaacttcc tcttcaacgg ctccgtcatc   1560
tccggaccag gcttcaccgg aggagacctc gtccgcctca acaactccgg caacaacatc   1620
cagaaccggg gctacatcga ggtgccgatc cagttcatct ccacgagcac tcggtaccgc   1680
gtcagagtgc gctacgcgag cgtcactccg atccgcctct ccgtcaactg ggcaactcg    1740
```

-continued

```
aacatcttca gctccatcgt cccagccacc gcgactagcc tcgacaacct gcagtcccgc   1800
aacttcggct acttcgagag ccgcaacgcc ttcacgagcg cgactggcaa cgtcgtcggc   1860
gtccgcaact tctccgagaa cgccggagtg atcatcgacc gcttcgagtt catccccgtg   1920
accgcgacct tcgaggccga gtacgacctt gagagagctc aggaggcc                1968
```

<210> SEQ ID NO 47
<211> LENGTH: 655
<212> TYPE: PRT
<213> ORGANISM: Artificial Sequence
<220> FEATURE:
<223> OTHER INFORMATION: Cry1B variant

<400> SEQUENCE: 47

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
                20                  25                  30

Ala Arg Ile Glu Asp Ser Leu Cys Ile Ala Glu Gly Asn Asn Ile Asn
            35                  40                  45

Pro Leu Val Ser Ala Ser Thr Val Gln Thr Gly Ile Asn Ile Ala Gly
        50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln His Ile
                100                 105                 110

Thr Met Asn Ala Arg Asn Thr Ala Leu Ala Arg Leu Gln Gly Leu Gly
            115                 120                 125

Ala Ser Phe Arg Ala Tyr Gln Gln Ser Leu Glu Asp Trp Leu Glu Asn
        130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320
```

-continued

Ile Glu Ala Ala Ile Phe Arg Pro Pro His Leu Leu Asp Phe Pro Glu
            325                 330                 335

Gln Leu Thr Ile Tyr Ser Ala Ser Ser Arg Trp Ser Ser Thr Gln His
        340                 345                 350

Met Asn Tyr Trp Val Gly His Arg Leu Asn Phe Arg Pro Ile Gly Gly
    355                 360                 365

Thr Leu Asn Thr Ser Thr His Gly Ala Thr Asn Thr Ser Ile Asn Pro
370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 48
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 48
atgccctcca accgcaagaa cgagaacgag ataatcaacg ccctgtcgat cccagccgtc        60
tccaaccact ccgcgcagat ggacctctca ctggacgctc gcatcgagga ctcactctgc       120
atcgccgagg gcaacaacat caacccgctc gtcagcgcct cgaccgtgca gactggcatc       180

| | |
|---|---|
| aacatcgccg gtcgcatact cggcgtcctc ggagtcccat tcgcaggtca gctggcgagc | 240 |
| ttctacagct tcatcgtcgg cgagctctgg ccatcaggtc gcgatccctg ggagatcttc | 300 |
| atggagcacg tcgagcagct ggtcaggcag cacatcacga tgaacgctcg caacacggct | 360 |
| ctcgccagac tccaaggcct cggagccagc ttcagagcct accagcagtc cctcgaggac | 420 |
| tggctcgaga accgcgacaa cgcgaggacc cggagcgtcc tctacaccca gtacatcgcg | 480 |
| ctggagctcg acttcctgaa cgcgatgcca ctcttcgcca tcaacaacca gcaggtgccg | 540 |
| ctcctcatgg tctacgccca agctgccaac ctccacctcc tgctcctcag agacgctagc | 600 |
| ctgttcggca gcgagttcgg actcacgtcg caggagatcc agcgctacta cgagcgccag | 660 |
| gcggagaaga cccgggagta cagcgactac tgcgcacgct ggtacaacac cggcctgaac | 720 |
| aacctgcgcg gcacgaacgc tgagagctgg ctccgctaca accagttccg cagggacctc | 780 |
| acactcggag tcctcgacct cgtcgcgctg ttcccgagct acgacacgcg gatctacccg | 840 |
| atcaacacga gcgcgcagct cactcgcgag atctacacgg accccatcgg tcgcacgaac | 900 |
| gctccatccg gcttcgcctc caccaactgg ttcaacaaca cgcgccgtc gttcagcgcc | 960 |
| atcgaagctg caatcttccg cccacctcac ctgctggact cccagagca gctcaccatc | 1020 |
| tacagcgcct ccagccgctg gtccagcacg cagcacatga actactgggt cggccaccgc | 1080 |
| ctcaacttca ggcctatcgg cggtaccctc aacacctcga cccacggcgc cacgaacacg | 1140 |
| tccatcaacc cggtgacgct ccagttcacg agccgggacg tctaccgcac tgagagctac | 1200 |
| gctggcatca acatcctgct cacgacgcca gtgaacggcg tcccgtgggc acgcttcaac | 1260 |
| tggaggaacc ctctcaactc cctgcgcgga tcgctcctct acaccatcgg ctacaccgga | 1320 |
| gtcggtaccc agctcttcga cagcgagacc gagctcccac ctgagaccac cgagaggccc | 1380 |
| aactacgaga gctactccca ccgcctgtcg aacatccgcc tcatcatcgg cggcacgctc | 1440 |
| agagctcccg tctactcctg gacgcacagg tcagctgacc ggacgaacac catcgcgacg | 1500 |
| aacatcatca cccagatccc ggccgtcaag ggcaacttcc tcttcaacgg ctccgtcatc | 1560 |
| tccggaccag gcttcaccgg aggagacctc gtccgcctca caactccgg caacaacatc | 1620 |
| cagaaccggg gctacatcga ggtgccgatc cagttcatct ccacgagcac tcggtaccgc | 1680 |
| gtcagagtgc gctacgcgag cgtcactccg atccgcctct ccgtcaactg gggcaactcg | 1740 |
| aacatcttca gctccatcgt cccagccacc gcgactagcc tcgacaacct gcagtcccgc | 1800 |
| aacttcggct acttcgagag ccgcaacgcc ttcacgagcg cgactggcaa cgtcgtcggc | 1860 |
| gtccgcaact tctccgagaa cgccggagtg atcatcgacc gcttcgagtt catccccgtg | 1920 |
| accgcgacct tcgaggccga gtacgacctt gagagagctc aggaggcc | 1968 |

<210> SEQ ID NO 49
<211> LENGTH: 655
<212> TYPE: PRT
<213> ORGANISM: Artificial Sequence
<220> FEATURE:
<223> OTHER INFORMATION: Cry1B variant

<400> SEQUENCE: 49

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Le

```
Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Met Ile
                    100                 105                 110

Thr His Asn Ala Arg Asn Thr Ala Leu Ala Arg Leu Gln Gly Leu Gly
                115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Ile Tyr Pro Ile Asn Thr Ser Ala Gln Leu Thr
    275                 280                 285

Arg Glu Ile Tyr Thr Asp Pro Ile Gly Arg Thr Asn Ala Pro Ser Gly
290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Arg Trp Ser Ser Thr Gln His
                340                 345                 350

Met Asn Tyr Trp Val Gly His Arg Leu Asn Phe Arg Pro Ile Asn Gly
    355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
```

```
          465                 470                 475                 480
Arg Ala Pro Val Tyr Ser Trp Thr His Arg Ser Ala Asp Arg Thr Asn
                    485                 490                 495
Thr Ile Ala Thr Asn Ile Ile Thr Gln Ile Pro Ala Val Lys Gly Asn
                500                 505                 510
Phe Leu Phe Asn Gly Ser Val Ile Ser Gly Pro Gly Phe Thr Gly Gly
            515                 520                 525
Asp Leu Val Arg Leu Asn Asn Ser Gly Asn Asn Ile Gln Asn Arg Gly
        530                 535                 540
Tyr Ile Glu Val Pro Ile Gln Phe Ile Ser Thr Ser Thr Arg Tyr Arg
545                 550                 555                 560
Val Arg Val Arg Tyr Ala Ser Val Thr Pro Ile Arg Leu Ser Val Asn
                565                 570                 575
Trp Gly Asn Ser Asn Ile Phe Ser Ser Ile Val Pro Ala Thr Ala Thr
                580                 585                 590
Ser Leu Asp Asn Leu Gln Ser Arg Asn Phe Gly Tyr Phe Glu Ser Arg
            595                 600                 605
Asn Ala Phe Thr Ser Ala Thr Gly Asn Val Val Gly Val Arg Asn Phe
        610                 615                 620
Ser Glu Asn Ala Gly Val Ile Ile Asp Arg Phe Glu Phe Ile Pro Val
625                 630                 635                 640
Thr Ala Thr Phe Glu Ala Glu Tyr Asp Leu Glu Arg Ala Gln Glu
                645                 650                 655
```

<210> SEQ ID NO 50
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 50

```
atgccctcca accgcaagaa cgagaacgag ataatcaacg ccctgtcgat cccagccgtc     60
tccaaccact ccgcgcagat ggacctctca ctggacgctc gcatcgagga ctcactctgc    120
atcgccgagg caacaacat caacccgctc gtcagcgcc cgaccgtgca gactggcatc     180
aacatcgccg tcgcatact cggcgtcctc ggagtcccat cgcaggtca gctggcgagc     240
ttctacagct tcatcgtcgg cgagctctgg ccatcaggtc gcgatccctg ggagatcttc    300
atggagcacg tcgagcagct ggtcaggcag atgatcacgc acaacgctcg caacacggct    360
ctcgccagac tccaaggcct cggagccagc ttcagagcct accagcagtc cctcgaggac    420
tggctcgaga accgcgacaa cgcgaggacc cggagcgtcc tctacaccca gtacatcgcg    480
ctggagctcg acttcctgaa cgcgatgcca ctcttcgcca tcaacaacca gcaggtgccg    540
ctcctcatgg tctacgccca agctgccaac ctccacctcc tgctcctcag agacgctagc    600
ctgttcggca gcgagttcgg actcacgtcg caggagatcc agcgctacta cgagcgccag    660
gcggagaaga cccgggagta cagcgactac tgcgcacgct ggtacaacac cggcctgaac    720
aacctgcgcg gcacgaacgc tgagagctgg ctccgctaca accagttccg cagggacctc    780
acactcggag tcctcgacct cgtcgcgctg ttccgagct acgacacgcg gatctacccg    840
atcaacacga gcgcgcagct cactcgcgag atctacacgg accccatcgg tcgcacgaac    900
gctccatccg gcttcgcctc caccaactgg ttcaacaaca acgcgccgtc gttcagcgcc    960
atcgaagctg caatcttccg cccacctcac ctgctggact cccagagca gctcaccatc   1020
```

-continued

```
tacagcgcct ccagccgctg gtccagcacg cagcacatga actactgggt cggccaccgc   1080
ctcaacttca ggcctatcaa cggtaccctc aacacctcga cccacggcgc cacgaacacg   1140
tccatcaacc cggtgacgct ccagttcacg agccgggacg tctaccgcac tgagagctac   1200
gctggcatca acatcctgct cacgacgcca gtgaacggcg tcccgtgggc acgcttcaac   1260
tggaggaacc ctctcaactc cctgcgcgga tcgctcctct acaccatcgg ctacaccgga   1320
gtcggtaccc agtcttcga cagcgagacc gagctccac ctgagaccac cgagaggccc   1380
aactacgaga gctactccca ccgcctgtcg aacatccgcc tcatcatcgg caacacgctc   1440
agagctcccg tctactcctg gacgcacagg tcagctgacc ggacgaacac catcgcgacg   1500
aacatcatca cccagatccc ggccgtcaag ggcaacttcc tcttcaacgg ctccgtcatc   1560
tccggaccag gcttcaccgg aggagacctc gtccgcctca caactccgg caacaacatc   1620 cagaaccggg gctacatcga ggtgccgatc cagttcatct ccacgagcac tcggtaccgc   1680
gtcagagtgc gctacgcgag cgtcactccg atccgcctct ccgtcaactg gggcaactcg   1740
aacatcttca gctccatcgt cccagccacc gcgactagcc tcgacaacct gcagtcccgc   1800
aacttcggct acttcgagag ccgcaacgcc ttcacgagcg cgactggcaa cgtcgtcggc   1860
gtccgcaact tctccgagaa cgccggagtg atcatcgacc gcttcgagtt catccccgtg   1920
accgcgacct tcgaggccga gtacgacctt gagagagctc aggaggcc                1968
```

<210> SEQ ID NO 51
<211> LENGTH: 655
<212> TYPE: PRT
<213> ORGANISM: Artificial Sequence
<220> FEATURE:
<223> OTHER INFORMATION: Cry1B variant

<400> SEQUENCE: 51

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20

```
                195                 200                 205
Thr Ser Gln Glu Ile Gln Arg Tyr Tyr Glu Arg Gln Ala Glu Lys Thr
210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
            290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
                340                 345                 350

Met Asn Tyr Trp Val Gly His Arg Leu Asn Phe Arg Pro Ile Asn Gly
            355                 360                 365

Thr Leu Asn Thr Ser Thr His Gly Ala Thr Asn Thr Ser Ile Asn Pro
370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
                500                 505                 510

Phe Leu Phe Asn Gly Ser Val Ile Ser Gly Pro Gly Phe Thr Gly Gly
            515                 520                 525

Asp Leu Val Arg Leu Asn Asn Ser Gly Asn Asn Ile Gln Asn Arg Gly
            530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
            595                 600                 605

Asn Ala Phe Thr Ser Ala Thr Gly Asn Val Val Gly Val Arg Asn Phe
610                 615                 620
```

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
            645                 650                 655

<210> SEQ ID NO 52
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 52

| | | | | | |
|---|---|---|---|---|---|
| atgccctcca | accgcaagaa | cgagaacgag | ataatcaacg | ccctgtcgat | cccagccgtc | 60 |
| tccaaccact | ccgcgcagat | ggacctctca | ctggacgctc | gcatcgagga | ctcactctgc | 120 |
| atcgccgagg | gcaacaacat | caacccgctc | gtcagcgcct | cgaccgtgca | gactggcatc | 180 |
| aacatcgccg | tcgcatact | cggcgtcctc | ggagtcccat | cgcaggtca | gctggcgagc | 240 |
| ttctacagct | tcatcgtcgg | cgagctctgg | ccatcaggtc | gcgatccctg | ggagatcttc | 300 |
| atggagcacg | tcgagcagct | ggtcaggcag | cacatcacga | tgaacgctcg | caacacggct | 360 |
| ctcgccagac | tccaaggcct | cggagccagc | ttcagagcct | accagcagtc | cctcgaggac | 420 |
| tggctcgaga | accgcgacaa | cgcgaggacc | cggagcgtcc | tctacaccca | gtacatcgcg | 480 |
| ctggagctcg | acttcctgaa | cgcgatgcca | ctcttcgcca | tcaacaacca | gcaggtgccg | 540 |
| ctcctcatgg | tctacgccca | agctgccaac | ctccacctcc | tgctcctcag | agacgctagc | 600 |
| ctgttcggca | gcgagttcgg | actcacgtcg | caggagatcc | agcgctacta | cgagcgccag | 660 |
| gcggagaaga | cccgggagta | cagcgactac | tgcgcacgct | ggtacaacac | cggcctgaac | 720 |
| aacctgcgcg | gcacgaacgc | tgagagctgg | ctccgctaca | accagttccg | cagggacctc | 780 |
| acactcggag | tcctcgacct | cgtcgcgctg | ttcccgagct | acgacacgcg | gatctacccg | 840 |
| atcaacacga | gcgcgcagct | cactcgcgag | atctacacgg | accccatcgg | tcgcacgaac | 900 |
| gctccatccg | gcttcgcctc | caccaactgg | ttcaacaaca | acgcgccgtc | gttcagcgcc | 960 |
| atcgaagctg | caatcttccg | cccacctcac | ctgctggact | tccagagca | gctcaccatc | 1020 |
| tacagcgcct | ccagccgctg | gtccagcacg | cagcacatga | actactgggt | cggccaccgc | 1080 |
| ctcaacttca | ggcctatcaa | cggtaccctc | aacacctcga | cccacggcgc | cacgaacacg | 1140 |
| tccatcaacc | cggtgacgct | ccagttcacg | agccgggacg | tctaccgcac | tgagagctac | 1200 |
| gctggcatca | acatcctgct | cacgacgcca | gtgaacggcg | tcccgtgggc | acgcttcaac | 1260 |
| tggaggaacc | ctctcaactc | cctgcgcgga | tcgctcctct | acaccatcgg | ctacaccgga | 1320 |
| gtcggtaccc | agctcttcga | cagcgagacc | gagctccac | ctgagaccac | cgagaggccc | 1380 |
| aactacgaga | gctactccca | ccgcctgtcg | aacatccgcc | tcatcatcgg | caacacgctc | 1440 |
| agagctcccg | tctactcctg | gacgcacagg | tcagctgacc | ggacgaacac | catcgcgacg | 1500 |
| aacatcatca | cccagatccc | ggccgtcaag | gcaacttcc | tcttcaacgg | ctccgtcatc | 1560 |
| tccggaccag | gcttcaccgg | aggagacctc | gtccgcctca | caactccgg | caacaacatc | 1620 |
| cagaaccggg | gctacatcga | ggtgccgatc | cagttcatct | ccacgagcac | tcggtaccgc | 1680 |
| gtcagagtgc | gctacgcgag | cgtcactccg | atccgcctct | ccgtcaactg | ggcaactcg | 1740 |
| aacatcttca | gctccatcgt | cccagccacc | gcgactagcc | tcgacaacct | gcagtcccgc | 1800 |
| aacttcggct | acttcgagag | ccgcaacgcc | ttcacgagcg | cgactggcaa | cgtcgtcggc | 1860 |

```
gtccgcaact tctccgagaa cgccggagtg atcatcgacc gcttcgagtt catccccgtg    1920
accgcgacct tcgaggccga gtacgacctt gagagagctc aggaggcc                 1968
```

<210> SEQ ID NO 53
<211> LENGTH: 655
<212> TYPE: PRT
<213> ORGANISM: Bacillus thuringiensis

<400> SEQUENCE: 53

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Pro Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Leu Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
```

```
            355                 360                 365
Ser Leu Ser Thr Ser Thr His Gly Asn Thr Asn Thr Ser Ile Asn Pro
        370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
530                 535                 540

Tyr Leu Glu Val Pro Ile Gln Phe Ile Ser Thr Ser Thr Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asp Phe Gly Tyr Phe Glu Ser Thr
        595                 600                 605

Asn Ala Phe Thr Ser Ala Thr Gly Asn Val Val Gly Val Arg Asn Phe
610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655

<210> SEQ ID NO 54
<211> LENGTH: 1965
<212> TYPE: DNA
<213> ORGANISM: Bacillus thuringiensis

<400> SEQUENCE: 54
atgccttcaa ataggaaaaa tgagaatgaa attataaatg ctttatcgat tccagctgta     60
tcgaatcatt ccgcacaaat ggatctatca ccagatgctc gtattgagga ttctttgtgt    120
atagccgagg ggaataatat caatccactt gttagcgcat caacagtcca aacgggtatt    180
aacattgctg gtagaatact aggcgtatta ggcgtaccgt ttgctggaca actagctagt    240
ttttatagtt ttattgtcgg tgaattatgg cctagcggca gagatccgtg ggaaatcttt    300
ctagaacatg ttgaacaact tgtaagacaa caaataacag aaaatgctag gaatacggca    360
cttgctcgat tacaaggttt aggagcttcc tttagagcct atcaacaatc acttgaagac    420
tggctagaaa accgtgatga tgcaagaacg agaagtgttc tttataccca atatatagcc    480
```

```
ttagagcttg attttcttaa tgcgatgccg cttttcgcaa taaacaatca acaggttcca      540
ttattgatgg tatatgctca agctgcaaat ttacatctat tattattgag agatgcctct      600 cttttggta gtgaatttgg gcttacatcg caggaaattc aacgttatta tgagcgccaa       660
gcggaaaaaa cgagagaata ttctgattat tgcgcaagat ggtataatac gggtttaaat      720
aatttgagag ggacaaatgc tgaaagttgg ttgcgatata atcaattccg tagagactta     780
acgctaggag tattagatct agtggcacta ttcccaagct atgacacgcg tatttatcca      840
ataaatacca gtgctcaatt aacaagagaa atttatacag atccaattgg gagaacaaat     900
gcaccttcag gatttgcaag tacgaattgg tttaataata atgcaccatc gttttctgcc     960
atagaggctg ccgttattag gcctccgcat ctacttgatt ttccagaaca gcttacaatt    1020
ttcagcgtat taagtcgatg gagtaatact caatatatga attactgggt gggacataga    1080
cttgaatcgc gaacaataag ggggtcatta agtacctcga cacacggaaa taccaatact    1140
tctattaatc ctgtaacatt acagttcaca tctcgtgacg tttatagaac agaatcatat    1200
gcagggataa atatacttct aactactcct gtgaatggag taccttgggc tagatttaat    1260
tggagaaatc ccctgaattc tcttagaggt agccttctct atactatagg gtatactgga    1320
gtggggacac aactatttga ttcagaaact gaattaccac cagaaacaac agaacgacca    1380
aattatgaat cttacagtca tagattatct aatataagac taatatcagg aaacactttg    1440
agagcaccag tatattcttg gacgcaccgt agtgcagatc gtacgaatac gattgctaca    1500
aatattatta ctcaaattcc tgcagtgaag ggaaactttc tttttaatgg ttctgtaatt    1560
tcaggaccag gatttactgg tgggggactta gttagattaa ataatagtgg aaataatatt    1620
caaaatagag gctaccttga ggttccgatt caattcatct ccacatctac cagatatcga    1680
gttcgtgtac gttatgcttc tgtaaccccg attcaactca gtgttaattg gggtaattca    1740
aacatttttt ccagcatagt accagctaca gctacgtcat tagataatct acaatcaagg    1800
gattttggtt attttgaaag taccaatgca tttacatctg caacaggtaa tgtagtaggt    1860
gttagaaatt ttagtgagaa tgcaggagtg ataatagaca gatttgaatt tatcccagtt    1920
actgcaacct tcgaagcaga aatgattta gaaagagcgc aagag                     1965
```

<210> SEQ ID NO 55
<211> LENGTH: 650
<212> TYPE: PRT
<213> ORGANISM: Bacillus thuringiensis

<400> SEQUENCE: 55

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Pro Asp
                20                  25                  30

Ala Arg Ile Glu Asp Ser Leu Cys Val Ala Glu Gly Asn Asn Ile Asp
            35                  40                  45

Pro Phe Val Ser Ala Ser Thr Val Gln Thr Gly Ile Ser Ile Ala Gly
        50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Met Glu His Val Glu Gln Ile Val Arg Gln Gln Ile
                100                 105                 110
```

```
Thr Asp Ser Val Arg Asp Thr Ala Ile Ala Arg Leu Glu Gly Leu Gly
            115                 120                 125

Arg Gly Tyr Arg Ser Tyr Gln Gln Ala Leu Glu Thr Trp Leu Asp Asn
        130                 135                 140

Arg Asn Asp Ala Arg Ser Arg Ser Ile Ile Arg Glu Arg Tyr Ile Ala
145                 150                 155                 160

Leu Glu Leu Asp Ile Thr Thr Ala Ile Pro Leu Phe Ser Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ser Ser Ala Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Arg Leu Arg Gly Thr Thr Ala Glu Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Pro Thr Thr Ala Gln Leu Thr
        275                 280                 285

Arg Glu Val Tyr Thr Asp Pro Asn Gly Val Val Ala Gly Pro Asn Asn
    290                 295                 300

Ser Trp Phe Arg Asn Gly Ala Ser Phe Ser Ala Ile Glu Asn Ala Ile
305                 310                 315                 320

Ile Arg Gln Pro His Leu Tyr Asp Phe Leu Thr Asn Leu Thr Ile Tyr
                325                 330                 335

Thr Arg Arg Ser Gln Val Gly Thr Thr Ile Met Asn Leu Trp Ala Gly
            340                 345                 350

His Arg Ile Thr Phe Asn Arg Ile Gln Gly Gly Ser Thr Ser Glu Met
        355                 360                 365

Val Tyr Gly Ala Ile Thr Asn Pro Val Ser Val Ser Asp Ile Pro Phe
    370                 375                 380

Val Asn Arg Asp Val Tyr Arg Thr Val Ser Leu Ala Gly Gly Leu Gly
385                 390                 395                 400

Ser Leu Ser Gly Ile Arg Tyr Gly Leu Thr Arg Val Asp Phe Asp Met
                405                 410                 415

Ile Phe Arg Asn His Pro Asp Ile Val Thr Gly Leu Phe Tyr His Pro
            420                 425                 430

Gly His Ala Gly Ile Ala Thr Gln Val Lys Asp Ser Glu Thr Glu Leu
        435                 440                 445

Pro Pro Glu Thr Thr Glu Gln Pro Asn Tyr Arg Ala Phe Ser His Leu
    450                 455                 460

Leu Ser His Ile Ser Met Gly Pro Thr Thr Gln Asp Val Pro Pro Val
465                 470                 475                 480

Tyr Ser Trp Thr His Gln Ser Ala Asp Arg Thr Asn Thr Ile Asn Ser
                485                 490                 495

Asp Arg Ile Thr Gln Ile Pro Leu Val Lys Ala His Thr Leu Gln Ser
            500                 505                 510

Gly Thr Thr Val Val Lys Gly Pro Gly Phe Thr Gly Gly Asp Ile Leu
        515                 520                 525
```

```
Arg Arg Thr Ser Gly Gly Pro Phe Ala Phe Ser Asn Val Asn Leu Asp
    530                 535                 540

Phe Asn Leu Ser Gln Arg Tyr Arg Ala Arg Ile Arg Tyr Ala Ser Thr
545                 550                 555                 560

Thr Asn Leu Arg Ile Tyr Val Thr Val Ala Gly Glu Arg Ile Phe Ala
                565                 570                 575

Gly Gln Phe Asp Lys Thr Met Asp Ala Gly Ala Pro Leu Thr Phe Gln
            580                 585                 590

Ser Phe Ser Tyr Ala Thr Ile Asn Thr Ala Phe Thr Phe Pro Glu Arg
        595                 600                 605

Ser Ser Ser Leu Thr Val Gly Ala Asp Thr Phe Ser Ser Gly Asn Glu
610                 615                 620

Val Tyr Val Asp Arg Phe Glu Leu Ile Pro Val Thr Ala Thr Phe Glu
625                 630                 635                 640

Ala Glu Ser Asp Leu Glu Arg Ala Arg Lys
                645                 650

<210> SEQ ID NO 56
<211> LENGTH: 1950
<212> TYPE: DNA
<213> ORGANISM: Bacillus thuringiensis

<400> SEQUENCE: 56
atgccttcaa ataggaaaaa tgagaatgaa attataaatg ctttatcgat tccagctgta      60
tcgaatcatt ccgcacaaat ggatctatca ccagatgctc gcattgagga tagcttgtgt     120
gtagccgagg ggaacaatat tgatccattt gttagcgcat caacagtcca aacaggtatt     180
agtatagctg gtagaatatt aggcgtatta ggggtgccgt ttgccggaca actagctagt     240 tttatagtt tcttgttgg ggaattatgg cctagcggca gagatccatg gaaattttt       300 atggaacatg tcgaacaaat tgtaagacaa caaataacgg acagtgttag ggataccgct     360
attgctcgtt tagaaggtct aggaagaggg tatagatctt accagcaggc tcttgaaact     420
tggttagata ccgaaatga tgcaagatca agaagcatta ttcgtgagag atatattgct     480
ttagaacttg acattactac tgctataccg cttttcagca tacgaaatca agaggttcca     540
ttattaatgg tatatgctca agctgcaaat ttacacctat tattattgag agacgcatcc     600 cttttttggta gtgaatgggg gatgtcatct gccgatgtta accaatatta ccaagaacaa     660
atcagatata cagaggaata ttctaaccat tgcgtacaat ggtataatac agggctaaat     720
agattaagag ggacaactgc cgaaagttgg gtacggtata tcaattccg tagagaccta     780 acattaggtg tattagattt agtggcacta ttcccaagct atgacactcg gacttatccc     840
attccaacta ccgcccaact tacaagagaa gtgtatacag atccaaacgg tgttgtagca     900
ggacccaata tagttggtt tagaaatgga gcttcgtttt ccgctataga aaacgcaatt     960
attcgacaac ctcacctata tgatttctcta acgaacctta caatttacac gagaagaagt    1020
caagtaggca ctacaattat gaatttgtgg gcagggcata gaatcacgtt taatagaata    1080
caaggtggtt ctactagtga aatggtgtat ggggctatta ctaacccagt tagtgttagt    1140
gacataccat ttgtcaatcg ggatgtttac cgaactgtat cattagctgg tgggcttggc    1200
tctctgagtg gaatacgtta tggtttaact agagttgatt ttgatatgat atttcgtaac    1260
catcctgata tagtaactgg attatttat catccgggac acgcgggcat tgcaacccaa    1320
gtaaaagatt cagaaacaga attaccacct gaaacgacaa acagccaaa ttatagagca    1380 tttagtcatc tactaagtca tatttcaatg ggtccaacga ctcaagacgt acctccagta    1440
```

-continued

```
tattcttgga cacaccagag tgcagatcgt acgaatacaa tcaattcgga taggataaca     1500
caaataccat tggtaaaggc gcataccctc caatcgggta ccactgtagt aaaagggcca     1560
gggtttacag gagggatat cctccgtcga acaagtggag gaccatttgc ttttagtaat      1620
gttaatctag attttaactt gtcacaaagg tatcgtgcta gaattcgtta tgcctctact     1680
actaacctaa gaatttacgt aacggttgca ggtgaacgaa ttttgctgg tcaatttgac      1740 aaaactatgg atgctggtgc cccattaaca ttccaatctt ttagttacgc aactattaat    1800
acagctttta cattcccaga agatcgagc agcttgactg taggtgccga tacgtttagt      1860
tcaggtaatg aagtttatgt agatagattt gaattaatcc cagttactgc aaccttcgag    1920
gcagaatctg atttagaaag agcgcggaag                                      1950
```

<210> SEQ ID NO 57
<211> LENGTH: 830
<212> TYPE: PRT
<213> ORGANISM: Bacillus thuringiensis

<400> SEQUENCE: 57

```
Met Asn Leu Ser Pro Asp Ala Arg Ile Glu Asp Ser Leu Cys Val Ala
1               5                   10                  15

Glu Val Asn Asn Ile Asp Pro Phe Val Ser Ala Ser Thr Val Gln Thr
            20                  25                  30

Gly Ile Asn Ile Ala Gly Arg Ile Leu Gly Val Leu Gly Val Pro Phe
        35                  40                  45

Ala Gly Gln Leu Ala Ser Phe Tyr Ser Phe Leu Val Gly Glu Leu Trp
    50                  55                  60

Pro Ser Gly Arg Asp Pro Trp Glu Ile Phe Leu Glu His Val Glu Gln
65                  70                  75                  80

Leu Ile Arg Gln Gln Val Thr Glu Asn Thr Arg Asn Thr Ala Ile Ala
                85                  90                  95

Arg Leu Glu Gly Leu Gly Arg Gly Tyr Arg Ser Tyr Gln Gln Ala Leu
            100                 105                 110

Glu Thr Trp Leu Asp Asn Arg Asn Asp Ala Arg Ser Arg Ser Ile Ile
        115                 120                 125

Leu Glu Arg Tyr Val Ala Leu Glu Leu Asp Ile Thr Thr Ala Ile Pro
    130                 135                 140

Leu Phe Arg Ile Arg Asn Glu Glu Val Pro Leu Leu Met Val Tyr Ala
145                 150                 155                 160

Gln Ala Ala Asn Leu His Leu Leu Leu Arg Asp Ala Ser Leu Phe
                165                 170                 175

Gly Ser Glu Trp Gly Met Ala Ser Ser Asp Val Asn Gln Tyr Tyr Gln
            180                 185                 190

Glu Gln Ile Arg Tyr Thr Glu Glu Tyr Ser Asn His Cys Val Gln Trp
        195                 200                 205

Tyr Asn Thr Gly Leu Asn Asn Leu Arg Gly Thr Asn Ala Glu Ser Trp
    210                 215                 220

Leu Arg Tyr Asn Gln Phe Arg Arg Asp Leu Thr Leu Gly Val Leu Asp
225                 230                 235                 240

Leu Val Ala Leu Phe Pro Ser Tyr Asp Thr Arg Thr Tyr Pro Ile Asn
                245                 250                 255

Thr Ser Ala Gln Leu Thr Arg Glu Ile Tyr Thr Asp Pro Ile Gly Arg
            260                 265                 270

Thr Asn Ala Pro Ser Gly Phe Ala Ser Thr Asn Trp Phe Asn Asn Asn
```

-continued

```
            275                 280                 285
Ala Pro Ser Phe Ser Ala Ile Glu Ala Ala Ile Phe Arg Pro Pro His
    290                 295                 300
Leu Leu Asp Phe Pro Glu Gln Leu Thr Ile Tyr Ser Ala Ser Ser Arg
305                 310                 315                 320
Trp Ser Ser Thr Gln His Met Asn Tyr Trp Val Gly His Arg Leu Asn
                    325                 330                 335
Phe Arg Pro Ile Gly Gly Thr Leu Asn Thr Ser Thr Gln Gly Leu Thr
                340                 345                 350
Asn Asn Thr Ser Ile Asn Pro Val Thr Leu Gln Phe Thr Ser Arg Asp
                355                 360                 365
Val Tyr Arg Thr Glu Ser Asn Ala Gly Thr Asn Ile Leu Phe Thr Thr
370                 375                 380
Pro Val Asn Gly Val Pro Trp Ala Arg Phe Asn Phe Ile Asn Pro Gln
385                 390                 395                 400
Asn Ile Tyr Glu Arg Gly Ala Thr Thr Tyr Ser Gln Pro Tyr Gln Gly
                405                 410                 415
Val Gly Ile Gln Leu Phe Asp Ser Glu Thr Glu Leu Pro Pro Glu Thr
                420                 425                 430
Thr Glu Arg Pro Asn Tyr Glu Ser Tyr Ser His Arg Leu Ser His Ile
                435                 440                 445
Gly Leu Ile Ile Gly Asn Thr Leu Arg Ala Pro Val Tyr Ser Trp Thr
450                 455                 460
His Arg Ser Ala Asp Arg Thr Asn Thr Ile Gly Pro Asn Arg Ile Thr
465                 470                 475                 480
Gln Ile Pro Met Val Lys Ala Ser Glu Leu Pro Gln Gly Thr Thr Val
                485                 490                 495
Val Arg Gly Pro Gly Phe Thr Gly Gly Asp Ile Leu Arg Arg Thr Asn
                500                 505                 510
Thr Gly Gly Phe Gly Pro Ile Arg Val Thr Val Asn Gly Pro Leu Thr
                515                 520                 525
Gln Arg Tyr Arg Ile Gly Phe Arg Tyr Ala Ser Thr Val Asp Phe Asp
530                 535                 540
Phe Phe Val Ser Arg Gly Gly Thr Thr Val Asn Asn Phe Arg Phe Leu
545                 550                 555                 560
Arg Thr Met Asn Ser Gly Asp Glu Leu Lys Tyr Gly Asn Phe Val Arg
                565                 570                 575
Arg Ala Phe Thr Thr Pro Phe Thr Phe Thr Gln Ile Gln Asp Ile Ile
                580                 585                 590
Arg Thr Ser Ile Gln Gly Leu Ser Gly Asn Gly Glu Val Tyr Ile Asp
                595                 600                 605
Lys Ile Glu Ile Ile Pro Val Thr Ala Thr Phe Glu Ala Glu Tyr Asp
                610                 615                 620
Leu Glu Arg Ala Gln Glu Ala Val Asn Ala Leu Phe Thr Asn Thr Asn
625                 630                 635                 640
Pro Arg Arg Leu Lys Thr Asp Val Thr Asp Tyr His Ile Asp Gln Val
                645                 650                 655
Ser Asn Leu Val Ala Cys Leu Ser Asp Glu Phe Cys Leu Asp Glu Lys
                660                 665                 670
Arg Glu Leu Leu Glu Lys Val Lys Tyr Ala Lys Arg Leu Ser Asp Glu
                675                 680                 685
Arg Asn Leu Leu Gln Asp Pro Asn Phe Thr Ser Ile Asn Lys Gln Pro
                690                 695                 700
```

```
Asp Phe Ile Ser Thr Asn Glu Gln Ser Asn Phe Thr Ser Ile His Glu
705                 710                 715                 720

Gln Ser Glu His Gly Trp Trp Gly Ser Glu Asn Ile Thr Ile Gln Glu
                725                 730                 735

Gly Asn Asp Val Phe Lys Glu Asn Tyr Val Thr Leu Pro Gly Thr Phe
            740                 745                 750

Asn Glu Cys Tyr Pro Thr Tyr Leu Tyr Gln Lys Ile Gly Glu Ser Glu
        755                 760                 765

Leu Lys Ala Tyr Thr Arg Tyr Gln Leu Arg Gly Tyr Ile Glu Asp Ser
    770                 775                 780

Gln Asp Leu Glu Ile Tyr Leu Ile Arg Tyr Asn Ala Lys His Glu Thr
785                 790                 795                 800

Leu Asp Val Pro Gly Thr Glu Ser Leu Trp Pro Leu Ser Val Glu Ser
                805                 810                 815

Pro Ile Gly Arg Cys Gly Glu Pro Asn Arg Cys Ala Pro His
            820                 825                 830

<210> SEQ ID NO 58
<211> LENGTH: 2493
<212> TYPE: DNA
<213> ORGANISM: Bacillus thuringiensis

<400> SEQUENCE: 58
atgaatctat caccagatgc tcgtattgaa gatagcttgt gtgtagccga ggtgaacaat     60
attgatccat ttgttagcgc atcaacagtc caaacgggta taaacatagc tggtagaata    120
ttgggcgtat taggtgtgcc gtttgctgga caactagcta gtttttatag ttttcttgtt    180
ggggaattat ggcctagtgg cagagatcct tgggaaattt tcctggaaca tgtagaacaa    240
cttataagac aacaagtaac agaaaatact aggaatacgg ctattgctcg attagaaggt    300
ctaggaagag gctatagatc ttaccagcag gctcttgaaa cttggttaga taaccgaaat    360
gatgcaagat caagaagcat tattcttgag cgctatgttg ctttagaact tgacattact    420
actgctatac cgcttttcag aatacgaaat gaagaagttc cattattaat ggtatatgct    480
caagctgcaa atttacacct attattattg agagacgcat cccttttttgg tagtgaatgg    540 gggatggcat cttccgatgt taaccaatat taccaagaac aaatcagata tacagaggaa    600
tattctaacc attgcgtaca atggtataat acagggctaa ataacttaag agggacaaat    660
gctgaaagtt ggttgcggta taatcaattc cgtagagacc taacgttagg ggtattagat    720
ttagtagccc tattcccaag ctatgatact cgcacttatc caatcaatac gagtgctcag    780
ttaacaagag aaatttatac agatccaatt gggagaacaa atgcaccttc aggatttgca    840
agtacgaatt ggtttaataa taatgcacca tcgttttctg ccatagaggc tgccattttc    900
aggcctccgc atctacttga ttttccagaa caacttacaa tttacagtgc atcaagccgt    960
tggagtagca ctcaacacat gaattattgg gtgggacata ggcttaactt ccgcccaata   1020
ggagggacat taaatacctc aacacaagga cttactaata atacttcaat taatcctgta   1080
acattacagt ttacgtctcg tgacgtttat agaacagaat caaatgcagg gacaaatata   1140
ctatttacta ctcctgtgaa tggagtacct tgggctagat ttaattttat aaaccctcag   1200
aatatttatg aaagaggcgc cactacctac agtcaaccgt atcagggagt tgggattcaa   1260
ttatttgatt cagaaactga attaccacca gaaacaacag aacgaccaaa ttatgaatct   1320
tatagtcata gattatctca tataggacta atcataggaa acactttgag agcaccagtc   1380
```

```
tattcttgga cgcatcgtag tgcagatcgt acgaatacga ttggaccaaa tagaatcacc   1440
caaatcccaa tggtaaaagc atccgaactt cctcaaggta ccactgttgt tagaggacca   1500
ggatttactg gtggggatat tcttcgaaga acgaatactg gtggatttgg accgataaga   1560
gtaactgtta acggaccatt aacacaaaga tatcgtatag gattccgcta tgcttcaact   1620
gtagattttg atttctttgt atcacgtgga ggtactactg taaataattt tagattccta   1680
cgtacaatga acagtggaga cgaactaaaa tacggaaatt ttgtgagacg tgctttact    1740 acaccttta cttttacaca aattcaagat ataattcgaa cgtctattca aggccttagt    1800
ggaaatgggg aagtgtatat agataaaatt gaaattattc agttactgc aaccttcgaa     1860 gcagaatatg atttagaaag agcgcaagag gcggtgaatg ctctgtttac taatacgaat   1920
ccaagaagat tgaaaacaga tgtgacagat tatcatattg atcaagtatc caatttagtg   1980
gcgtgtttat cggatgaatt ctgcttggat gaaagagag aattacttga gaaagtgaaa     2040
tatgcgaaac gactcagtga tgaaagaaac ttactccaag atccaaactt cacatccatc   2100
aataagcaac cagacttcat atctactaat gagcaatcga atttcacatc tatccatgaa   2160
caatctgaac atggatggtg gggaagtgag aacattacca tccaggaagg aaatgacgta   2220
tttaaagaga attacgtcac actaccgggt acttttaatg agtgttatcc gacgtattta   2280
tatcaaaaaa tagggagtc ggaattaaaa gcatatactc gctaccaatt aagaggttat    2340
attgaagata gtcaagattt agagatatat ttgattcgtt ataatgcgaa acatgaaaca   2400
ttggatgttc caggtaccga gtccctatgg ccgctttcag ttgaaagccc aatcggaagg   2460
tgcggagaac cgaatcgatg cgcaccacat tga                                2493
```

<210> SEQ ID NO 59
<211> LENGTH: 663
<212> TYPE: PRT
<213> ORGANISM: Bacillus thuringiensis
<400> SEQUENCE: 59

```
Met Ser Ser Asn Thr Thr Val Asp Lys Asn Phe Thr Asn Ser Leu Glu
1               5                   10                  15

Asn Asn Thr Asn Met Glu Leu Gln Asn Ile Asn Tyr Glu Asp Cys Leu
            20                  25                  30

Arg Met Ser Glu Tyr Glu Gly Ile Glu Pro Phe Val Ser Val Ser Thr
        35                  40                  45

Ile Gln Thr Gly Ile Gly Ile Ala Gly Lys Ile Leu Gly Thr Leu Gly
    50                  55                  60

Val Pro Phe Ala Gly Gln Val Ala Ser Leu Tyr Ser Phe Ile Leu Gly
65                  70                  75                  80

Glu Leu Trp Pro Lys Gly Lys Ser Gln Trp Glu Ile Phe Met Glu His
                85                  90                  95

Val Glu Glu Ile Ile Asn Gln Lys Ile Ser Thr Tyr Ala Arg Ser Lys
            100                 105                 110

Ala Leu Thr Asp Leu Lys Gly Leu Gly Asp Ala Leu Ala Val Tyr His
        115                 120                 125

Glu Ser Leu Glu Ser Trp Val Gly Asn Arg Asn Asn Thr Arg Ala Arg
    130                 135                 140

Ser Val Val Lys Ser Gln Tyr Ile Ala Leu Glu Leu Met Phe Val Gln
145                 150                 155                 160

Lys Leu Pro Ser Phe Ala Val Ser Gly Glu Glu Val Thr Leu Leu Pro
                165                 170                 175
```

```
Ile Tyr Ala Gln Ala Ala Asn Leu His Leu Leu Leu Arg Asp Ala
                180                 185                 190
Ser Ile Phe Gly Lys Glu Trp Gly Leu Ser Ser Glu Ile Ser Thr
            195                 200                 205
Phe Tyr Asn Arg Gln Val Glu Arg Ala Gly Asp Tyr Ser Asp His Cys
        210                 215                 220
Val Lys Trp Tyr Ser Thr Gly Leu Asn Asn Leu Arg Gly Thr Asn Ala
225                 230                 235                 240
Glu Ser Trp Val Arg Tyr Asn Gln Phe Arg Arg Asp Met Thr Leu Met
                245                 250                 255
Val Leu Asp Leu Val Ala Leu Phe Pro Ser Tyr Asp Thr Gln Met Tyr
            260                 265                 270
Pro Ile Lys Thr Thr Ala Gln Leu Thr Arg Glu Val Tyr Thr Asp Ala
        275                 280                 285
Ile Gly Thr Ile His Pro His Pro Ser Phe Thr Ser Thr Thr Trp Tyr
        290                 295                 300
Asn Asn Asn Ala Pro Ser Phe Ser Ala Ile Glu Ala Ala Val Val Arg
305                 310                 315                 320
Asn Pro His Leu Leu Asp Phe Leu Glu Gln Val Thr Ile Tyr Ser Leu
                325                 330                 335
Leu Ser Arg Trp Ser Asn Thr Gln Tyr Met Asn Met Trp Gly Gly His
            340                 345                 350
Lys Leu Glu Phe Arg Thr Ile Gly Gly Thr Leu Asn Thr Ser Thr Gln
        355                 360                 365
Gly Ser Thr Asn Thr Ala Ile Asn Pro Val Thr Leu Pro Phe Thr Ser
370                 375                 380
Arg Asp Val Tyr Arg Thr Glu Ser Leu Ala Gly Leu Asn Leu Phe Leu
385                 390                 395                 400
Thr Gln Pro Val Asn Gly Val Pro Arg Val Asp Phe His Trp Lys Phe
                405                 410                 415
Val Thr His Pro Ile Ala Ser Asp Asn Phe Tyr Tyr Pro Gly Tyr Ala
            420                 425                 430
Gly Ile Gly Thr Gln Leu Gln Asp Ser Glu Asn Glu Leu Pro Ser Glu
        435                 440                 445
Ala Thr Gly Gln Pro Asn Tyr Glu Ser Tyr Ser His Arg Leu Ser His
        450                 455                 460
Ile Gly Leu Ile Ser Ala Ser His Val Lys Ala Leu Val Tyr Ser Trp
465                 470                 475                 480
Thr His Arg Ser Ala Asp Arg Thr Asn Thr Ile Glu Pro Asn Arg Ile
                485                 490                 495
Thr Gln Ile Pro Leu Val Lys Ala Leu Asn Leu His Ser Gly Ala Thr
            500                 505                 510
Val Val Arg Gly Pro Gly Phe Thr Gly Gly Asp Ile Leu Arg Arg Thr
        515                 520                 525
Asn Thr Gly Thr Phe Gly Asp Ile Arg Leu Asn Ile Asn Val Pro Leu
        530                 535                 540
Ser Gln Arg Tyr Arg Val Arg Ile Arg Tyr Ala Ser Thr Thr Asp Leu
545                 550                 555                 560
Gln Phe Phe Thr Arg Ile Asn Gly Thr Thr Val Asn Ile Ala Asn Phe
                565                 570                 575
Ser Arg Thr Met Asn Arg Gly Asp Asn Leu Glu Ser Arg Ser Phe Arg
            580                 585                 590
Thr Ala Gly Phe Ser Thr Pro Phe Asn Phe Ser Asn Ala Gln Ser Thr
```

```
                595                 600                 605
Phe Thr Leu Gly Ala Gln Ser Phe Ser Asn Gln Glu Val Tyr Ile Asp
    610                 615                 620

Arg Val Glu Phe Val Pro Ala Glu Val Thr Phe Glu Ala Glu Tyr Asp
625                 630                 635                 640

Leu Glu Arg Ala Gln Glu Ala Val Asn Ala Leu Phe Thr Asn Thr Asn
                645                 650                 655

Pro Arg Arg Leu Lys Thr Asp
            660

<210> SEQ ID NO 60
<211> LENGTH: 1992
<212> TYPE: DNA
<213> ORGANISM: Bacillus thuringiensis

<400> SEQUENCE: 60
atgtctagca atacgacagt tgataaaaac tttacaaatt cactagaaaa caacacaaat      60
atggaattac aaatattaa ttatgaagat tgtttgagaa tgtctgagta tgaaggtata     120
gagccgtttg ttagtgtatc aacaattcaa acaggtattg gtattgcggg taaaatactt     180
ggtaccctag gcgttccttt tgcaggacaa gtagctagtc tttatagttt tatcttaggt     240
gagctatggc ctaaggggaa aagccaatgg gaaatcttta tggaacatgt agaagagatt     300
attaatcaaa aatatcaac ttatgcaaga agtaaagcac ttacagactt gaaggattta     360
ggagatgcct tagctgtcta ccatgaatcg ctggaaagtt gggttggaaa tcgtaataac     420
acaagggcta ggagtgttgt caagagccaa tatatcgcat tagaattgat gttcgttcag     480
aaactacctt cttttgcagt gtctggagag gaggtaacat tattaccgat atatgcccaa     540
gctgcaaatt tacatttgtt gctattacga gatgcgtcta ttttttggaaa agagtgggga     600 ttatcatctt cagaaatttc aacattttat aaccgtcaag tcgaacgagc aggagattat     660
tccgaccatt gtgtgaaatg gtatagcaca ggtctaaata acttgagggg tacaaatgcc     720
gaaagttggg tacgatataa tcaattccgt agagacatga ctttaatggt actagattta     780
gtggcactat ttccaagcta tgatacaaa atgtatccaa ttaaaactac agcccaactt     840
acaagagaag tatatacaga cgcaattggg acaatacatc cgcatccaag ttttacaagt     900
acgacttggt ataataataa tgcaccttcg ttctctgcca tagaggctgc tgttgttcga     960
aacccgcatc tactcgattt tctagaacaa gttacaattt acagcttatt aagtcgatgg    1020
agtaacactc agtatatgaa tatgtgggga ggacataaac tagaattccg aacaatagga    1080
ggaacgttaa ataccctcaac acaaggatct actaatactg ctattaatcc tgtaacatta    1140
ccgttcactt ctcgagacgt ctataggact gaatcattgg cagggctgaa tctattttta    1200
actcaacctg ttaatggagt acctagggtt gattttcatt ggaaattcgt cacacatccg    1260
atcgcatctg ataatttcta ttatccaggg tatgctggaa ttgggacgca attacaggat    1320
tcagaaaatg aattaccatc tgaagcaaca ggacagccaa attatgaatc ttatagtcat    1380
agattatctc atataggact catttcagca tcacatgtga agcattggt atattcttgg    1440 acacatcgta gtcagatcg tacaaataca attgaaccaa atagaattac acaaatacca    1500
ttggtaaaag cacttaacct tcattcaggt gctactgttg ttagagggcc aggatttaca    1560 ggtgggata tccttcgtag aacgaatact ggtacatttg agatatacg tttaaatatt    1620 aatgtgccat tatcccaaag atatcgcgta aggattcgtt atgcttctac tacagattta    1680
caatttttca cgagaattaa tggaaccact gttaatattg ctaatttctc aagaactatg    1740
```

```
aataggggggg ataatttaga atctagaagt tttagaactg caggatttag tactcctttt    1800
aatttttcaa atgcccaaag cacattcaca ttgggtgctc agagttttc aaatcaggaa      1860 gtttatatag atagagtcga atttgttccg gcagaggtaa ccttcgaagc agaatatgat    1920
ttagaaagag cgcaagaggc ggtgaatgct ctgtttacta atacgaatcc aagaagattg   1980
aaaacagatt aa                                                          1992
```